(12) United States Patent
Montalban et al.

(10) Patent No.: US 8,853,419 B2
(45) Date of Patent: Oct. 7, 2014

(54) PROCESSES FOR THE PREPARATION OF (R)-2-(7-(4-CYCLOPENTYL-3-(TRIFLUOROMETHYL)BENZYLOXY)-1,2,3,4-TETRAHYDROCYCLOPENTA[B]INDOL-3-YL)ACETIC ACID AND SALTS THEREOF

(75) Inventors: Antonio Garrido Montalban, San Diego, CA (US); Daniel J. Buzard, San Diego, CA (US); John A. DeMattei, Berthoud, CO (US); Tawfik Gharbaoui, Escondido, CA (US); Stephen R. Johannsen, San Diego, CA (US); Ashwin M. Krishnan, San Diego, CA (US); Young Mi Khulman, Plainsboro, NJ (US); You-An Ma, Poway, CA (US); Michael John Martinelli, San Diego, CA (US); Suzanne Michiko Sato, San Diego, CA (US); Dipanjan Sengupta, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 13/575,458

(22) PCT Filed: Jan. 27, 2011

(86) PCT No.: PCT/US2011/000153
§ 371 (c)(1),
(2), (4) Date: Jul. 26, 2012

(87) PCT Pub. No.: WO2011/094008
PCT Pub. Date: Aug. 4, 2011

(65) Prior Publication Data
US 2012/0295947 A1    Nov. 22, 2012

Related U.S. Application Data

(60) Provisional application No. 61/336,835, filed on Jan. 27, 2010.

(51) Int. Cl.
*C07D 209/80*    (2006.01)
*A61K 31/403*    (2006.01)
*C07D 209/94*    (2006.01)

(52) U.S. Cl.
CPC .................................. *C07D 209/94* (2013.01)
USPC ............................................ 548/439; 514/411

(58) Field of Classification Search
None
See application file for complete search history.

(56) References Cited

U.S. PATENT DOCUMENTS

| | | |
|---|---|---|
| 3,206,470 A | 9/1965 | William et al. |
| 4,057,559 A | 11/1977 | Asselin et al. |
| 4,782,076 A | 11/1988 | Mobilio et al. |
| 4,810,699 A | 3/1989 | Sabatucci et al. |
| 5,221,678 A | 6/1993 | Atkinson et al. |
| 5,776,967 A | 7/1998 | Kreft et al. |
| 5,830,911 A | 11/1998 | Failli et al. |
| 6,410,583 B1 | 6/2002 | Labelle et al. |
| 6,960,692 B2 | 11/2005 | Kohno et al. |
| 7,250,441 B2 | 7/2007 | Gopalsamy et al. |
| 8,415,484 B2 | 4/2013 | Jones et al. |
| 2003/0083269 A1 | 5/2003 | Brouillette et al. |
| 2003/0211421 A1 | 11/2003 | Hanabata et al. |
| 2004/0224941 A1 | 11/2004 | Seko et al. |
| 2004/0254222 A1 | 12/2004 | Kohno et al. |
| 2005/0004114 A1 | 1/2005 | Whitehouse et al. |
| 2005/0009786 A1 | 1/2005 | Pan et al. |
| 2005/0014724 A1 | 1/2005 | Marsilje et al. |
| 2005/0014725 A1 | 1/2005 | Mi et al. |
| 2005/0014728 A1 | 1/2005 | Pan et al. |
| 2005/0033055 A1 | 2/2005 | Bugianesi et al. |
| 2005/0239899 A1 | 10/2005 | Fecke et al. |
| 2006/0004010 A1 | 1/2006 | Habashita et al. |
| 2006/0063821 A1 | 3/2006 | Gopalsamy et al. |
| 2006/0079542 A1 | 4/2006 | Nestor |

(Continued)

FOREIGN PATENT DOCUMENTS

| | | |
|---|---|---|
| EP | 0468785 A2 | 1/1992 |
| EP | 1650186 A1 | 4/2006 |

(Continued)

OTHER PUBLICATIONS

Berge et al., "Pharmaceutical Salts," J Pharma Sci., 1977, 66(1):1-19.

(Continued)

*Primary Examiner* — Michael Barker
(74) *Attorney, Agent, or Firm* — Fish & Richardson P.C.; Lyle W. Spruce

(57) ABSTRACT

The present invention relates to processes and intermediates useful in the preparation of (R)-2-(7-(4-cyclopentyl-3-(trifluoromethyl)benzyloxy)-1,2,3,4-tetrahydrocyclopenta[b]indol-3-yl)acetic acid of Formula (Ia) and salts thereof, an S1P1 receptor modulator that is useful in the treatment of S1P1 receptor-associated disorders, for example, diseases and disorders mediated by lymphocytes, transplant rejection, autoimmune diseases and disorders, inflammatory diseases and disorders (e.g., acute and chronic inflammatory conditions), cancer, and conditions characterized by an underlying defect in vascular integrity or that are associated with angiogenesis such as may be pathologic (e.g., as may occur in inflammation, tumor development and atherosclerosis).

(Ia)

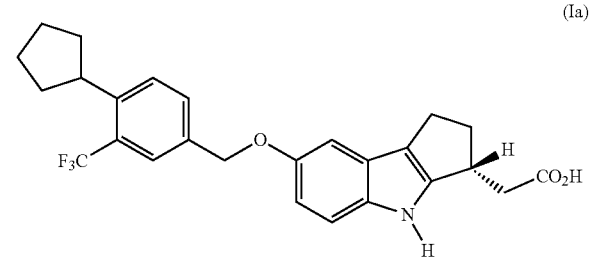

24 Claims, 8 Drawing Sheets

(56) References Cited

U.S. PATENT DOCUMENTS

| | | |
|---|---|---|
| 2006/0122222 A1 | 6/2006 | Whitehouse et al. |
| 2006/0160771 A1 | 7/2006 | Kohno et al. |
| 2006/0211656 A1 | 9/2006 | Albert et al. |
| 2006/0223866 A1 | 10/2006 | Evindar et al. |
| 2007/0010494 A1 | 1/2007 | Ehrhardt et al. |
| 2007/0043014 A1 | 2/2007 | Doherty et al. |
| 2007/0060573 A1 | 3/2007 | Wortmann et al. |
| 2007/0149595 A1 | 6/2007 | Tanaka et al. |
| 2007/0149597 A1 | 6/2007 | Nishi et al. |
| 2007/0167425 A1 | 7/2007 | Nakade et al. |
| 2007/0173487 A1 | 7/2007 | Saha et al. |
| 2007/0173507 A1 | 7/2007 | Hirata |
| 2007/0191313 A1 | 8/2007 | Beard et al. |
| 2007/0191371 A1 | 8/2007 | Bennett et al. |
| 2007/0191468 A1 | 8/2007 | Nishi et al. |
| 2007/0244155 A1 | 10/2007 | Sharma et al. |
| 2007/0254886 A1 | 11/2007 | Habashita et al. |
| 2008/0051418 A1 | 2/2008 | Maekawa et al. |
| 2008/0153882 A1 | 6/2008 | Nishi et al. |
| 2008/0200535 A1 | 8/2008 | Ohmori et al. |
| 2008/0207584 A1 | 8/2008 | Habashita et al. |
| 2008/0319077 A1 | 12/2008 | Suzuki et al. |
| 2009/0012093 A1 | 1/2009 | Fukatsu et al. |
| 2009/0076070 A1 | 3/2009 | Harada et al. |
| 2009/0131438 A1 | 5/2009 | Ono et al. |
| 2009/0137685 A1 | 5/2009 | Kojima et al. |
| 2009/0325907 A1 | 12/2009 | Kohno et al. |
| 2010/0267778 A1 | 10/2010 | Kusuda et al. |
| 2010/0273806 A1 | 10/2010 | Jones et al. |
| 2010/0292233 A1 | 11/2010 | Jones et al. |
| 2011/0130409 A1 | 6/2011 | Jones et al. |
| 2011/0160243 A1 | 6/2011 | Jones et al. |
| 2012/0064060 A1 | 3/2012 | Habashita et al. |
| 2012/0329848 A1 | 12/2012 | Jones et al. |
| 2013/0184307 A1 | 7/2013 | Jones et al. |

FOREIGN PATENT DOCUMENTS

| | | |
|---|---|---|
| EP | 1826197 A1 | 6/2008 |
| EP | 2003132 A1 | 12/2008 |
| EP | 1772145 B1 | 3/2011 |
| EP | 2017263 A4 | 11/2011 |
| GB | 1436893 | 5/1976 |
| JP | 2007262009 A | 10/2007 |
| WO | WO9106537 A2 | 5/1991 |
| WO | WO9714674 A1 | 4/1997 |
| WO | WO0064888 A1 | 11/2000 |
| WO | WO0239987 A2 | 5/2002 |
| WO | WO02064616 A2 | 8/2002 |
| WO | WO02092068 A1 | 11/2002 |
| WO | WO03029205 A1 | 4/2003 |
| WO | WO03062252 A1 | 7/2003 |
| WO | WO03061567 A3 | 12/2003 |
| WO | WO03105771 A2 | 12/2003 |
| WO | WO2003074008 A3 | 2/2004 |
| WO | WO2003073986 A3 | 5/2004 |
| WO | WO2004058149 A3 | 9/2004 |
| WO | WO2004074297 A1 | 9/2004 |
| WO | WO2004010949 A3 | 10/2004 |
| WO | WO2004071442 A3 | 10/2004 |
| WO | WO2004096752 A1 | 11/2004 |
| WO | WO2004103309 A2 | 12/2004 |
| WO | WO2004096757 A8 | 1/2005 |
| WO | WO2005000833 A1 | 1/2005 |
| WO | WO2004110979 A3 | 2/2005 |
| WO | WO2004103306 A3 | 3/2005 |
| WO | WO2005021503 A1 | 3/2005 |
| WO | WO2005020882 A3 | 4/2005 |
| WO | WO2005032465 A2 | 4/2005 |
| WO | WO2004103279 A3 | 5/2005 |
| WO | WO2005041899 A2 | 5/2005 |
| WO | WO2005044780 A1 | 5/2005 |
| WO | WO2005058848 A1 | 6/2005 |
| WO | WO2005070886 A1 | 8/2005 |
| WO | WO2005079788 A1 | 9/2005 |
| WO | WO2005082089 A2 | 9/2005 |
| WO | WO2005082841 A1 | 9/2005 |
| WO | WO2005085179 A1 | 9/2005 |
| WO | WO2005097745 A1 | 10/2005 |
| WO | WO2005058295 A3 | 11/2005 |
| WO | WO2005123677 A1 | 12/2005 |
| WO | WO2006001463 A1 | 1/2006 |
| WO | WO2006009092 A1 | 1/2006 |
| WO | WO2006010379 A1 | 2/2006 |
| WO | WO2006011554 A1 | 2/2006 |
| WO | WO2006013948 A1 | 2/2006 |
| WO | WO2006020951 A1 | 2/2006 |
| WO | WO2004113330 A8 | 3/2006 |
| WO | WO2006010544 A3 | 3/2006 |
| WO | WO2006034337 A2 | 3/2006 |
| WO | WO2006043149 A2 | 4/2006 |
| WO | WO 2006/047195 | 5/2006 |
| WO | WO2006064757 A1 | 6/2006 |
| WO | WO2006079406 A1 | 8/2006 |
| WO | WO2006088944 A1 | 8/2006 |
| WO | WO2006100631 A1 | 9/2006 |
| WO | WO2006100633 A1 | 9/2006 |
| WO | WO2006063033 A3 | 11/2006 |
| WO | WO 2006/131336 | 12/2006 |
| WO | WO2006137019 A1 | 12/2006 |
| WO | WO2006137509 A1 | 12/2006 |
| WO | WO2006100635 A3 | 1/2007 |
| WO | WO2007024922 A1 | 3/2007 |
| WO | WO2007037196 A1 | 4/2007 |
| WO | WO2007060626 A1 | 5/2007 |
| WO | WO2007080542 A1 | 7/2007 |
| WO | WO2007083089 A1 | 7/2007 |
| WO | WO2007085451 A2 | 8/2007 |
| WO | WO2007086001 A2 | 8/2007 |
| WO | WO2007091396 A1 | 8/2007 |
| WO | WO2007091501 A1 | 8/2007 |
| WO | WO2007092638 A1 | 8/2007 |
| WO | WO2007109330 A2 | 9/2007 |
| WO | WO2007095561 A3 | 10/2007 |
| WO | WO2007115820 A1 | 10/2007 |
| WO | WO2007116866 A1 | 10/2007 |
| WO | WO2007061458 A3 | 11/2007 |
| WO | WO2007092190 A3 | 11/2007 |
| WO | WO2007129473 A1 | 11/2007 |
| WO | WO2007129745 A1 | 11/2007 |
| WO | WO2007132307 A1 | 11/2007 |
| WO | WO2007100617 A3 | 1/2008 |
| WO | WO2007109334 A3 | 1/2008 |
| WO | WO2008016674 A1 | 2/2008 |
| WO | WO2008018427 A1 | 2/2008 |
| WO | WO2008019090 A2 | 2/2008 |
| WO | WO2008023783 A1 | 2/2008 |
| WO | WO2008024196 A1 | 2/2008 |
| WO | WO2008016692 A3 | 3/2008 |
| WO | WO2008028937 A1 | 3/2008 |
| WO | WO2008029371 A1 | 3/2008 |
| WO | WO2008030843 A1 | 3/2008 |
| WO | WO2008035239 A1 | 3/2008 |
| WO | WO2008029306 A3 | 5/2008 |
| WO | WO2008074820 A1 | 6/2008 |
| WO | WO2008074821 A1 | 6/2008 |
| WO | WO2008076356 A1 | 6/2008 |
| WO | WO2008079382 A1 | 7/2008 |
| WO | WO2008089015 A1 | 7/2008 |
| WO | WO2008091967 A1 | 7/2008 |
| WO | WO2008114157 A1 | 9/2008 |
| WO | WO2008128951 A1 | 10/2008 |
| WO | WO2007098474 A8 | 11/2008 |
| WO | WO2008097819 A3 | 11/2008 |
| WO | WO2008152149 A1 | 12/2008 |
| WO | WO2009019167 A1 | 2/2009 |
| WO | WO2009019506 A1 | 2/2009 |
| WO | WO2009011850 A3 | 3/2009 |
| WO | WO2009064250 A1 | 5/2009 |
| WO | WO2009078983 A1 | 6/2009 |
| WO | WO2009094157 A1 | 7/2009 |
| WO | WO2009103552 A1 | 8/2009 |
| WO | WO 2009/151529 | 12/2009 |

(56) References Cited

FOREIGN PATENT DOCUMENTS

| WO | WO 2009/151621 | 12/2009 |
|---|---|---|
| WO | WO 2009/151626 | 12/2009 |
| WO | WO2010011316 A1 | 1/2010 |
| WO | WO2010027431 A1 | 3/2010 |
| WO | WO 2010/093704 | 8/2010 |
| WO | WO2011005290 A1 | 1/2011 |
| WO | WO2011005295 A1 | 1/2011 |
| WO | WO 2011/059784 | 5/2011 |
| WO | WO2011109471 A1 | 9/2011 |
| WO | WO 2012/015758 | 2/2012 |

OTHER PUBLICATIONS

Kataoka et al., "FTY720, Sphingosine 1-Phosphate Receptor Modulator, Ameliorates Experimental Autoimmune Encephalomyelitis by Inhibition of T Cell Infiltration," Cell Mol. Immunol., Dec. 2005, 2(6):439-448.
Brinkman, "Sphingosine 1-phosphate receptors in health and disease: Mechanistic insights from gene deletion studies and reverse pharmacology," Pharmacol. Ther., 2007, 115:84-105.
Balatoni et al., "FTY720 sustains and restores neuronal function in the DA rat model of MOG-induced experimental autoimmune encephalomyelitis," Brain Res. Bull., 2007, 74:307-316.
Kappos et al., "Oral Fingolimod (FTY720) for Relapsing Multiple Sclerosis," N Engl J Med., 2006, 355:1124-1140.
Zhang et al., "FTY720: A Most Promising Immunosuppressant Modulating Immune Cell Functions," Mini Rev. Med Chem., 2007, 7:845-850.
Brinkmann, "Sphingosine 1-phosphate receptors in health and disease: Mechanistic insights from gene deletion studies and reverse pharmacology," Pharmacol Ther., 2007, 115:84-105.
Dev et al., "Brain sphingosine-1-phosphate receptors: Implication for FTY720 in the treatment of multiple sclerosis," Pharmacol Ther., 2008, 117:77-93.
Premenko-Lanier et al., "Transient FTY720 treatment promotes immune-mediated clearance of a chronic viral infection," Nature, Aug. 2008, 454:894-899.
Bar-Haim et al., "Interrelationship between Dendritic Cell Trafficking and *Francisella tularensis* Dissemination following Airway Infection," PLoS Pathog., 2008, 4(11):e1000211, 15 pages.
Raveney et al., "Fingolimod (FTY720) as an Acute Rescue Therapy for Intraocular Inflammatory Disease," Arch Ophthalmol, 2008, 126(10):1390-1395.
Ishii et al., "Sphingosine-1-phosphate mobilizes osteoclast precursors and regulates bone homeostasis," Nature, Mar. 2006, 458(7237):524-528.
Miron et al., "FTY720 Modulates Human Oligodendrocyte Progenitor Process Extension and Survival," Ann Neurol, 2008, 63:61-71.
Coelho et al., "The Immunomodulator FTY720 has a direct cytoprotective effect in oligodendrocyte Progenitors," J Pharmacol. Exp. Ther., 2007, 323:626-635.
Jung et al., "Functional Consequences of S1P Receptor Modulation in Rat Oligodendroglial Lineage Cells," Glia, 2007, 55:1656-1667.
Kimura et al., "Essential Roles of Sphingosine 1-Phosphate/S1P1 Receptor Axis in the Migration of Neural Stem Cells Toward a Site of Spinal Cord Injury," Stem Cells, 2007, 25:115-124.
Sauer et al., "Involvement of Smad Signlaing in Sphingosine 1-Phosphate-mediated Biological Responses of Keratinocytes," J Biol. Chem., 2004, 279:38471-38479.
Kim et al., "Sphingosine-1-phosphate inhibits human keratinocyte proliferation via Akt/protein kinase B inactivation," Cell Signal, 2004, 16:89-95.
Koreck et al., "The Role of Innate Immunity in the Pathogensis of Acne," Dermatol., 2003, 206:96-105.
Webster, "The Pathophysiology of Acne," Cutis, 2005, 76(suppl. 2):4-7.
Oo et al., "Immunosuppressive and Anti-angiogenic Sphingosine 1-Phosphate Receptor-1 Agonists Induce Ubiquitinylation and Proteasomal Degradation of the Receptor," J Biol Chem., 2007, 282(12):9082-9089.
Schmid et al., "The Immunosuppressant FTY720 inhibits tumor Angiogenesis via the Sphingosine 1-Phosphate Receptor 1," J Cell Biochem., 2007, 101:259-270.
LaMontagne et al., "Antagonism of Sphingosine-1-Phosphate Receptors by FTY720 Inhibits Angiogenesis and Tumor Vascularization," Cancer Res., 2006, 66:221-231.
Lee et al., "FTY720: A Promising Agent for Treatment of Metastatic Hepatocellular Carcinoma," Clin. Cancer Res., 2005, 11:8458-8466.
Sanchez et al., "Phosphorylation and Action of the Immunomodulator FTY720 Inhibits Vascular Endothelial Cell Growth Factor-induced Vascular Permeability," J Biol Chem., 2003, 278(47):47281-47290.
Lima et al., "FTY720 Treatment Prolongs Skin Graft Survival in a Completely Incompatible Strain Combination," Transplant Proc., 2004, 36:1015-1017.
Yan et al., "Discovery of 3-arylpropionic acids as potent agonists of sphingosine-1-phosphate receptor-1 (S1P1) with high selectivity against all other known S1P receptor subtypes," Bioorg. Med. Chem. Lett., 2006, 16:3679-3683.
Suzuki et al., "Immunosuppressive effect of a new drug, FTY720, on lymphocyte responses in vitro and cardiac allograft survival in rats," Transplant Immunol., 1996, 4:252-255.
Yanagawa et al., "FTY720, a Novel Immunosuppressant, Induces Sequestration of Circulating Mature Lymphocytes by Acceleration of Lymphocyte Homing in Rats. II. FTY720 Prolongs Skin Allograft Survival by Decreasing T Cell Infiltration into Grafts But not cytokine production in vivo," J Immunol., 1998, 160:5493-5499.
Chiba et al., "Role of Sphingosine 1-Phosphate Receptor Type 1 in Lumphocyte Egress from Secondary Lymphoid Tissues and Thymus," Cell Mole Immunol., Feb. 2006, 3(1):11-19.
Shimizu et al., "KRP-203, a Novel Synthetic Immunosuppressant, Prolongs Graft Survival and Attenuates Chronic Rejection in Rat Skin and Heart Allografts," Circulation, 2005, 111:222-229.
Suzuki et al., "Efficacy of Mycophenolic Acid Combined with KRP-203, a Novel Immunomodulator, in a Rat Heart Transplantation Model," J Heart Lung Transplant, 2006, 25:302-309.
Fujishiro et al., "Change from Cyclosporine to Combination Therapy of Mycophenolic Acid with the New Sphinogosine-1-phosphate Receptor Agonist, KRP-203, Prevents Host Nephrotoxicity and Transplant Vasculopathy in Rats," J Heart Lung Transplant, 2006, 25:825-833.
Pan et al., "A Monoselective Sphingosine-1-Phosphate Receptor-1 Agonist Prevents Allograft Rejection in a Stringent Rat Heart Transplantation Model," Chem. Biol., 2006, 13:1227-1234.
Sakagawa et al., "Rejection following donor or recipient preoperative treatment with FTY720 in rat small bowel transplantation," Transpl. Immunol., 2004, 13:161-168.
Liu et al., "Long-Term Effect of FTY720 on Lymphocyte Count and Islet Allograft Survival in Mice," Microsurgery, 2007, 27:300-304.
Truong et al., "Human Islet Function is not Impaired by the Sphingosine-1-Phosphate Receptor Modulator FTY720," Am J Transplantation, 2007, 7:2031-2038.
Coste et al., "Antinociceptive activity of the S1P-receptor agonist FTY720," J Cell Moll Med., 2008, 12(3):995-1004.
Nakashima et al., "Impaired Initiation of Contact Hypersensitivity by FTY720," J Invest Dermatol., 2008, 128:2833-2841.
Kohno et al., "A Novel Immunomodulator, FTY720, Prevents Development of Experimental Autoimmune Myasthenia Gravis in C57BL/6 Mice," Biol Pharma Bull., 2005, 28(4):736-739.
Guillory, "Generation of Polymorphs, Hydrates, Solvates, and Amorphous Solids," Polymorphism in Pharmaceutical Solids, 1999, 95:202-209.
Remington, The Science and Practice of Pharmacy, 20th Edition, 2000, Lippincott Williams & Wilkins, (Editors: Gennaro et al.).
Greene and Wuts, Protective Groups in Organic Synthesis, 3rd Ed., Wiley & Sons, 1999.
Higuchi and Stella, "Pro-drugs as Novel Delivery Sytems," A.C.S. Symposium Series 14, 1975, 129 pages.
Vachal et al., "Highly selective and potent agonists of sphinogosin-1-phosphate 1 (S1P1) receptor," Bioorganic Med Chem Lett., Jul. 2006, 16(14):3684-3687.
Sturino et al., "Discovery of a potent and selective prostaglandin D2 receptor antagonist, [(3r)-4-(4-chloro-benzyl)-7-fluoro-5-

(56) References Cited

OTHER PUBLICATIONS (methylsulfonyl)-1,2,3,4-tetrahydrocyclopenta[b]indol-3-yl]-acetic acid (MK-0524)," J Med. Chem., Feb. 2007, 50(4):794-806.
Chun et al., "International Union of Pharmacology. XXXIV. Lysophospholipid Receptor Nomenclature," Pharmacol. Rev., 2002, 54(2):256-269.
Hale et al., "Potent S1P receptor agonists replicate the pharmacologic actions of the novel immune modulator FTY720," Bioorganic Med Chem. Lett., 2004, 14:3351-335.
Rosen et al., "Egress: a receptor-regulated step in lymphocyte trafficking," Immunol. Rev. 2003, 195:160-177.
Schwab and Cyster, "Finding a way out: lymphocyte egress from lymphoid organs," Nature Immunol., Dec. 2007, 8 (12):1295-1301.
Matloubian et al., "Lymphocyte egress from thymus and peripheral lymphoid organs in dependent on S1P receptor 1," Nature, Jan. 2004, 427:355-360.
Baumruker et al., "FTY720, an immunomodulatory sphingolipid mimetic: translation of a novel mechanism into clinical benefit in multiple sclerosis," Expert Opin. Investig. Drugs, 2007, 16(3):283-289.
Sanna et al., "Sphingosine 1-Phosphate (S1P) Receptor Subtypes S1P1 and S1P3, Respectively, Regulate Lymphocyte Recirculation and Heart Rate," 2004, 279(14):13839-13848.
Brinkmann et al., "FTY720: Altered Lymphocyte Traffic Results in Allograft Protection," Transplantation, Sep. 2001, 72 (5):764-769.
Brinkmann et al., "FTY720 Alters Lymphocyte Homing and Protects Allografts Without Inducing General Immunosuppression," Transplantation Proc., 2001, 33:530-531.
Sanna et al., "Enhancement of cappillary leakage and restoration of lymphocyte egress by a chiral S1P1 antagonist in vivo," Nature Chem Biol., Aug. 2006, 2(8):434-441.
Groeneveld, "Vascular pharmacology of acute lung injury and acute respiratory distress syndrome," Vascular Pharmacol., 2003, 39:247-256.
Martini et al., "Current perspectives on FTY720," Expert Opin. Investig. Drugs, 2007, 16:505-518.
Chiba, "FTY720, a new class of immunomodulator, inhibits lymphocyte egress from secondary lymphoid tissues and thymus by agonistic activity at sphingosine 1-phosphate receptors," Pharmacol. Ther., 2005, 108:308-319.
Budde et al., "First Human Trial of FTY720, a Novel Immunomodulator, in Stable Renal Transplant Patients," J Am Soc. Nephrol., 2002, 13:1073-1083.
Ogawa et al., "A novel sphingosine-1-phosphate receptor agonist KRP-203 attenuates rate autoimmune myocarditis," Biochem. Biophys. Res. Commun., 2007, 361:621-628.
Kitabayashi et al., "FTY720 Prevents Development of Experimental Autoimmune Myocarditis Through Reduction of Circulating Lymphocytes," J Cardiovasc. Pharmacol. 2000, 35:410-416.
Miyamoto et al., "Therapeutic Effects of FTY720, a New Immunosuppressive Agent, in a Murine Model of Acute Viral Myocarditis," J Am Coll Cardiol., 2001, 37(6):1713-1718.
Mizushima et al., "Therapeutic Effects of a New Lymphocyte Homing Reagent FTY720 in Interleukin-10 Gene-deficient Mice with Colitis," Inflamm Bowel Dis., May 2004, 10(3):182-192.
Deguchi et al., "The S1P receptor modulator FTY720 prevents the development of experimental colitis in mice," Oncol. Rep., 2006, 16:699-703.
Fujii et al., "FTY720 suppresses CD4+CD44highCD62L-effector memory T cell-mediated colitis," Am J Physol Gastrointest Liver Physiol., 2006, 291:G267-G274.
Daniel et al., "FTY720 Ameliorates Th1-Mediated Colitis in Mice by Directly Affecting the Functional Activity of DC4 +CD25+ Regulatory T Cell1," J Immunol., 2007, 178:2458-2468.
Martini et al., "S1P modulator FTY720 limits matrix expansion in acute anti-thy1 mesangioproliferative glomerulonephritis," Am J Physiol Renal Physiol., 2007, 292:F1761-F1770.
Idzko et al., "Local application of FTY720 to the lung abrogates experimental asthma by altering dendritic cell function," J Clinc Invest., Nov. 2006, 116(11):2935-2944.

Sawicka et al., "Inhibition of Th1- and Th2-Mediated Airway Inflammation by the Sphingosine 1-Phosphate Receptor Agonist FTY720," J Immunol., 2003, 171:6206-6214.
Kohno et al., "A Novel Immunomodulator, FTY720, Prevents Spontaneous Dermatitis in NC/Nga Mice," BIol. Pharm. Bull., 2004, 27(9):1392-1396.
Kaudel et al., "FTY720 for Treatment of Ischemia-Reperfusion Injury Following Complete Renal Ischemia; Impact on Long-Term Survival and T-Lymphocyte Tissue Infiltration," Transplantation Proc., 2007, 39:499-502.
Okazaki et al., "Effects of FTY720 in MRL-lpr/lpr mice: therapeutic potential in systemic lupus erythematosus," J Rheumatol., 2002, 29:707-716.
Herzinger et al., "Sphingosine-1-Phosphate Signaling and the Skin," Am J Clin Dermatol., 2007, 8(6):329-336.
Matsuura et al., "Effect of FTY720, a novel immunosuppressant, on adjuvant- and collagen-induced arthritis in rats," Int. J Immunopharmacol. 2000, 22:323-331.
Matsuura et al., "Effect of FTY720, a novel immunosuppressant, on adjuvant-induced arthritis in rats," Inflamm. Res. 2000, 49:404-410.
Kurose et al., "Effects of FTY720, a novel immunosuppressant, on experimental autoimmune uveoretinitis in rats," Exp. Eye Res., 2000, 70:7-15.
Fu et al., "Long-term islet graft survival in streptozotocin- and autoimmune-induced diabetes models by immunosuppressive and potential insulinotropic agent FTY720," Transplantation, May 2002, 73(9):1425-1430.
Maki et al., "Prevention of autoimmune diabetes by FTY720 in Nonobese diabetic mice," Transplantation, Dec. 2002, 74(12):1684-1686.
Yang et al., "The immune modulator FYT720 prevents autoimmune diabetes in nonobese diabetic mice," Clin. Immunol., 2003, 107:30-35.
Maki et al., Prevention and Cure of Autoimmune Diabetes in Nonobese Diabetic Mice by Continuous Administration of FTY720, 2005, 79:1051-1055.
Nofer et al., "FTY720, a Synthetic Sphingosine 1 Phosphate Analogue, Inhibits Development of Atherosclerosis in Low-Density Lipoprotein Receptor Deficient Mice," Circulation, 2007, 115:501-508.
Keul et al., "The Sphinogosine-1-Phosphate Analogue FTY720 Reduces Atherosclerosis in Apolipoprotein E-Deficient Mice," Arterioscler Thromb Vasc Biol., 2007, 27:607-613.
Zhang et al., "FTY720 attenuates accumulation of EMAP-II+ and MHC-II+ monocytes in early lesions of rat traumatic brain injury," J Cell Mol Med., 2007, 11(2):307-314.
Hwang et al., "FTY720, a New Immunosuppressant, Promotes Long-Term Graft Survival and Inhibits the Progression of Graft Coronary Artery Disease in a Murine Model of Cardiac Transplantation," Circulation, 1999, 100:1322-1329.
Taylor et al., "Insights into the mechanism of FTY720 and compatibility with regulatory T cells for the inhibition of graft-versus-host disease (GVHD)," Blood, 2007, 110:3480-3488.
Kaneider et al., "The immune modulator FTY720 targets sphingosine-kinase-dependent migration of human monocytes in response to amyloid beta-protein and its precursor," FASEB J, 2004, 18 pages.
Whetzel et al., "Sphingosine-1 Phosphate Prevents Monocyte/Endothelial Interactions in Type 1 Diabetic NOD Mice Through Activation of the S1P1 Receptor," Circ. Res., 2006, 99:731-739.
Bolic et al., "Sphingosine-1-Phosphate Prevents Tumor Necrosis Factor-alpha-Mediated Monocyte Adhesion to Aortic Endothelium in Mice," Arterioscler Thromb. Vasc. Biol., 2005, 25:976-981.
Brinkmann et al., "The Immune Modulator FTY720 Targets Sphingosine 1-Phosphate Receptors," J Biol. Chem., 2002, 277(24):21453-21457.
Fujino et al., "Amerlioration of Experimental Autoimmune Encephalomyelitis in Lewis Rats by FTY720 Treatment," J Pharmacol. Exp. Ther., 2003, 305(1):70-77.
Webb et al., "Sphingosine 1-phosphate receptors agonists attenuate relapsing-remitting experimental autoimmune encephalitis in SJL mice," J Neuroimmunol., 2004, 153:108-121.

(56) References Cited

OTHER PUBLICATIONS

Rausch et al., "Predictability of FTY720 Efficacy in Experimental Autoimmune Encephalomyelitis by In Vivo Macrophage Tracking: Clinical Implications for Ultrasmall Superparamagnetic Iron Oxide-Enhanced Magnetic Resonance Imaging," 2004, J Magn. Reson. Imaging, 2004, 20:16-24.
Actelion, Clinical Trials.gov, "Multicenter, Randomized, Double-blind, Placebo-controlled, Phase IIa Study to Evaluate the Efficacy, Safety, and Tolerability of ACT-128800, an S1P1 Receptor Agonist, Administered for 6 Weeks to Subjects With Moderate to Severe Chronic Plaque Psoriasis" http://clinicaltrials.gov/ct2/show/NCT00852670, 2009.
Arbiser, "Why targeted therapy hasn't worked in advanced cancer," J Clinical Invest., 117(10):2762-2765 (2007).
Biopharmatiques, "Merging Pharma and Biotech", http://www.biopharmaceutiques.com/fr/tables/clinical_studies_709.html, 2009.
Boismenu et al., "Insights from mouse models of colitis," K. Leukoc Biol, 67:267-278, 2000.
Brinkmann, "FTY720 (fingolimod) in Multiple Sclerosis: therapeutic effects in the immune and the central nervous system", British Journal of Pharmacology, 158: 1173-1182, 2009.
Buzard, Daniel J. et al., "Discovery and Characterization of Potent and Selective 4-Oxo-4-(5-(5-phenyl-1,2,4-oxadiazol-3-yl)indolin-l-yl)butanoic acids as S1P1 Receptor Agonists", Arena Pharmaceuticals, Inc., MEDI099, ACS, Mar. 2011.
Buzard et al., "Discovery and Characterization of Potent and Selective 4-Oxo-4-(5-(5-phenyl-1,2,4-oxadiazol-3-yl)indolin-l-yl)butanoic acids as S1P1 Agonists", Biorganic Med. Chem. Lett., 2011, 6013-6018.
Buzard, Daniel J. et al, "Recent Progress in the Development of Selective S1P1 Receptor Agonists for the Treatment of Inflammatory and Autoimmune Disorders", Expert Opinion, 1141-1159, 2008.
Chawla et al., "Challenges in Polymorphism of Pharmaceuticals," CRIPS, Jan.-Mar. 2004, vol. 5, No. 1, 4 pages.
Ronald Hoffman, M.D., "Crohns disease and ulcerative colitis," Sep. 1995, http://www.drhoffman.com/page.cfm/171, 5 pages.
Collier et al, "Radiosynthesis and In-vivo Evaluation of the Psuedopeptide 8-Opioid Antagonist [125I]-ITIPP(Ψ)," J. Labeled Compd. Radiopharm., 1999, 42, S264-S266.
Fischer et al., "Targeting receptor tyrosine kinase signaling in small cell lung cancer (SCLC): What have we learned so far?" Cancer Treatment Revs., 2007, 33:391-406.
Gabriel et al, ASSAY and Drug Development Technologies, 1:291-303, 2003.
Golub et al., "Molecular Classification of Cancer: Class Discovery and Class Prediction by Gene Expression Monitoring," Science, 1999, 286:531-537.
Gottlieb, et al., "NMR Chemical Shifts of Common Laboratory Solvents as trace Impurities," *J. Org. Chem.* 1997, 62, 7512-7515.
Griesser, "The Importance of Solvates" in Polymorphism in the Pharmaceutical Industry, 211-233 (Rolf Hilfiker, ed., 2006).
Han et al., "Discovery of 2-(7-(5-phenyl-1,2,4-oxadiazol-3-yl)-1,2,3,4-tetrahydrocyclopenta[b]indol-3-yl)acetic acids: Potent and Selective Sphingosine-l-phosphate (S1P1) Receptor Agonists", Arena Pharmaceuticals, Inc., MEDI098, ACS Poster, Mar. 2011.
Jones, "Discovery of Potent and Selective Sphingosine-l-Phosphate 1 (S1P1) Receptor Agonists", CHI $6^{th}$ Annual Drug Discovery Chemistry, San Diego, CA, Apr. 12, 2011.
Jones, Robert M., "Discovery of Potent and Selective Sphingosine-l-Phosphate 1(S1P1) Receptor Agonists", CHI 6Annual Discovery on Target, Boston, MA, Nov. 3, 2011.
Kawasaki, Andrew et al., "Discovery and Characterization of 2-(7-(5-phenyl-1,2,4-oxadiazol-3-y1)-2,3-dihydro-1H-pyrrolo[1,2-a]indol-1-yl)acetic acid Derivatives as Potent & Selective Human S1P1 Receptor Agonists", Arena Pharmaceuticals, Inc., MEDI254, ACS, Mar. 2011.
Lala et al., "Role of nitric oxide in tumor progression: Lessons from experimental tumors," Cancer Metastasis Rev., 1998, 17:91-106.
Le Bas, et al, "Radioiodinated Analogs of EP 00652218 for the Exploration of the Tachykinin NK1 Receptor by Spect," J. Labeled Compl. Radiopharm. 2001, 44, S280-S282.
Madhusudan et al., "Tyrosine kinase inhibitors in cancer therapy," Clinical Biochem., 2004, 37:618-635.
Morissette, et al., "High-Throughput Crystallization: Polymorphs, Salts, Co-Crystals and Solvates", Adv. Drug Delivery Rev., 56:275-300 (2004).
Neurath et al., "Antibodies to Interleukin 12 Abrogate Established Experimental Colitis in Mice," J. Exp. Med, 182:1281-1290, 1995.
Newman et al., "Solid-state analysis of active pharmaceutical ingredient in drug products," DDT, Oct. 2003, 8(19):898-905.
Okayasu et al, "A Novel Method in the Induction of Reliable Experimental Acute and Chronic Ulcerative Colitis in Mice," Gastroenterology, 98:694-702, 1990.
Pheilschifter et al., "Treatment with immunomodulator FTY720 does not promote spontaneous bacterial infections after experimental stroke mice," Experimental Translational Stroke Med., 2011, 3, 6 pages.
Rheumatoid Arthritis Health Center—Most Common Types of Arthritis, WebMD, http://www.webmd.com/rheumatoid-arthritis/guide/most-common-arthritis-types, 2012, 2 pages.
Stahly, "Diversity in Single- and Multiple-Component Crystals. The Search for and Prevalence of Polymorphs and Cocrystals," Crystal Growth & Design (2007), 7(6), 1007-1026.
Storey, et al., "Automation of Solid Form Screening Procedures in the Pharmaceutical Industry—How to Avoid the Bottlenecks", *Crystallography Reviews*, 10(1):45-46 (2004).
Villullas et al, "Characterisation of a Sphingosine 1-Phosphate-Activated Ca2+ Signaling Pathway in Human Neuroblastoma Cells," J. Neurosci. Res, 73:215-226, 2003.
Avoiding Fatal Responses to Flu Infection, ScienceDaily, http://www.sciencedaily.com/releases/2011/09/110915134410.htm, Sep. 15, 2011, 2 pages.
Vippagunta, et al., "Crystalline Solids," *Adv. Drug Delivery Rev.*, 48:3-26 (2001).
Zhu et al, "Synthesis and Mode of Action of 125I-and 3H- Labeled Thieno[2,3-c]pyridine Antagonists of Cell Adhesion Molecule Expression," J. Org. Chem., 2002, 67, 943-948.
"Schafiee et al., ""An efficent enzyme-catalyzed kinetic resolution: large-scale preparation of an enantiomerically pure indole-ethyl ester derivative, a key component for the synthesis of a prostaglandin D2 receptor antagonist, an anti-allergic rhinitis drug candidate," *Tetrahedron: Asymmetry*, 2005, 16:3094-3098".

PXRD Diffractogram
(L-Arginine salt of (R)-2-(7-(4-cyclopentyl-3-(trifluoromethyl)benzyloxy)-1,2,3,4-tetrahydrocyclopenta[b]indol-3-yl)acetic acid as prepared in Example 7)

PROCESSES FOR THE PREPARATION OF (R)-2-(7-(4-CYCLOPENTYL-3-(TRIFLUOROMETHYL)BENZYLOXY)-1,2,3,4-TETRAHYDROCYCLOPENTA[B]INDOL-3-YL)ACETIC ACID AND SALTS THEREOF

This application is a §371 National Stage Application of PCT/US2011/000153, filed Jan. 27, 2011, which claims the benefit of priority of U.S. Provisional Application 61/336,835, filed Jan. 27, 2010, each of which is incorporated herein by reference in its entirety.

FIELD OF THE INVENTION

The present invention relates to processes and intermediates useful in the preparation of (R)-2-(7-(4-cyclopentyl-3-(trifluoromethyl)benzyloxy)-1,2,3,4-tetrahydrocyclopenta[b]indol-3-yl)acetic acid of Formula (Ia) or salts thereof, an S1P1 receptor modulator that is useful in the treatment of S1P1 receptor-associated disorders, for example, diseases and disorders mediated by lymphocytes, transplant rejection, autoimmune diseases and disorders, inflammatory diseases and disorders (e.g., acute and chronic inflammatory conditions), cancer, and conditions characterized by an underlying defect in vascular integrity or that are associated with angiogenesis such as may be pathologic (e.g., as may occur in inflammation, tumor development and atherosclerosis).

BACKGROUND OF THE INVENTION

S1P1 receptor agonists have been shown to possess at least immunosuppressive, anti-inflammatory, and/or hemostatic activities, e.g. by virtue of modulating leukocyte trafficking, sequestering lymphocytes in secondary lymphoid tissues, and/or enhancing vascular integrity. Accordingly, S1P1 receptor agonists can be useful as immunosuppressive agents for at least autoimmune diseases and disorders, inflammatory diseases and disorders (e.g., acute and chronic inflammatory conditions), transplant rejection, cancer, and/or conditions that have an underlying defect in vascular integrity or that are associated with angiogenesis such as may be pathologic (e.g., as may occur in inflammation, tumor development, and atherosclerosis) with fewer side effects such as the impairment of immune responses to systemic infection.

The sphingosine-1-phosphate (S1P) receptors 1-5 constitute a family of G protein-coupled receptors containing a seven-transmembrane domain. These receptors, referred to as S1P1 to S1P5 (formerly termed endothelial differentiation gene (EDG) receptor-1, -5, -3, -6, and -8, respectively; Chun et al., *Pharmacological Reviews*, 54:265-269, 2002), are activated via binding by sphingosine-1-phosphate, which is produced by the sphingosine kinase-catalyzed phosphorylation of sphingosine. S1P1, S1P4, and S1P5 receptors activate Gi but not Gq, whereas S1P2 and S1P3 receptors activate both Gi and Gq. The S1P3 receptor, but not the S1P1 receptor, responds to an agonist with an increase in intracellular calcium.

In view of the growing demand for S1P1 agonists useful in the treatment of S1P1 receptor-associated disorders, the compound (R)-2-(7-(4-cyclopentyl-3-(trifluoromethyl)benzyloxy)-1,2,3,4-tetrahydrocyclopenta[b]indol-3-yl)acetic acid of Formula (Ia):

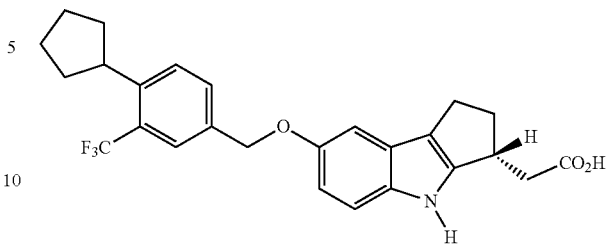

has emerged as an important new compound, see PCT patent application, Serial No. PCT/US2009/004265 hereby incorporated by reference in its entirety. Accordingly, new and efficient routes leading to (R)-2-(7-(4-cyclopentyl-3-(trifluoromethyl)benzyloxy)-1,2,3,4-tetrahydrocyclopenta[b]indol-3-yl)acetic acid of Formula (Ia), salts, and intermediates related thereto are needed. The processes and compounds described herein help meet these and other needs.

SUMMARY OF THE INVENTION

The processes and intermediates of the present invention are useful in preparing (R)-2-(7-(4-cyclopentyl-3-(trifluoromethyl)benzyloxy)-1,2,3,4-tetrahydrocyclopenta[b]indol-3-yl)acetic acid of Formula (Ia). (R)-2-(7-(4-cyclopentyl-3-(trifluoromethyl)benzyloxy)-1,2,3,4-tetrahydrocyclopenta[b]indol-3-yl)acetic acid of Formula (Ia) is useful in the treatment of S1P1 receptor-associated disorders, such as, psoriasis and multiple sclerosis, and is disclosed in PCT patent application, Serial No. PCT/US2009/004265 hereby incorporated by reference in its entirety.

One aspect of the present invention relates to processes and intermediates that are useful in preparing the L-arginine salt of (R)-2-(7-(4-cyclopentyl-3-(trifluoromethyl)benzyloxy)-1,2,3,4-tetrahydrocyclopenta[b]indol-3-yl)acetic acid, the salt which was found to be surprisingly and unexpectedly different from what was previously reported in PCT patent application, Serial No. PCT/US2009/004265.

The present invention provides, inter alia, processes for preparing an L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia):

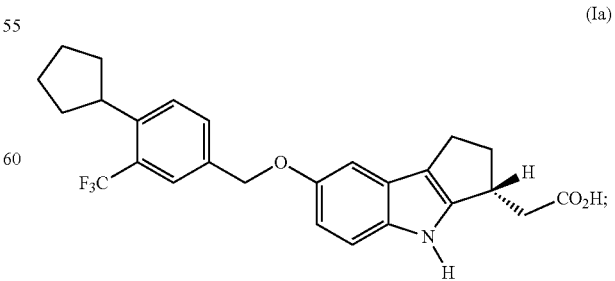

comprising the following steps:

a) cross-coupling bromopentane with a compound of Formula (IIa):

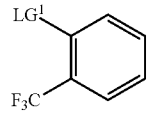

(IIa)

wherein LG¹ is selected from the group consisting of Cl, Br, I, TfO, and TsO, in the presence of:
i) elemental magnesium;
ii) an Fe catalyst;
iii) a cross-coupling-step solvent; and
iv) a cross-coupling agent;

to form 1-cyclopentyl-2-(trifluoromethyl)benzene (Formula (IIb)):

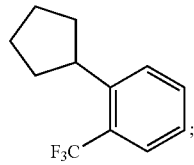

(IIb)

b) reacting 1-cyclopentyl-2-(trifluoromethyl)benzene (Formula (IIb)) with 1,3,5-trioxane in the presence of an acid and a chlorinating agent, to form 4-(chloromethyl)-1-cyclopentyl-2-(trifluoromethyl)benzene of Formula (IIc):

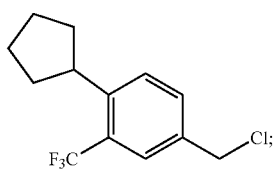

(IIc)

c) reacting a compound of Formula (IIg):

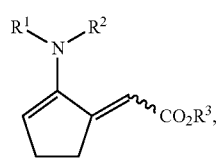

(IIg)

wherein $R^1$ and $R^2$ are each independently $C_1$-$C_6$ alkyl, or $R^1$ and $R^2$ together with the nitrogen atom to which they are both bonded form a 5-member or 6-member heterocyclic ring, and $R^3$ is $C_1$-$C_6$ alkyl;

with a compound of Formula (IIh) or a salt thereof,

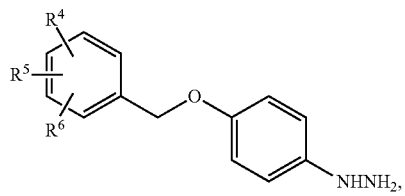

(IIh)

wherein $R^4$, $R^5$, and $R^6$ are each selected independently from the group consisting of H, $C_1$-$C_4$ alkyl, $C_1$-$C_4$ alkoxy, halogen, $C_1$-$C_4$ haloalkyl, $C_1$-$C_4$ haloalkoxy, and nitro; in the presence of an indole-forming acid, to form a compound of Formula (IIi):

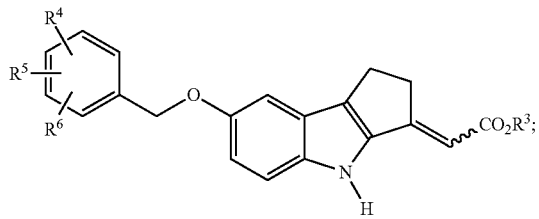

(IIi)

d) reducing the compound of Formula (IIi) in the presence of a reducing-step agent, and a reducing-step catalyst, to form a compound of Formula (IIj) or a salt thereof:

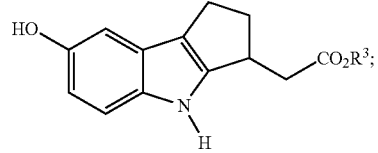

(IIj)

e) alkylating the compound of Formula (IIj) or a salt thereof, with the 4-(chloromethyl)-1-cyclopentyl-2-(trifluoromethyl)benzene (Formula (IIc)), in the presence of an alkylating-step base, and an alkylating-step solvent to form a compound of Formula (IIk):

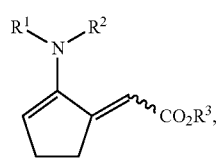

(IIk)

f) hydrolyzing the compound of Formula (IIk) in the presence of a lipase and a hydrolyzing-step solvent to form (R)-2-(7-(4-cyclopentyl-3-(trifluoromethyl)benzyloxy)-1,2,3,4-tetrahydrocyclopenta[b]indol-3-yl)acetic acid of Formula (Ia):

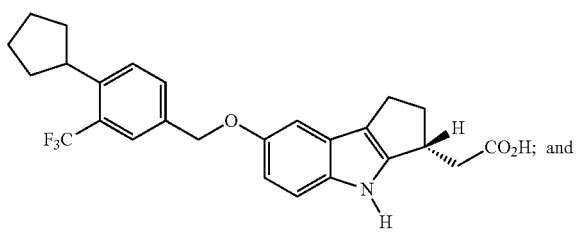

(Ia)

g) contacting (R)-2-(7-(4-cyclopentyl-3-(trifluoromethyl)benzyloxy)-1,2,3,4-tetrahydrocyclopenta[b]indol-3-yl)acetic acid (Formula (Ia)) with L-arginine or a salt thereof, in the presence of a contacting-step solvent and $H_2O$ to form the L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia).

The present invention further provides processes for preparing an L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia):

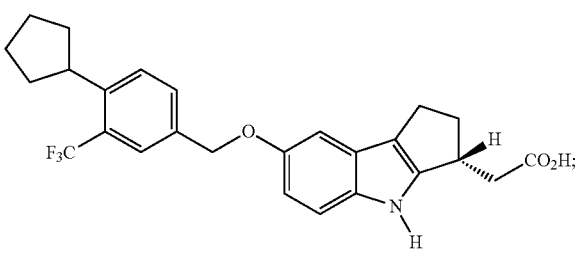

(Ia)

comprising the following steps:

a) hydrolyzing the compound of Formula (IIk):

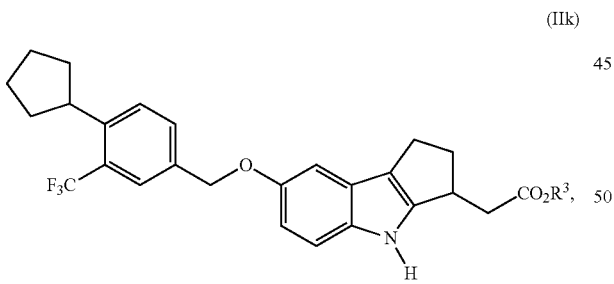

(IIk)

wherein $R^3$ is $C_1$-$C_6$ alkyl;
in the presence of a lipase and a hydrolyzing-step solvent to form (R)-2-(7-(4-cyclopentyl-3-(trifluoromethyl)benzyloxy)-1,2,3,4-tetrahydrocyclopenta[b]indol-3-yl)acetic acid of Formula (Ia); and b) contacting (R)-2-(7-(4-cyclopentyl-3-(trifluoromethyl)benzyloxy)-1,2,3,4-tetrahydrocyclopenta[b]indol-3-yl)acetic acid (Formula (Ia)) with L-arginine or a salt thereof, in the presence of a contacting-step solvent and $H_2O$ to form the L-arginine salt of (R)-2-(7-(4-cyclopentyl-3-(trifluoromethyl)benzyloxy)-1,2,3,4-tetrahydrocyclopenta[1]]indol-3-yl)acetic acid of Formula (Ia).

The present invention further provides processes for preparing (R)-2-(7-(4-cyclopentyl-3-(trifluoromethyl)benzyloxy)-1,2,3,4-tetrahydrocyclopenta[b]indol-3-yl)acetic acid of Formula (Ia):

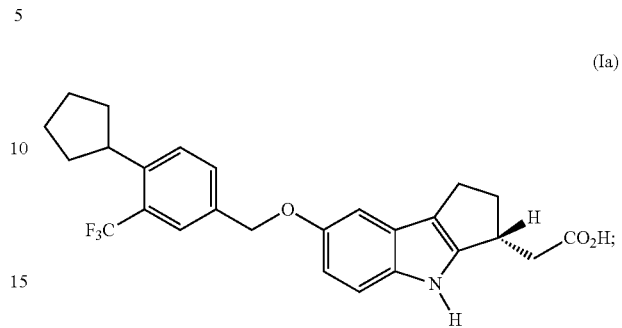

(Ia)

comprising the step of hydrolyzing the compound of Formula (IIk):

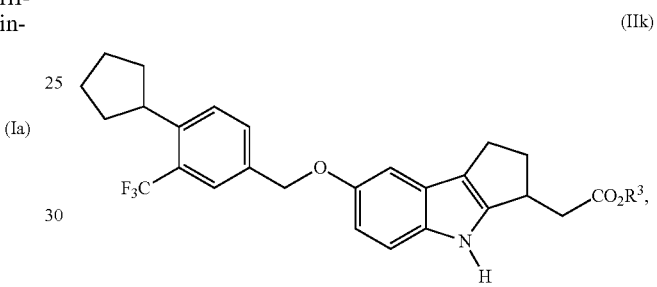

(IIk)

wherein $R^3$ is $C_1$-$C_6$ alkyl;
in the presence of a lipase and a hydrolyzing-step solvent to form (R)-2-(7-(4-cyclopentyl-3-(trifluoromethyl)benzyloxy)-1,2,3,4-tetrahydrocyclopenta[b]indol-3-yl)acetic acid of Formula (Ia).

The present invention further provides processes for preparing a compound of Formula (IIk):

(IIk)

wherein $R^3$ is $C_1$-$C_6$ alkyl;
comprising the step of alkylating a compound of Formula (IIj):

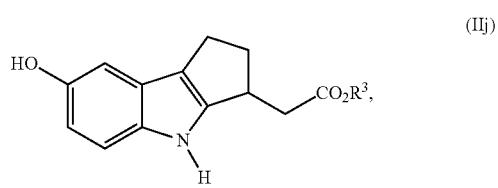

(IIj)

with 4-(chloromethyl)-1-cyclopentyl-2-(trifluoromethyl) benzene (Formula (IIc)):

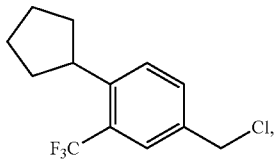
(IIc)

in the presence of an alkylating-step base, and an alkylating-step solvent to form the compound of Formula (IIk), provided that the alkylating-step solvent is other than dimethylformamide (DMF), or dimethylacetamide (DMA).

The present invention further provides processes for preparing a compound of Formula (IIj):

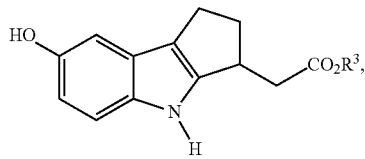
(IIj)

wherein $R^3$ is $C_1$-$C_6$ alkyl;
comprising the step of reducing a compound of Formula (IIi):

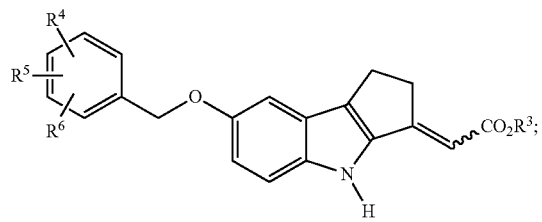
(IIi)

wherein $R^3$ is $C_1$-$C_6$ alkyl; and $R^4$, $R^5$, and $R^6$ are each selected independently from the group consisting of H, $C_1$-$C_4$ alkyl, $C_1$-$C_4$ alkoxy, halogen, $C_1$-$C_4$ haloalkyl, $C_1$-$C_4$ haloalkoxy, and nitro;
in the presence of a reducing-step agent, and a reducing-step catalyst, to form the compound of Formula (IIj).

The present invention further provides processes for preparing a compound of Formula (IIi):

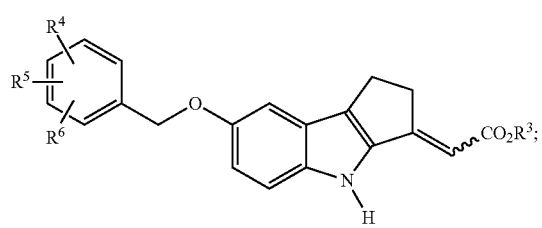
(IIi)

wherein $R^3$ is $C_1$-$C_6$ alkyl; and $R^4$, $R^5$, and $R^6$ are each selected independently from the group consisting of H, $C_1$-$C_4$ alkyl, $C_1$-$C_4$ alkoxy, halogen, $C_1$-$C_4$ haloalkyl, $C_1$-$C_4$ haloalkoxy, and nitro;
comprising the step of reacting a compound of Formula (IIg):

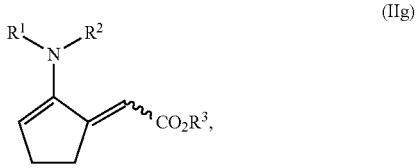
(IIg)

wherein $R^1$ and $R^2$ are each independently $C_1$-$C_6$ alkyl, or $R^1$ and $R^2$ together with the nitrogen atom to which they are both bonded form a 5-member or 6-member heterocyclic ring;
with a compound of Formula (IIh) or a salt thereof,

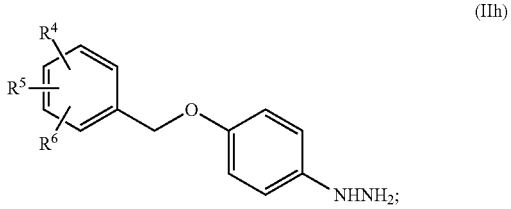
(IIh)

in the presence of an indole-forming acid, to form a compound of Formula (IIi).

The present invention further provides processes for preparing 4-(chloromethyl)-1-cyclopentyl-2-(trifluoromethyl) benzene of Formula (IIc):

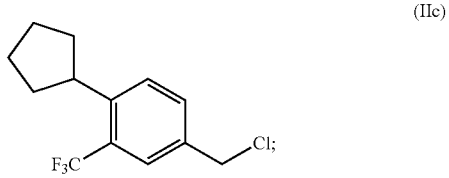 [SMILES: FC(F)(F)c1cc(CCl)ccc1C1CCCC1]
(IIc)

comprising the step of reacting 1-cyclopentyl-2-(trifluoromethyl)benzene (Formula (IIb)):

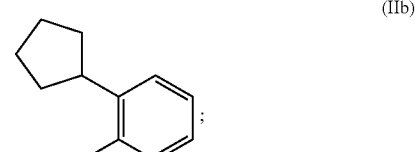
(IIb)

with 1,3,5-trioxane in the presence of an acid and a chlorinating agent, to form 4-(chloromethyl)-1-cyclopentyl-2-(trifluoromethyl)benzene of Formula (IIc).

The present invention further provides processes for preparing 1-cyclopentyl-2-(trifluoromethyl)benzene (Formula (IIb)):

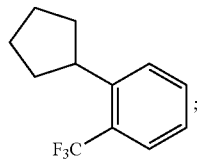
(IIb)

comprising the step of cross-coupling bromopentane with a compound of Formula (IIa):

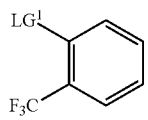
(IIa)

wherein $LG^1$ is selected from the group consisting of Cl, Br, I, TfO, and TsO, in the presence of:

i) elemental magnesium;
ii) an Fe catalyst;
iii) a cross-coupling-step solvent; and
iv) a cross-coupling agent;

to form 1-cyclopentyl-2-(trifluoromethyl)benzene.

The present invention further provides pharmaceutical compositions comprising (R)-2-(7-(4-cyclopentyl-3-(trifluoromethyl)benzyloxy)-1,2,3,4-tetrahydrocyclopenta[b]indol-3-yl)acetic acid of Formula (Ia), or a salt thereof:

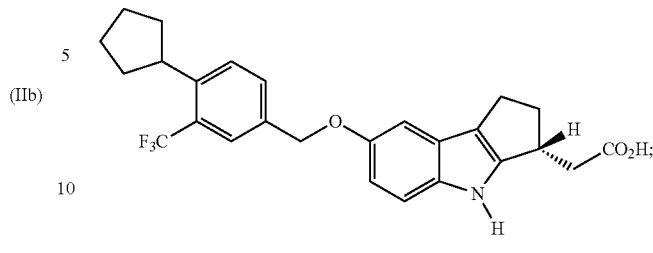
(Ia)

and a pharmaceutically acceptable carrier, wherein (R)-2-(7-(4-cyclopentyl-3-(trifluoromethyl)benzyloxy)-1,2,3,4-tetrahydrocyclopenta[b]indol-3-yl)acetic acid of Formula (Ia) is prepared according to any of the processes described herein.

The present invention further provides processes of preparing a pharmaceutical composition comprising admixing (R)-2-(7-(4-cyclopentyl-3-(trifluoromethyl)benzyloxy)-1,2,3,4-tetrahydrocyclopenta[b]indol-3-yl)acetic acid of Formula (Ia), or a salt thereof:

and a pharmaceutically acceptable carrier, wherein (R)-2-(7-(4-cyclopentyl-3-(trifluoromethyl)benzyloxy)-1,2,3,4-tetrahydrocyclopenta[b]indol-3-yl)acetic acid of Formula (Ia) is prepared according to any of the processes described herein.

The present invention further provides pharmaceutical compositions comprising an L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia):

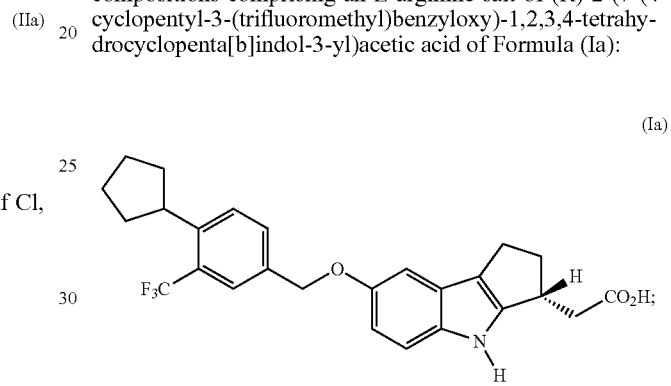
(Ia)

(Ia)

and a pharmaceutically acceptable carrier, wherein the L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia) is prepared according to any of the processes described herein.

The present invention further provides processes of preparing a pharmaceutical composition comprising admixing an L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia):

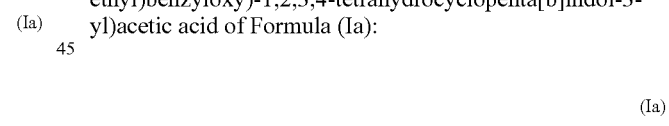
(Ia)

and a pharmaceutically acceptable carrier, wherein the L-arginine salt of (R)-2-(7-(4-cyclopentyl-3-(trifluoromethyl)benzyloxy)-1,2,3,4-tetrahydrocyclopenta[1])indol-3-yl)acetic acid of Formula (Ia) is prepared according to any of the processes described herein.

The present invention further provides compounds represented by any of the formulae described herein.

The present invention further provides compounds represented by any of the formulae described herein for use in a process for preparing a pharmaceutical composition for treating an S1P1 receptor-associated disorder in an individual.

The present invention further provides compounds represented by any of the formulae described herein prepared according to any of the processes described herein.

The present invention further provides compounds represented by any of the formulae described herein prepared according to any of the processes described herein, for use in a process for preparing a pharmaceutical composition for treating an S1P1 receptor-associated disorder in an individual.

These and other aspects of the invention disclosed herein will be set forth in greater detail as the patent disclosure proceeds.

DETAILED DESCRIPTION

Figure 1:
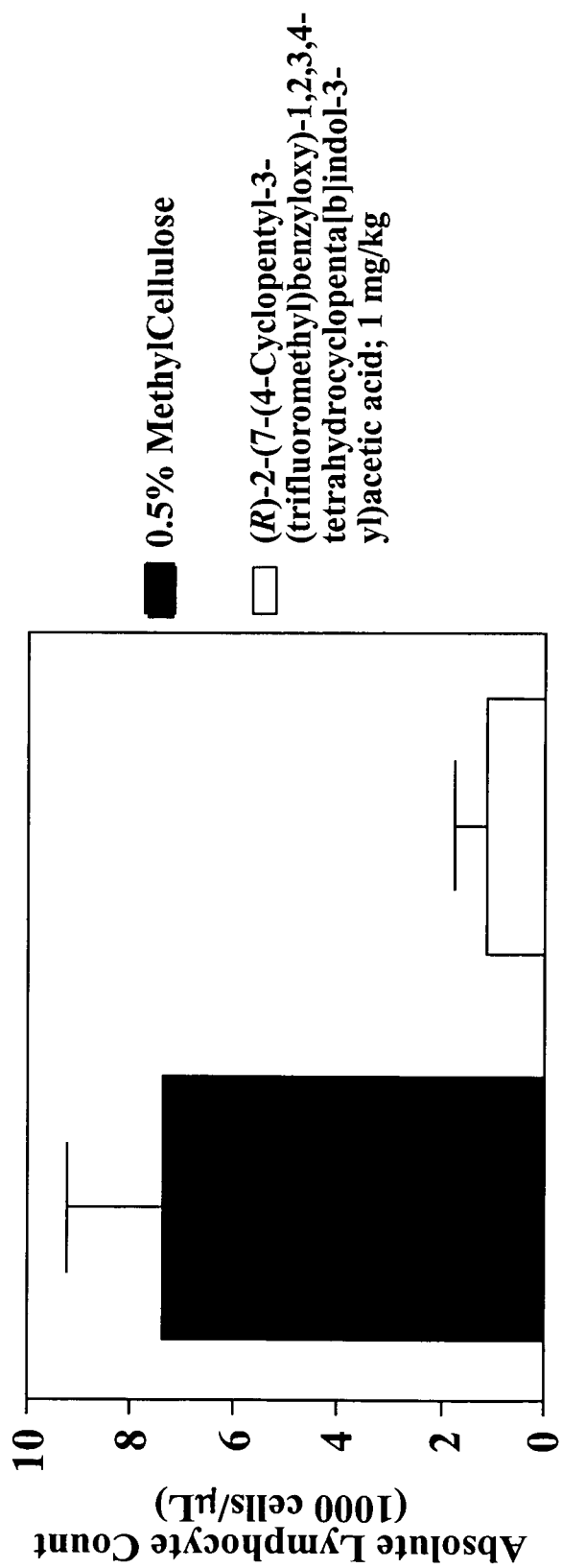
FIG. 1 shows the effect of (R)-2-(7-(4-cyclopentyl-3-(trifluoromethyl)benzyloxy)-1,2,3,4-tetrahydrocyclopenta[b]indol-3-yl)acetic acid (Compound of Formula (Ia)) in the Peripheral Lymphocyte Lowering (PLL) Assay after a 1 mg/kg oral dose in BALB/c mice.

The processes and intermediates of the present invention are useful in preparing (R)-2-(7-(4-cyclopentyl-3-(trifluoromethyl)benzyloxy)-1,2,3,4-tetrahydrocyclopenta[1]indol-3-yl)acetic acid of Formula (Ia) and salts thereof. (R)-2-(7-(4-cyclopentyl-3-(trifluoromethyl)benzyloxy)-1,2,3,4-tetrahydrocyclopenta[b]indol-3-yl)acetic acid of Formula (Ia) is useful in the treatment of S1P1 receptor-associated disorders as described herein and as described in the PCT patent application, Serial No. PCT/US2009/004265 hereby incorporated by reference in its entirety.

DEFINITIONS

For clarity and consistency, the following definitions will be used throughout this patent document.

The term "$C_1$-$C_4$ alkoxy" is intended to mean a $C_1$-$C_4$ alkyl radical, as defined herein, attached directly to an oxygen atom. Some embodiments are 1 to 3 carbons and some embodiments are 1 or 2 carbons. Examples include methoxy, ethoxy, n-propoxy, isopropoxy, n-butoxy, tert-butoxy, isobutoxy, sec-butoxy and the like.

The term "$C_1$-$C_6$ alkyl" is intended to mean a straight or branched carbon radical containing 1 to 6 carbons. Some embodiments are 1 to 5 carbons, some embodiments are 1 to 4 carbons, some embodiments are 1 to 3 carbons and some embodiments are 1 or 2 carbons. Examples of an alkyl include, but are not limited to, methyl, ethyl, n-propyl, isopropyl, n-butyl, sec-butyl, isobutyl, tert-butyl, pentyl, isopentyl, tert-pentyl, neo-pentyl, 1-methylbutyl [i.e., —CH(CH$_3$)CH$_2$CH$_2$CH$_3$], 2-methylbutyl [i.e., —CH$_2$CH(CH$_3$)CH$_2$CH$_3$], n-hexyl and the like.

The term "$C_1$-$C_4$ haloalkoxy" is intended to mean a $C_1$-$C_4$ haloalkyl, as defined herein, which is directly attached to an oxygen atom. Examples include, but are not limited to, difluoromethoxy, trifluoromethoxy, 2,2,2-trifluoroethoxy, pentafluoroethoxy and the like.

The term "$C_1$-$C_4$ haloalkyl" is intended to mean an $C_1$-$C_4$ alkyl group, defined herein, wherein the alkyl is substituted with between one halogen up to fully substituted wherein a fully substituted $C_1$-$C_6$ haloalkyl can be represented by the formula $C_nL_{2n+1}$ wherein L is a halogen. and "n" is 1, 2, 3, or 4. When more than one halogen is present, the halogens may be the same or different and selected from the group consisting of fluoro, chloro, bromo or iodo, preferably fluoro. Some embodiments are 1 to 4 carbons, some embodiments are 1 to 3 carbons and some embodiments are 1 or 2 carbons. Examples of haloalkyl groups include, but are not limited to, fluoromethyl, difluoromethyl, trifluoromethyl, chlorodifluoromethyl, 2,2,2-trifluoroethyl, pentafluoroethyl, and the like.

The term "halogen" or "halo" is intended to mean a fluoro, chloro, bromo, or iodo group.

The term "nitro" is intended to mean a radical of the formula: —NO$_2$.

The term "$C_1$-$C_4$ alkylalcohol" is intended to mean a straight or branched carbon alkane containing 1 to 4 carbons wherein one hydrogen has been replaced with an OH group. Examples of a $C_1$-$C_4$ alkylalcohol include, but are not limited to, methanol, ethanol, isopropanol, n-butanol, tert-butanol, and the like.

The term "agonists" is intended to mean moieties that interact and activate a receptor, such as the S1P1 receptor, and initiate a physiological or pharmacological response characteristic of that receptor, for example, moieties that activate the intracellular response upon binding to the receptor, or enhance GTP binding to membranes.

The term "hydrate" as used herein means a compound, including but not limited to a pharmaceutically acceptable salt of a compound, that further includes a stoichiometric or non-stoichiometric amount of water bound by non-covalent intermolecular forces.

The term "individual" is intended to mean any animal, including mammals, preferably mice, rats, other rodents, rabbits, dogs, cats, swine, cattle, sheep, horses, or primates and most preferably humans.

The term "pharmaceutical composition" is intended to mean a composition comprising at least one active ingredient; including but not limited to Compound of Formula (Ia) and pharmaceutically acceptable salts, solvates and hydrates thereof, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The term "solvate" as used herein means a compound, including but not limited to a pharmaceutically acceptable salt of a compound, that further includes a stoichiometric or non-stoichiometric amount of a solvent bound by non-covalent intermolecular forces. Preferred solvents are volatile, non-toxic, and/or acceptable for administration to humans in trace amounts.

The term "treatment" or "treating" as used herein includes one or more of the following:

(1) prevention of a disease, for example, prevention of a disease, condition or disorder in an individual that may be predisposed to the disease, condition or disorder but does not yet experience or display the pathology or symptomatology of the disease;

(2) inhibition of a disease, for example, inhibition of a disease, condition or disorder in an individual that is experiencing or displaying the pathology or symptomatology of the disease, condition or disorder (i.e., arresting further development of the pathology and/or symptomatology); and (3) amelioration of a disease, for example, amelioration of a disease, condition or disorder in an individual that is experiencing or displaying the pathology or symptomatology of the disease, condition or disorder (i.e., reversing the pathology and/or symptomatology).

Whether an individual is in need of treatment is a judgment made by a caregiver (e.g. nurse practitioner, physician, physician assistant, nurse, etc. in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by Compound of Formula (Ia) and pharmaceutically acceptable salts, solvates and hydrates thereof. Accordingly, Compound of Formula (Ia) and pharmaceutically acceptable salts, solvates and hydrates thereof can be used in a protective or preventive manner; or Compound of Formula (Ia) and pharmaceutically acceptable salts, solvates and hydrates thereof can be used to alleviate, inhibit or ameliorate a disease, condition or disorder.

PROCESSES OF THE INVENTION

The present invention is directed, inter alia, to processes and intermediates useful in the preparation of (R)-2-(7-(4-cyclopentyl-3-(trifluoromethyl)benzyloxy)-1,2,3,4-tetrahydrocyclopenta[b]indol-3-yl)acetic acid of Formula (Ia) and/or salts related thereto.

Representative cross-coupling and chloromethylation steps, and intermediates of Formulae (IIa), (IIb), and (IIc) of the present invention are provided below in Scheme I.

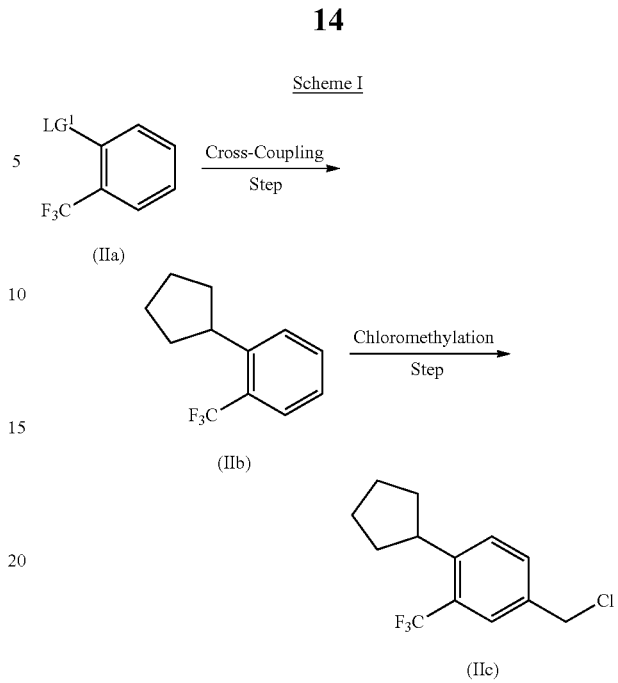

Representative enamine step and reaction with compounds of Formula (IIf), and intermediates of Formulae (IId), (IIe), (IIf), and (IIg) of the present invention are provided below in Scheme II.

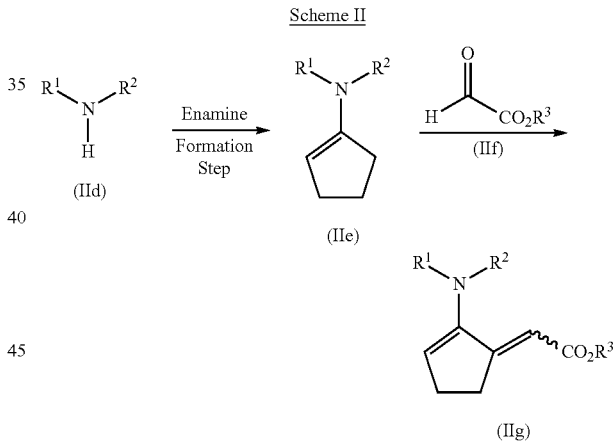

Representative indole forming step and intermediates of Formulae (IIg), (IIh), and (IIi) of the present invention are provided below in Scheme III.

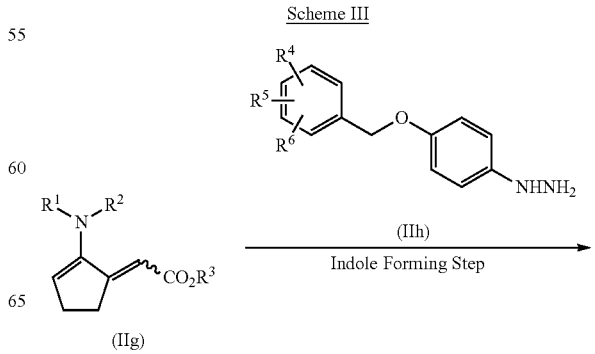

-continued

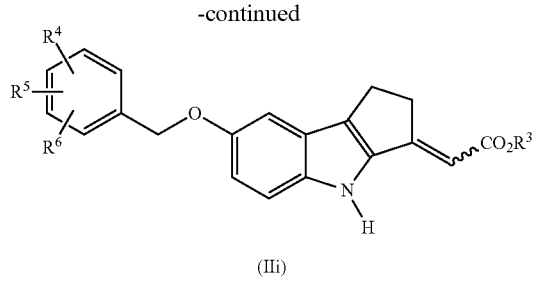

(IIi)

Representative reduction step and intermediates of Formulae (IIi) and (IIj) of the present invention are provided below in Scheme IV.

Scheme IV

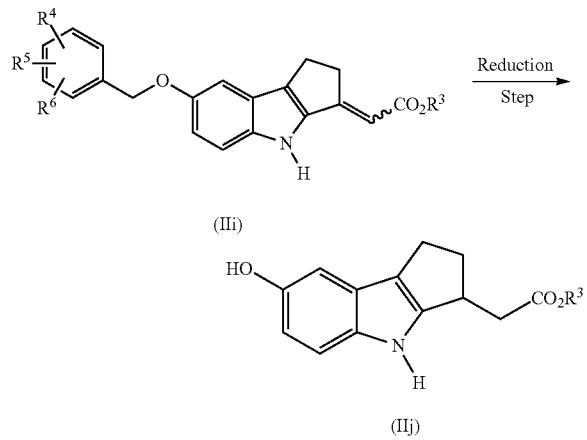

Representative alkylation step and intermediates of Formulae (IIj) and (IIk) of the present invention are provided below in Scheme V.

Scheme V

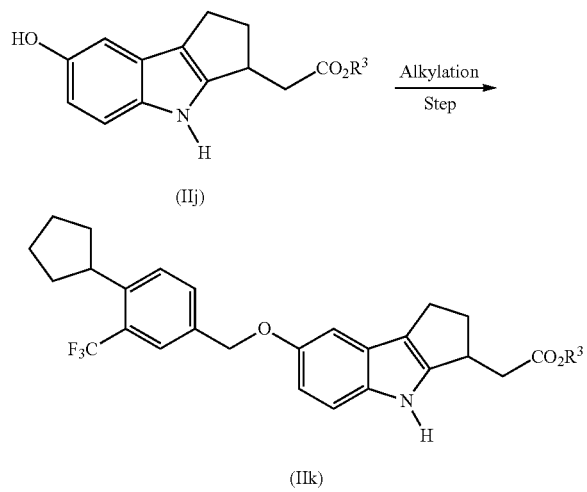

Representative hydrolysis step, intermediates of Formulae (IIk), and compound of Formula (Ia) of the present invention are provided below in Scheme VI.

Scheme VI

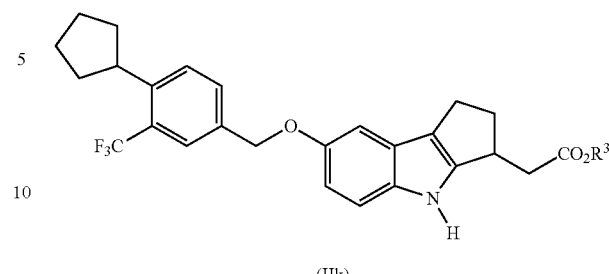

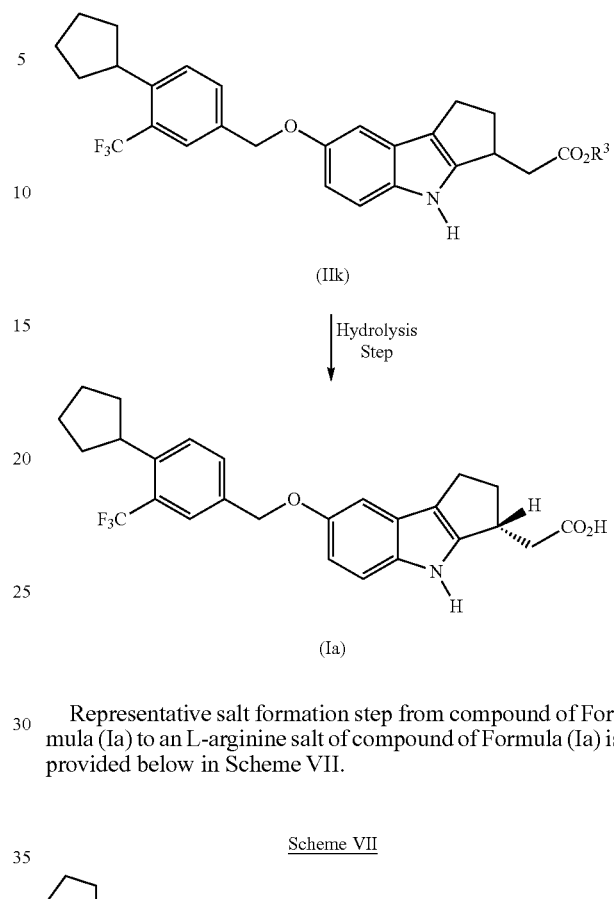

Representative salt formation step from compound of Formula (Ia) to an L-arginine salt of compound of Formula (Ia) is provided below in Scheme VII.

Scheme VII

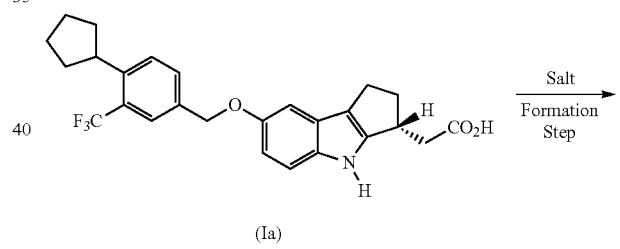

An L-Arg salt of Compound (Ia)

One aspect of the present invention pertains to processes, such as those exemplified by Schemes I, II, III, IV, V, VI, and VII, (supra), that involve Compounds (Ia), (IIa), (IIb), (IIc), (IId), (IIe), (IIg), (IIh), (IIi), (IIj), and (IIk).

One aspect of the present invention pertains to intermediates, Compounds (Ia), (IIa), (IIb), (IIc), (IId), (IIe), (IIf), (IIg), (IIh), (Iii), (IIj), and (IIk), as exemplified in Schemes I, II, III, IV, V, VI, and VII (supra), useful in the preparation of Compound of Formula (Ia) and/or a salt related thereto, for example, an L-arginine salt of Compound of formula (Ia).

One aspect of the present invention pertains to intermediates as exemplified in Schemes I, II, III, IV, V, VI, and VII (supra), that involve Compounds of formulae (Ia), (IIa), (IIb), (IIc), (IId), (IIe), (IIf), (IIg), (IIh), (IIi), (IIj), and (IIk), wherein:

$LG^1$ is selected from the group consisting of Cl, Br, I, TfO, and TsO;

$R^1$ and $R^2$ are each independently $C_1$-$C_6$ alkyl, or $R^1$ and $R^2$ together with the nitrogen atom to which they are both bonded form a 5-member or 6-member heterocyclic ring;

$R^3$ is $C_1$-$C_6$ alkyl; and $R^4$, $R^5$, and $R^6$ are each selected independently from the group consisting of H, $C_1$-$C_4$ alkyl, $C_1$-$C_4$ alkoxy, halogen, $C_1$-$C_4$ haloalkyl, $C_1$-$C_4$ haloalkoxy, and nitro.

In some embodiments, $LG^1$ is TfO or TsO.

In some embodiments, $LG^1$ is TfO.

In some embodiments, $LG^1$ is selected from the group consisting of Cl, Br, and I.

In some embodiments, $LG^1$ is Br or I.

In some embodiments, $LG^1$ is Br.

In some embodiments, $R^1$ and $R^2$ are each independently $C_1$-$C_6$ alkyl.

In some embodiments, $R^1$ and $R^2$ together with the nitrogen atom to which they are both bonded form a 5-member or 6-member heterocyclic ring.

In some embodiments, $R^1$ and $R^2$ together with the nitrogen atom to which they are both bonded form a 6-member heterocyclic ring.

In some embodiments, $R^1$ and $R^2$ together with the nitrogen atom to which they are both bonded form a 5-member heterocyclic ring.

In some embodiments, $R^1$ and $R^2$ together with the nitrogen atom to which they are both bonded form a morpholinyl ring.

In some embodiments, $R^1$ and $R^2$ together with the nitrogen atom to which they are both bonded form a pyrrolidinyl ring.

In some embodiments, $R^3$ is methyl or ethyl.

In some embodiments, $R^3$ is ethyl.

In some embodiments, $R^4$, $R^5$, and $R^6$ are each selected independently from the group consisting of H, $CH_3$, $OCH_3$, $OCH_2CH_3$, F, Cl, Br, $CF_3$, $OCF_3$, and nitro.

In some embodiments, $R^4$, $R^5$, and $R^6$ are each selected independently from the group consisting of H, $CH_3$, $OCH_3$, $OCH_2CH_3$, F, Cl, $CF_3$, $OCF_3$.

In some embodiments, $R^4$, $R^5$, and $R^6$ are each selected independently from the group consisting of H and $OCH_3$.

In some embodiments, $R^4$, $R^5$, and $R^6$ are each H.

One aspect of the present invention pertains to a compound of Formula (IIi):

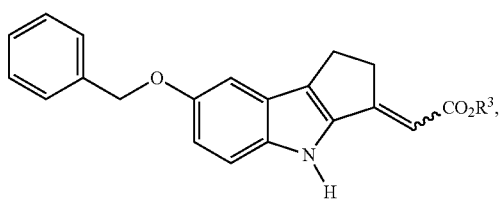

(IIi)

wherein: $R^3$ is $C_1$-$C_6$ alkyl. In some embodiments, $R^3$ is ethyl.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables (e.g., $LG^1$, $R^1$, $R^2$, $R^3$, $R^4$, $R^5$, and $R^6$) contained within the generic chemical formulae described herein are specifically embraced by the present invention just as if each and every combination was individually explicitly recited, to the extent that such combinations embrace stable compounds (i.e., compounds that can be isolated, characterized and tested for biological activity). In addition, all subcombinations of the chemical groups listed in the embodiments describing such variables, as well as all subcombinations of uses and medical indications described herein, are also specifically embraced by the present invention just as if each and every subcombination of chemical groups and subcombination of uses and medical indications was individually and explicitly recited herein.

I. Cross-Coupling Step

One aspect of the present invention pertains to processes for preparing 1-cyclopentyl-2-(trifluoromethyl)benzene of Formula (IIb):

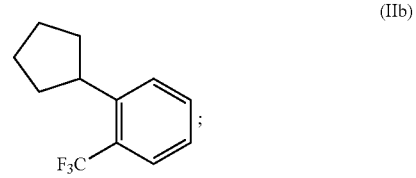 [SMILES: FC(F)(F)c1ccccc1C1CCCC1]

(IIb)

comprising the step of cross-coupling bromopentane with a compound of Formula (IIa):

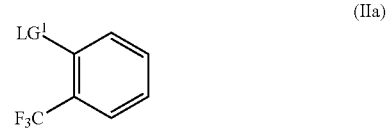

(IIa)

wherein $LG^1$ is selected from the group consisting of Cl, Br, I, TfO, and TsO, in the presence of:

i) elemental magnesium;

ii) an Fe catalyst;

iii) a cross-coupling-step solvent; and iv) a cross-coupling agent;

to form 1-cyclopentyl-2-(trifluoromethyl)benzene.

In some embodiments, $LG^1$ is TfO or TsO.

In some embodiments, $LG^1$ is TfO.

In some embodiments, $LG^1$ is selected from the group consisting of Cl, Br, and I.

In some embodiments, $LG^1$ is Br or I.

In some embodiments, $LG^1$ is Br.

In some embodiments, the elemental magnesium is in the form of magnesium turnings, magnesium ribbons, magnesium powder, or magnesium rods.

In some embodiments, the elemental magnesium is in the form of magnesium turnings.

In some embodiments, the Fe catalyst is an Fe(III) catalyst (i.e., $Fe^{+3}$).

In some embodiments, the Fe catalyst comprises $FeF_3$, $FeF_3 \cdot 3H_2O$, $FeCl_3$, $FeCl_3 \cdot 6H_2O$, $Fe(acac)_3$ [i.e., Fe(CH$_3$COCHCOCH$_3$)$_3$], or Fe(salen)Cl complex. The Fe catalyst Fe(salen)Cl complex has the following formula:

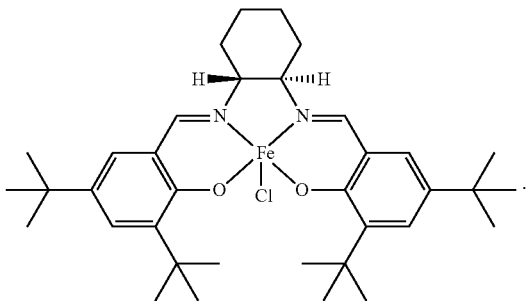

In some embodiments, the Fe catalyst comprises FeCl$_3$.

In some embodiments, the cross-coupling-step solvent comprises any suitable solvent.

In some embodiments, the cross-coupling-step solvent comprises an ethereal solvent.

In some embodiments, the cross-coupling-step solvent comprises tetrahydrofuran (THF), 2-methyl-tetrahydrofuran, diethyl ether, dibutyl ether, tert-butylmethyl ether, or tetrahydropyran.

In some embodiments, the cross-coupling-step solvent comprises tetrahydrofuran (THF).

In some embodiments, the cross-coupling agent comprises dimethylacetamide (DMA), dimethylformamide (DMF), N-methylpyrrolidinone (NMP), hexamethylphosphoric acid triamide (HMPA), 1,3-dimethyl-3,4,5,6-tetrahydro-2(1H)-pyrimidinone (DMPU), or N,N,N',N'-tetramethylethylenediamine (TMEDA).

In some embodiments, the cross-coupling agent comprises N,N,N',N'-tetramethylethylenediamine (TMEDA).

In some embodiments, the cross-coupling-step solvent comprises tetrahydrofuran (THF) and the cross-coupling agent comprises N,N,N',N'-tetramethylethylenediamine (TMEDA).

In some embodiments, the cross-coupling-step solvent is substantially free of water.

In some embodiments, the cross-coupling agent is substantially free of water.

In some embodiments, the step of cross-coupling bromopentane with a compound of Formula (IIa) is conducted under a substantially inert atmosphere.

In some embodiments, the step of cross-coupling bromopentane with a compound of Formula (IIa) is conducted under a substantially inert atmosphere comprising argon or nitrogen.

In some embodiments, the step of cross-coupling bromopentane with a compound of Formula (IIa) is conducted under a substantially inert atmosphere comprising nitrogen.

In some embodiments, the molar ratio between bromopentane and the compound of Formula (IIa) is about 1.0:1.0 to about 10.0:1.0.

In some embodiments, the molar ratio between bromopentane and the compound of Formula (IIa) is about 1.0:1.0 to about 5.0:1.0.

In some embodiments, the molar ratio between bromopentane and the compound of Formula (IIa) is about 1.0:1.0 to about 2.0:1.0.

In some embodiments, the molar ratio between bromopentane and the compound of Formula (IIa) is about 1.2:1.0.

In some embodiments, the molar ratio between the compound of Formula (IIa) and the Fe catalyst is about 1.0:0.01 to about 1.0:1.0.

In some embodiments, the molar ratio between the compound of Formula (IIa) and the Fe catalyst is about 1.0:0.05 to about 1.0:0.5.

In some embodiments, the molar ratio between the compound of Formula (IIa) and the Fe catalyst is about 1.0:0.10 to about 1.0:0.3.

In some embodiments, the molar ratio between the compound of Formula (IIa) and the Fe catalyst is about 1.0:0.15.

In some embodiments, the molar ratio between the compound of Formula (IIa) and the elemental magnesium is about 1.0:1.0 to about 1.0:5.0.

In some embodiments, the molar ratio between the compound of Formula (IIa) and the elemental magnesium is about 1.0:1.0 to about 1.0:3.0.

In some embodiments, the molar ratio between the compound of Formula (IIa) and the elemental magnesium is about 1.0:1.0 to about 1.0:2.5.

In some embodiments, the molar ratio between the compound of Formula (IIa) and the elemental magnesium is about 1.0:1.5.

In some embodiments, the molar ratio between bromopentane, the compound of Formula (IIa), the elemental magnesium, and the Fe catalyst is about 1.2:1.0:1.5:0.15.

In some embodiments, the step of cross-coupling bromopentane with a compound of Formula (IIa) is conducted at a temperature of about 0° C. to about 75° C.

In some embodiments, the step of cross-coupling bromopentane with a compound of Formula (IIa) is conducted at a temperature of about 10° C. to about 55° C.

In some embodiments, the step of cross-coupling bromopentane with a compound of Formula (IIa) is conducted at a temperature of about 10° C. to about 45° C.

In some embodiments, the step of cross-coupling bromopentane with a compound of Formula (IIa) is conducted by adding the cross-coupling agent to a mixture comprising the elemental magnesium, the Fe catalyst, and the cross-coupling-step solvent to form a first cross-coupling mixture.

In some embodiments, adding the cross-coupling agent to a mixture comprising the elemental magnesium, the Fe catalyst, and the cross-coupling-step solvent is conducted at a rate so the internal temperature during the addition of the cross-coupling agent to the mixture comprising the elemental magnesium, the Fe catalyst, and the cross-coupling-step solvent is maintained at about 0° C. to about 45° C.

In some embodiments, adding the cross-coupling agent to a mixture comprising the elemental magnesium, the Fe catalyst, and the cross-coupling-step solvent is conducted at a rate so the internal temperature during the addition of the cross-coupling agent to the mixture comprising the elemental magnesium, the Fe catalyst, and the cross-coupling-step solvent is maintained at about 10° C. to about 30° C.

In some embodiments, adding the cross-coupling agent to a mixture comprising the elemental magnesium, the Fe catalyst, and the cross-coupling-step solvent is conducted at a rate so the internal temperature during the addition of the cross-coupling agent to the mixture comprising the elemental magnesium, the Fe catalyst, and the cross-coupling-step solvent is maintained at about 15° C. to about 25° C.

In some embodiments, the first cross-coupling mixture is maintained at a temperature of about 10° C. to about 55° C.

In some embodiments, the first cross-coupling mixture is maintained at a temperature of about 20° C. to about 50° C.

In some embodiments, the step of cross-coupling bromopentane with a compound of Formula (IIa) further comprises the step of adding a mixture comprising the bromopentane and the compound of Formula (IIa) to the first cross-coupling mixture to form a second cross-coupling mixture.

In some embodiments, adding the mixture comprising the bromopentane and the compound of Formula (IIa) to the first cross-coupling mixture is conducted at a rate so the internal temperature during the addition of the mixture comprising the bromopentane and the compound of Formula (IIa) to the first cross-coupling mixture is maintained at about 20° C. to about 35° C.

In some embodiments, the mixture comprising the bromopentane and the compound of Formula (IIa) to the first cross-coupling mixture is conducted at a rate so the internal temperature during the addition of the mixture comprising the bromopentane and the compound of Formula (IIa) to the first cross-coupling mixture is maintained at about 25° C. to about 30° C.

In some embodiments, the second cross-coupling mixture is maintained at a temperature of about 20° C. to about 35° C.

In some embodiments, the second cross-coupling mixture is maintained at a temperature of about 20° C. to about 30° C.

In some embodiments, the second cross-coupling mixture is maintained at a temperature of about 23° C. to about 27° C.

In some embodiments, the step of cross-coupling bromopentane with a compound of Formula (IIa) further comprises the step of quenching the second cross-coupling mixture with aqueous HCl.

In some embodiments, the step of cross-coupling bromopentane with a compound of Formula (IIa) is conducted wherein:

the compound of Formula (IIa) is:

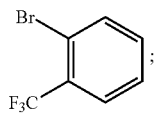

the elemental magnesium is in the form of magnesium turnings;
the Fe catalyst is $FeCl_3$;
the cross-coupling-step solvent comprises tetrahydrofuran (THF); and
the cross-coupling agent comprises N,N,N',N'-tetramethylethylenediamine (TMEDA).

In some embodiments, the molar ratio between bromopentane and the compound of Formula (IIa) is about 1.0:1.0 to about 2.0:1.0.

In some embodiments, the step of cross-coupling bromopentane with a compound of Formula (IIa) is performed wherein the molar ratio between the compound of Formula (IIa) and the Fe catalyst is about 1.0:0.10 to about 1.0:0.3.

In some embodiments, the step of cross-coupling bromopentane with a compound of Formula (IIa) is performed wherein the molar ratio between the compound of Formula (IIa) and the elemental magnesium is about 1.0:1.0 to about 1.0:2.5.

In some embodiments, the step of cross-coupling bromopentane with a compound of Formula (IIa) is performed wherein:

the compound of Formula (IIa) is:

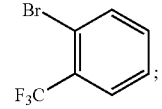

the elemental magnesium is in the form of magnesium turnings;
the Fe catalyst is $FeCl_3$;
the cross-coupling-step solvent comprises tetrahydrofuran (THF); and
the cross-coupling agent comprises N,N,N',N'-tetramethylethylenediamine (TMEDA); and
wherein:
the molar ratio between bromopentane and the compound of Formula (IIa) is about 1.0:1.0 to about 2.0:1.0;
the molar ratio between the compound of Formula (IIa) and the Fe catalyst is about 1.0:0.10 to about 1.0:0.3; and
the molar ratio between the compound of Formula (IIa) and the elemental magnesium is about 1.0:1.0 to about 1.0:2.5.

II. Chloromethylation Step

One aspect of the present invention pertains to processes for preparing 4-(chloromethyl)-1-cyclopentyl-2-(trifluoromethyl)benzene of Formula (IIc):

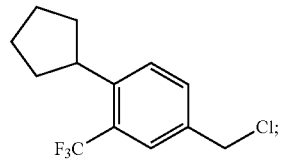

(IIc)

comprising the step of reacting 1-cyclopentyl-2-(trifluoromethyl)benzene (Formula (IIb)):

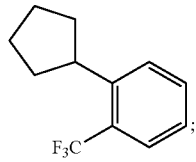

(IIb)

with 1,3,5-trioxane in the presence of an acid and a chlorinating agent, to form 4-(chloromethyl)-1-cyclopentyl-2-(trifluoromethyl)benzene of Formula (IIc).

In some embodiments, the acid comprises sulfuric acid, acetic acid, trifluoroacetic acid, or methanesulfonic acid.

In some embodiments, the acid comprises trifluoroacetic acid.

In some embodiments, the acid comprises sulfuric acid.

In some embodiments, the chlorinating agent comprises thionyl chloride, oxalyl chloride, phosphorous trichloride, phosphorous pentachloride, phosphorous oxychloride, or chlorosulfonic acid.

In some embodiments, the chlorinating agent comprises chlorosulfonic acid.

In some embodiments, the chlorinating agent comprises thionyl chloride.

In some embodiments, the step of reacting 1-cyclopentyl-2-(trifluoromethyl)benzene (Formula IIb) with 1,3,5-trioxane in the presence of an acid and a chlorinating agent is conducted in the presence of a suitable solvent.

In some embodiments, the step of reacting 1-cyclopentyl-2-(trifluoromethyl)benzene (Formula IIb) with 1,3,5-trioxane in the presence of an acid and a chlorinating agent is conducted under a substantially inert atmosphere.

In some embodiments, the step of reacting 1-cyclopentyl-2-(trifluoromethyl)benzene (Formula IIb) with 1,3,5-trioxane in the presence of an acid and a chlorinating agent is conducted under a substantially inert atmosphere comprising argon or nitrogen.

In some embodiments, the step of reacting 1-cyclopentyl-2-(trifluoromethyl)benzene (Formula IIb) with 1,3,5-trioxane in the presence of an acid and a chlorinating agent is conducted under an atmosphere comprising substantially nitrogen.

In some embodiments, the molar ratio between the 1-cyclopentyl-2-(trifluoromethyl)benzene (Formula (IIb)), the 1,3,5-trioxane, and the chlorinating agent is about 1.0:0.3:1.0 to about 1.0:3.0:3.0.

In some embodiments, the molar ratio between the 1-cyclopentyl-2-(trifluoromethyl)benzene (Formula (IIb)), the 1,3,5-trioxane, and the chlorinating agent is about 1.0:1.0:1.5 to about 1.0:2.0:2.5.

In some embodiments, the molar ratio between the 1-cyclopentyl-2-(trifluoromethyl)benzene (Formula (IIb)), the 1,3,5-trioxane, and the chlorinating agent is about 1.0:1.5:2.0.

In some embodiments, the molar ratio between the 1-cyclopentyl-2-(trifluoromethyl)benzene (Formula (IIb)), the 1,3,5-trioxane, the chlorinating agent, and the acid is about 1.0:1.5:2.0:8.0.

In some embodiments, the step of reacting 1-cyclopentyl-2-(trifluoromethyl)benzene (Formula IIb) with 1,3,5-trioxane in the presence of an acid and a chlorinating agent is conducted at a temperature of about −15° C. to about 35° C.

In some embodiments, the step of reacting 1-cyclopentyl-2-(trifluoromethyl)benzene (Formula IIb) with 1,3,5-trioxane in the presence of an acid and a chlorinating agent is conducted at a temperature of about −10° C. to about 25° C.

In some embodiments, the step of reacting 1-cyclopentyl-2-(trifluoromethyl)benzene (Formula IIb) with 1,3,5-trioxane in the presence of an acid and a chlorinating agent is conducted at a temperature of about −5° C. to about 15° C.

In some embodiments, the step of reacting 1-cyclopentyl-2-(trifluoromethyl)benzene (Formula (IIb)) with 1,3,5-trioxane in the presence of an acid and a chlorinating agent, further comprises the step of adding the 1-cyclopentyl-2-(trifluoromethyl)benzene (Formula (IIb)) to a mixture comprising the acid, the chlorinating agent and the 1,3,5-trioxane.

In some embodiments, the adding the 1-cyclopentyl-2-(trifluoromethyl)benzene (Formula (IIb)) to the mixture comprising the acid, the chlorinating agent, and the 1,3,5-trioxane is conducted at a rate so the internal temperature during the addition of the 1-cyclopentyl-2-(trifluoromethyl)benzene (Formula (IIb)) to the mixture comprising the acid, the chlorinating agent, and the 1,3,5-trioxane is maintained at about −25° C. to about 15° C.

In some embodiments, the adding the 1-cyclopentyl-2-(trifluoromethyl)benzene (Formula (IIb)) to the mixture comprising the acid, the chlorinating agent, and the 1,3,5-trioxane is conducted at a rate so the internal temperature during the addition of the 1-cyclopentyl-2-(trifluoromethyl)benzene (Formula (IIb)) to the mixture comprising the acid, the chlorinating agent, and the 1,3,5-trioxane is maintained at about −15° C. to about 10° C.

In some embodiments, the adding the 1-cyclopentyl-2-(trifluoromethyl)benzene (Formula (IIb)) to the mixture comprising the acid, the chlorinating agent, and the 1,3,5-trioxane is conducted at a rate so the internal temperature during the addition of the 1-cyclopentyl-2-(trifluoromethyl)benzene (Formula (IIb)) to the mixture comprising the acid, the chlorinating agent, and the 1,3,5-trioxane is maintained at about −10° C. to about 0° C.

In some embodiments,
the acid comprises sulfuric acid; and
the chlorinating agent comprises thionyl chloride.

III. Indole Forming Step

One aspect of the present invention pertains to processes for preparing a compound of Formula (III):

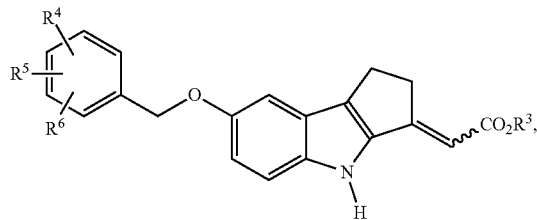

wherein $R^3$ is $C_1$-$C_6$ alkyl; and $R^4$, $R^5$, and $R^6$ are each selected independently from the group consisting of H, $C_1$-$C_4$ alkyl, $C_1$-$C_4$ alkoxy, halogen, $C_1$-$C_4$ haloalkyl, $C_1$-$C_4$ haloalkoxy, and nitro;

comprising the step of reacting a compound of Formula (IIg):

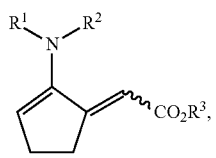

wherein $R^1$ and $R^2$ are each independently $C_1$-$C_6$ alkyl, or $R^1$ and $R^2$ together with the nitrogen atom to which they are both bonded form a 5-member or 6-member heterocyclic ring;

with a compound of Formula (IIh) or a salt thereof,

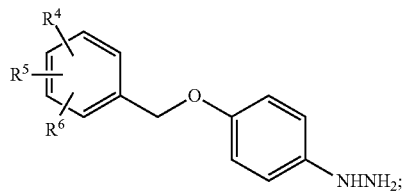

in the presence of an indole-forming acid, to form a compound of Formula (IIi).

In some embodiments, the step of reacting a compound of Formula (IIg) with a compound of Formula (IIh) or a salt thereof, in the presence of an indole-forming acid, optionally comprises a drying agent.

In some embodiments, the step of reacting a compound of Formula (IIg) with a compound of Formula (IIh) or a salt thereof, in the presence of an indole-forming acid, comprises a drying agent.

In some embodiments, the drying agent is selected from the group of magnesium sulfate, sodium sulfate, and molecular sieves.

In some embodiments, the drying agent is magnesium sulfate.

In some embodiments, the drying agent is sodium sulfate.

In some embodiments, the drying agent is molecular sieves.

In some embodiments, $R^1$ and $R^2$ are each independently $C_1$-$C_6$ alkyl.

In some embodiments, $R^1$ and $R^2$ are each independently methyl or ethyl.

In some embodiments, $R^1$ and $R^2$ together with the nitrogen atom to which they are both bonded form a 5-member or 6-member heterocyclic ring.

In some embodiments, $R^1$ and $R^2$ together with the nitrogen atom to which they are both bonded form a 5-member heterocyclic ring.

In some embodiments, $R^1$ and $R^2$ together with the nitrogen atom to which they are both bonded form pyrrolidinyl.

In some embodiments, $R^1$ and $R^2$ together with the nitrogen atom to which they are both bonded form a 6-member heterocyclic ring.

In some embodiments, $R^1$ and $R^2$ together with the nitrogen atom to which they are both bonded form piperidinyl or morpholinyl.

In some embodiments, $R^1$ and $R^2$ together with the nitrogen atom to which they are both bonded form piperidinyl.

In some embodiments, $R^1$ and $R^2$ together with the nitrogen atom to which they are both bonded form morpholinyl.

In some embodiments, $R^3$ is methyl or ethyl.

In some embodiments, $R^3$ is ethyl.

In some embodiments, $R^4$, $R^5$, and $R^6$ are each selected independently from the group consisting of H, $CH_3$, $OCH_3$, $OCH_2CH_3$, F, Cl, Br, $CF_3$, $OCF_3$, and nitro.

In some embodiments, $R^4$, $R^5$, and $R^6$ are each selected independently from the group consisting of H, $CH_3$, $OCH_3$, $OCH_2CH_3$, F, Cl, $CF_3$, $OCF_3$.

In some embodiments, $R^4$, $R^5$, and $R^6$ are each selected independently from the group consisting of H and $OCH_3$.

In some embodiments, $R^4$, $R^5$, and $R^6$ are each H.

In some embodiments, the compound of Formula (IIi) is:

In some embodiments, the compound of Formula (IIi) is:

In some embodiments, the compound of Formula (IIg) is:

In some embodiments, the compound of Formula (IIh) is (4-(benzyloxy)phenyl) hydrazine:

or a salt thereof.

In some embodiments, the compound of Formula (IIh) is (4-(benzyloxy)phenyl) hydrazine hydrochloride.

In some embodiments, the indole-forming acid comprises a Brønsted acid or a Lewis acid.

In some embodiments, the indole-forming acid comprises acetic acid, trifluoroacetic acid, p-TsOH, $H_3PO_4$, $H_2SO_4$, methanesulfonic acid, formic acid, HCl, $ZnCl_2$, $FeCl_3$, HCl, CuCl, CuI, $BF_3OEt_2$, $Zn(Tf)_2$, $Yb(Tf)_2$, $Sc(Tf)_2$, or $AlCl_3$.

In some embodiments, the indole-forming acid comprises a Brønsted acid.

In some embodiments, the indole-forming acid comprises acetic acid, trifluoroacetic acid, p-TsOH, $H_3PO_4$, $H_2SO_4$, methanesulfonic acid, formic acid, or HCl. It is understood p-TsOH is para toluenesulfonic acid (i.e., 4-toluenesulfonic acid).

In some embodiments, the indole-forming acid comprises acetic acid.

In some embodiments, the indole-forming acid comprises trifluoroacetic acid.

In some embodiments, the indole-forming acid comprises a mixture of acetic acid and trifluoroacetic acid.

In some embodiments, the indole-forming acid comprises a Lewis acid.

In some embodiments, the indole-forming acid comprises $ZnCl_2$, $FeCl_3$, HCl, CuCl, CuI, $BF_3OEt_2$, $Zn(Tf)_2$, $Yb(Tf)_2$, $Sc(Tf)_2$, or $AlCl_3$.

In some embodiments, the step of reacting a compound of Formula (IIg) with a compound of Formula (IIh) or a salt thereof, in the presence of an indole-forming acid is conducted in the presence of a suitable solvent.

In some embodiments, the step of reacting a compound of Formula (IIg) with a compound of Formula (IIh) or a salt thereof, in the presence of an indole-forming acid is conducted in the presence of a protic solvent, a halogenated solvent, an ether solvent, or an aprotic solvent.

In some embodiments, the step of reacting a compound of Formula (IIg) with a compound of Formula (IIh) or a salt thereof, in the presence of an indole-forming acid is conducted in the presence of a protic solvent.

In some embodiments, the protic solvent comprises a $C_1$-$C_4$ alkylalcohol solvent.

In some embodiments, the step of reacting a compound of Formula (IIg) with a compound of Formula (IIh) or a salt thereof, in the presence of an indole-forming acid is conducted in the presence of a halogenated solvent.

In some embodiments, the halogenated solvent comprises dichloromethane.

In some embodiments, the step of reacting a compound of Formula (IIg) with a compound of Formula (IIh) or a salt thereof, in the presence of an indole-forming acid is conducted in the presence of an ether solvent.

In some embodiments, the step of reacting a compound of Formula (IIg) with a compound of Formula (IIh) or a salt thereof, in the presence of an indole-forming acid is conducted in the presence of an aprotic solvent.

In some embodiments, the aprotic solvent comprises acetonitrile or toluene.

In some embodiments, the aprotic solvent comprises acetonitrile.

In some embodiments, the aprotic solvent comprises toluene.

In some embodiments, the step of reacting a compound of Formula (IIg) with a compound of Formula (IIh) or a salt thereof, in the presence of an indole-forming acid is conducted in the presence of a $C_1$-$C_4$ alkylalcohol solvent.

In some embodiments, the $C_1$-$C_4$ alkylalcohol solvent comprises methanol or ethanol.

In some embodiments, the $C_1$-$C_1$ alkylalcohol solvent comprises ethanol.

In some embodiments, the step of reacting a compound of Formula (IIg) with a compound of Formula (IIh) or a salt thereof, in the presence of an indole-forming acid is conducted under a substantially inert atmosphere.

In some embodiments, the step of reacting a compound of Formula (IIg) with a compound of Formula (IIh) or a salt thereof, in the presence of an indole-forming acid is conducted under a substantially inert atmosphere comprising argon or nitrogen.

In some embodiments, the step of reacting a compound of Formula (IIg) with a compound of Formula (IIh) or a salt thereof, in the presence of an indole-forming acid is conducted under a substantially inert atmosphere comprising nitrogen.

In some embodiments, the molar ratio between the compound of Formula (IIg) and the compound of Formula (IIh) or a salt thereof is about 1.0:1.0 to about 1.0:2.0.

In some embodiments, the molar ratio between the compound of Formula (IIg) and the compound of Formula (IIh) or a salt thereof is about 1.0:1.0 to about 1.0:1.5.

In some embodiments, the molar ratio between the compound of Formula (IIg) and the compound of Formula (IIh) or a salt thereof is about 1.0:1.0 to about 1.0:1.3.

In some embodiments, the molar ratio between the compound of Formula (IIg) and the compound of Formula (IIh) or a salt thereof is about 1.0:1.0 to about 1.0:1.1.

In some embodiments, the step of reacting a compound of Formula (IIg) with a compound of Formula (IIh) or a salt thereof, in the presence of an indole-forming acid, is conducted at a temperature of about 25° C. to about 80° C.

In some embodiments, the step of reacting a compound of Formula (IIg) with a compound of Formula (IIh) or a salt thereof, in the presence of an indole-forming acid, is conducted at a temperature of about 50° C. to about 70° C.

In some embodiments, the step of reacting a compound of Formula (IIg) with a compound of Formula (IIh) or a salt thereof, in the presence of an indole-forming acid, is conducted at a temperature of about 60° C. to about 65° C.

In some embodiments, the step of reacting a compound of Formula (IIg) with a compound of Formula (IIh) or a salt thereof, in the presence of an indole-forming acid comprises formation of an imine intermediate of Formula (III):

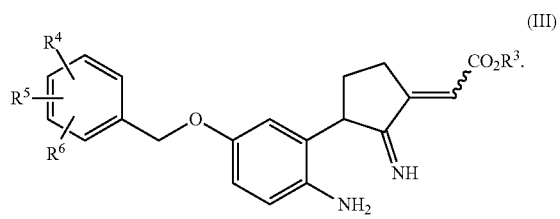

In some embodiments, $R^3$ is ethyl.

In some embodiments, $R^4$, $R^5$, and $R^6$ are each H.

In some embodiments, $R^3$ is ethyl, and $R^4$, $R^5$, and $R^6$ are each H.

In some embodiments, the step of reacting a compound of Formula (IIg) with a compound of Formula (IIh) or a salt thereof, in the presence of an indole-forming acid comprises formation of an imine intermediate of the formula:

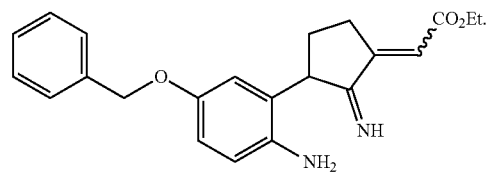 [SMILES: CCOC(=O)C=C1CCC(c2cc(OCc3ccccc3)ccc2N)C1=N]

In some embodiments, the step of reacting a compound of Formula (IIg) with a compound of Formula (IIh) or a salt thereof, in the presence of an indole-forming acid, is continued until about 8.0% or less of the compound of Formula (III) is present as determined by HPLC.

In some embodiments, the step of reacting a compound of Formula (IIg) with a compound of Formula (IIh) or a salt thereof, in the presence of an indole-forming acid, is continued until about 6.0% or less of the compound of Formula (III) is present as determined by HPLC.

In some embodiments, the step of reacting a compound of Formula (IIg) with a compound of Formula (IIh) or a salt thereof, in the presence of an indole-forming acid, is continued until about 5.0% or less of the compound of Formula (III) is present as determined by HPLC.

In some embodiments, the step of reacting a compound of Formula (IIg) with a compound of Formula (IIh) or a salt thereof, in the presence of an indole-forming acid, is continued until about 4.0% or less of the compound of Formula (III) is present as determined by HPLC.

In some embodiments, the step of reacting a compound of Formula (IIg) with a compound of Formula (IIh) or a salt thereof, in the presence of an indole-forming acid, further comprises the steps of isomerizing and crystallizing the compound of Formula (IIi) at a temperature of about 20° C. to about 25° C. to form a suspension comprising said compound of Formula (IIi).

In some embodiments, the step of reacting a compound of Formula (IIg) with a compound of Formula (IIh) or a salt thereof, in the presence of an indole-forming acid, further comprises the step of cooling said suspension comprising said compound of Formula (IIi) to a temperature of about 0° C. to about 5° C.

In some embodiments, the step of reacting a compound of Formula (IIg) with a compound of Formula (IIh) or a salt thereof, in the presence of an indole-forming acid, further comprises the step of isolating the compound of Formula (In). In some embodiments, isolating the compound of Formula (IIi) is conducted by filtration.

IV. Processes for Preparing Compounds of Formula (IIg)

One aspect of the present invention pertains to processes for preparing a compound of Formula (IIg):

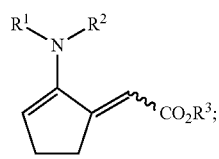

(IIg)

wherein $R^3$ is $C_1$-$C_6$ alkyl;
comprising the following steps of:

a) reacting cyclopentanone with a secondary amine of Formula (IId):

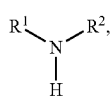

(IId)

wherein $R^1$ and $R^2$ are each independently $C_1$-$C_6$ alkyl, or $R^1$ and $R^2$ together with the nitrogen atom to which they are both bonded form a 5-member or 6-member heterocyclic ring; to form a compound of Formula (IIe):

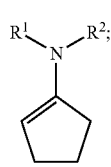

(IIe)

and b) reacting the compound of Formula (IIe) with a compound of Formula (IIf):

(IIf)

wherein $R^3$ is $C_1$-$C_6$ alkyl,
to form the compound of Formula (IIg).

IVa. Enamine Formation, Step a)

In some embodiments, $R^1$ and $R^2$ together with the nitrogen atom to which they are both bonded form a 5-member or 6-member heterocyclic ring.

In some embodiments, $R^1$ and $R^2$ together with the nitrogen atom to which they are both bonded form a 5-member heterocyclic ring.

In some embodiments, $R^1$ and $R^2$ together with the nitrogen atom to which they are both bonded form pyrrolidinyl.

In some embodiments, $R^1$ and $R^2$ together with the nitrogen atom to which they are both bonded form a 6-member heterocyclic ring.

In some embodiments, $R^1$ and $R^2$ together with the nitrogen atom to which they are both bonded form piperidinyl or morpholinyl.

In some embodiments, $R^1$ and $R^2$ together with the nitrogen atom to which they are both bonded form morpholinyl.

In some embodiments, the compound of Formula (IIe) is:

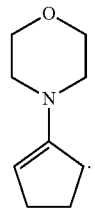 [SMILES: C1=C(N2CCOCC2)CCC1]

In some embodiments, the step of reacting cyclopentanone with a secondary amine of Formula (IId) is conducted in the presence of an azeotropic solvent.

In some embodiments, the azeotropic solvent comprises benzene, toluene, cyclohexane or anisole.

In some embodiments, the azeotropic solvent comprises cyclohexane.

In some embodiments, the step of reacting cyclopentanone with a secondary amine of Formula (IId) is conducted under a substantially inert atmosphere.

In some embodiments, the step of reacting cyclopentanone with a secondary amine of Formula (Id) is conducted under an atmosphere comprising argon or nitrogen.

In some embodiments, the step of reacting cyclopentanone with a secondary amine of Formula (IId) is conducted under an atmosphere comprising nitrogen.

In some embodiments, the molar ratio of cyclopentanone and the secondary amine of Formula (IId) is about 1.0:1.0 to about 1.0:2.0.

In some embodiments, the molar ratio of cyclopentanone and the secondary amine of Formula (IId) is about 1.0:1.0 to about 1.0:1.5.

In some embodiments, the molar ratio of cyclopentanone and the secondary amine of Formula (IId) is about 1.0:1.0 to about 1.0:1.2.

In some embodiments, the molar ratio of cyclopentanone and the secondary amine of Formula (IId) is about 1.0:1.0 to about 1.0:1.05.

In some embodiments, the molar ratio of cyclopentanone and the secondary amine of Formula (IId) is about 1.0:1.0 to about 1.0:1.005.

In some embodiments, the step of reacting cyclopentanone with a secondary amine of Formula (IId) is conducted at a temperature of about 60° C. to about 155° C.

In some embodiments, the step of reacting cyclopentanone with a secondary amine of Formula (IId) is conducted at a temperature of about 65° C. to about 111° C.

In some embodiments, the step of reacting cyclopentanone with a secondary amine of Formula (IId) is conducted at a temperature of about 85° C. to about 95° C.

In some embodiments, the step of reacting cyclopentanone with a secondary amine of Formula (IId) further comprises a step of removing water.

In some embodiments, the step of reacting cyclopentanone with a secondary amine of Formula (IId) further comprises a step of removing water via a Dean-Stark water trap.

In some embodiments, the removing water step is conducted until about 10% or less of cyclopentanone is present as determined by gas chromatography.

In some embodiments, the removing water step is conducted until about 6% or less of cyclopentanone is present as determined by gas chromatography.

In some embodiments, the removing water step is conducted until about 3% or less of cyclopentanone is present as determined by gas chromatography.

In some embodiments, the removing water is conducted until about 10% or less of the secondary amine of Formula (IId) is present as determined by gas chromatography.

In some embodiments, the removing water is conducted until about 6% or less of the secondary amine of Formula (IId) is present as determined by gas chromatography.

In some embodiments, the removing water is conducted until about 3% or less of the secondary amine of Formula (IId) is present as determined by gas chromatography.

IVa. Reacting the enamine of formula (IIe) with a compound of formula (IIf), Step b)

In some embodiments, the step of reacting the compound of Formula (IIe) with a compound of Formula (IIf) is conducted in the presence of an azeotropic solvent.

In some embodiments, the azeotropic solvent comprises benzene, toluene, cyclohexane or anisole.

In some embodiments, the azeotropic solvent comprises cyclohexane.

In some embodiments, the step of reacting the compound of Formula (IIe) with a compound of Formula (IIf) is conducted under a substantially inert atmosphere.

In some embodiments, the step of reacting the compound of Formula (IIe) with a compound of Formula (IIf) is conducted under an atmosphere comprising argon or nitrogen.

In some embodiments, the step of reacting the compound of Formula (IIe) with a compound of Formula (IIf)) is conducted under an atmosphere comprising nitrogen.

In some embodiments, the molar ratio between the compound of Formula (IIe) and the compound of Formula (IIf)) is about 1.0:1.0 to about 1.0:2.0.

In some embodiments, the molar ratio between the compound of Formula (IIe) and the compound of Formula (IIf) is about 1.0:1.0 to about 1.0:1.8.

In some embodiments, the molar ratio between the compound of Formula (IIe) and the compound of Formula (IIf) is about 1.0:1.0 to about 1.0:1.4.

In some embodiments, the molar ratio between the compound of Formula (IIe) and the compound of Formula (IIf) is about 1.0:1.0 to about 1.0:1.2.

In some embodiments, the molar ratio between the compound of Formula (IIe) and the compound of Formula (IIf) is about 1.0:1.1.

In some embodiments, the step of reacting the compound of Formula (IIe) with a compound of Formula (IIf) is conducted at a temperature of about 25° C. to about 105° C.

In some embodiments, the step of reacting the compound of Formula (IIe) with a compound of Formula (IIf) is conducted at a temperature of about 55° C. to about 100° C.

In some embodiments, the step of reacting the compound of Formula (IIe) with a compound of Formula (IIf) is conducted at a temperature of about 60° C. to about 95° C.

In some embodiments, the step of reacting the compound of Formula (IIe) with a compound of Formula (IIf) further comprises a step of removing water.

In some embodiments, the step of reacting the compound of Formula (IIe) with a compound of Formula (IIf) further comprises a step of removing water via a Dean-Stark water trap.

In some embodiments, removing water step is continued until about 5.0% or less of the compound of Formula (IIe) is present as determined by gas chromatography.

In some embodiments, removing water step is continued until about 2.5% or less of the compound of Formula (IIe) is present as determined by gas chromatography.

In some embodiments, removing water step is continued until about 2.0% or less of the compound of Formula (IIe) is present as determined by gas chromatography.

In some embodiments, removing water step is continued until about 1.0% or less of the compound of Formula (IIe) is present as determined by gas chromatography.

In some embodiments, removing water step is continued until about 0.5% or less of the compound of Formula (IIe) is present as determined by gas chromatography.

V. Reduction Step

One aspect of the present invention pertains to processes for preparing a compound of Formula (IIj) or a salt thereof:

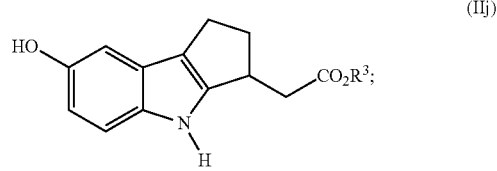

(IIj)

wherein $R^3$ is $C_1$-$C_6$ alkyl;
comprising the step of reducing a compound of Formula (IIi):

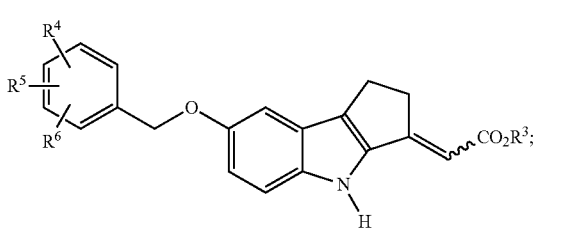

(IIi)

wherein $R^4$, $R^5$, and $R^6$ are each selected independently from the group consisting of H, $C_1$-$C_4$ alkyl, $C_1$-$C_4$ alkoxy, halogen, $C_1$-$C_4$ haloalkyl, $C_1$-$C_4$ haloalkoxy, and nitro;

in the presence of a reducing-step agent, and a reducing-step catalyst, to form the compound of Formula (IIj).

In some embodiments, the compound of Formula (IIj) is:

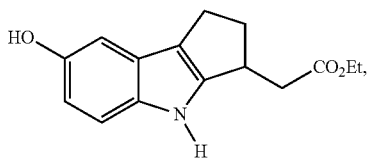 [SMILES: CCOC(=O)CC1CCc2c1[nH]c1ccc(O)cc21]

or a salt thereof.

In some embodiments, $R^3$ is methyl or ethyl.

In some embodiments, $R^3$ is ethyl.

In some embodiments, the reducing-step agent comprises formic acid and a reducing base.

In some embodiments, the reducing base comprises an inorganic base.

In some embodiments, the reducing base comprises a carbonate base.

In some embodiments, the reducing base comprises sodium carbonate, potassium carbonate, or cesium carbonate.

In some embodiments, the reducing base comprises sodium carbonate.

In some embodiments, the reducing base comprises potassium carbonate.

In some embodiments, the reducing base comprises an organic amine base.

In some embodiments, the reducing base comprises ammonia, dimethylamine, diethylamine, trimethylamine, or triethylamine.

In some embodiments, the reducing base comprises triethylamine.

In some embodiments, the reducing-step catalyst comprises palladium.

In some embodiments, the reducing-step catalyst comprises palladium on carbon.

In some embodiments, the reducing-step catalyst comprises about 2% palladium on carbon to about 10% palladium on carbon.

In some embodiments, the reducing-step catalyst comprises about 10% palladium on carbon.

In some embodiments, the step of reducing a compound of Formula (IIi) in the presence of a reducing-step agent, and a reducing-step catalyst is conducted in the presence of a suitable solvent.

In some embodiments, the step of reducing a compound of Formula (IIi) in the presence of a reducing-step agent, and a reducing-step catalyst is conducted in the presence of a reducing-step solvent.

In some embodiments, the step of reducing a compound of Formula (IIi) in the presence of a reducing-step agent, and a reducing-step catalyst is conducted in the presence of a reducing-step solvent comprising a $C_1$-$C_4$ alkylalcohol.

In some embodiments, the step of reducing a compound of Formula (IIi) in the presence of a reducing-step agent, and a reducing-step catalyst is conducted in the presence of a reducing-step solvent comprising methanol or ethanol.

In some embodiments, the step of reducing a compound of Formula (IIi) in the presence of a reducing-step agent, and a reducing-step catalyst is conducted in the presence of a reducing-step solvent comprising ethyl acetate.

In some embodiments, the ethyl acetate is substantially free of dissolved oxygen.

In some embodiments, the step of reducing a compound of Formula (IIi) in the presence of a reducing-step agent, and a reducing-step catalyst is conducted under a substantially inert atmosphere.

In some embodiments, the step of reducing a compound of Formula (IIi) in the presence of a reducing-step agent, and a reducing-step catalyst is conducted under a substantially inert atmosphere comprising argon or nitrogen.

In some embodiments, the step of reducing a compound of Formula (IIi) in the presence of a reducing-step agent, and a reducing-step catalyst is conducted under a substantially inert atmosphere comprising nitrogen.

In some embodiments, the molar ratio between the compound of Formula (IIi), formic acid, and the reducing base is about 1.0:1.0:1.0 to about 1.0:6.0:6.0.

In some embodiments, the molar ratio between the compound of Formula (IIi), formic acid, and the reducing base is about 1.0:1.0:1.0 to about 1.0:5.0:5.0.

In some embodiments, the molar ratio between the compound of Formula (IIi), formic acid, and the reducing base is about 1.0:2.0:2.0 to about 1.0:4.0:4.0.

In some embodiments, the molar ratio between the compound of Formula (IIi), formic acid, and the reducing base is about 1.0:2.0:2.0 to about 1.0:3.0:3.0.

In some embodiments, the molar ratio between the compound of Formula (IIi), formic acid, and the reducing base is about 1.0:3.0:3.0.

In some embodiments, the step of reducing a compound of Formula (IIi) in the presence of a reducing-step agent, and a reducing-step catalyst is conducted at a temperature of about 15° C. to about 55° C.

In some embodiments, the step of reducing a compound of Formula (IIi) in the presence of a reducing-step agent, and a reducing-step catalyst is conducted at a temperature of about 20° C. to about 45° C.

In some embodiments, the step of reducing a compound of Formula (IIi) in the presence of a reducing-step agent, and a reducing-step catalyst is conducted at a temperature of about 25° C. to about 35° C.

In some embodiments, the step of reducing a compound of Formula (IIi) in the presence of a reducing-step agent, and a reducing-step catalyst is conducted by adding the reducing base to a mixture comprising the compound of Formula (IIi), formic acid, the reducing-step catalyst, and the reducing-step solvent.

In some embodiments, the step of reducing a compound of Formula (IIi) in the presence of a reducing-step agent, and a reducing-step catalyst is conducted by adding triethylamine to a mixture comprising the compound of Formula (IIi), formic acid, the reducing-step catalyst, and the reducing-step solvent at a temperature of about 25° C. to about 35° C., wherein the compound of Formula (IIi) is:

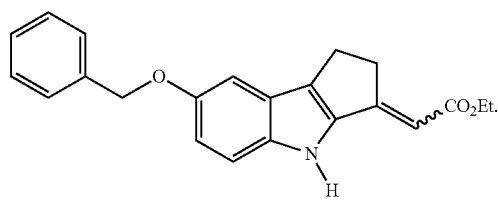 [SMILES: CCOC(=O)C=C1CCc2c1[nH]c1ccc(OCc3ccccc3)cc21]

In some embodiments, the step of reducing a compound of Formula (IIi) in the presence of a reducing-step agent, and a reducing-step catalyst, further comprises the step of crystallizing the compound of Formula (IIj) in the presence of ethyl acetate and heptanes.

In some embodiments, crystallizing the compound of Formula (IIj) is conducted at a temperature of about 0° C. to about 20° C.

In some embodiments, crystallizing the compound of Formula (IIj) is conducted at a temperature of about 5° C. to about 15° C.

In some embodiments, crystallizing the compound of Formula (IIj) is conducted at a temperature of about 10° C.

In some embodiments, the step of reducing a compound of Formula (IIi) in the presence of a reducing-step agent, and a reducing-step catalyst, further comprises the step of isolating the compound of Formula (IIj).

In some embodiments, isolating the compound of Formula (IIj) is conducted by filtration.

VI. Alkylating Step

One aspect of the present invention pertains to processes for preparing a compound of Formula (IIk):

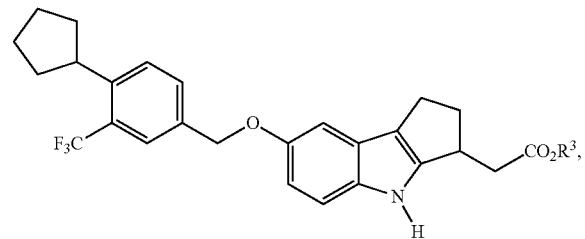

wherein $R^3$ is $C_1$-$C_6$ alkyl;
comprising the step of alkylating a compound of Formula (IIj) or a salt thereof:

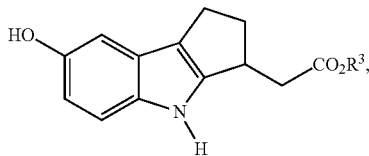

with 4-(chloromethyl)-1-cyclopentyl-2-(trifluoromethyl) benzene (Formula (IIc)):

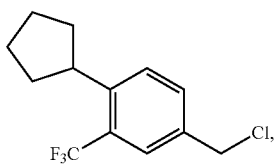

in the presence of an alkylating-step base, and an alkylating-step solvent to form the compound of Formula (IIk).

In some embodiments, the alkylating-step solvent is other than dimethylformamide (DMF). In some embodiments, the alkylating-step solvent is other than dimethylacetamide (DMA). In some embodiments, the alkylating-step solvent is other than a solvent of the group consisting of dimethylformamide (DMF) and dimethylacetamide (DMA).

In some embodiments, the compound of Formula (IIk) is:

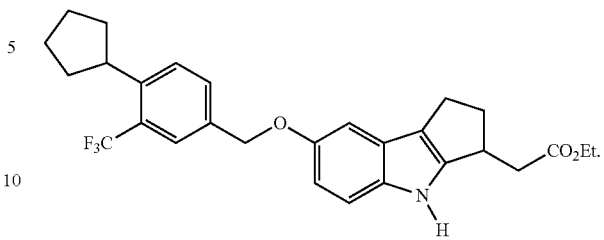

In some embodiments, $R^3$ is methyl or ethyl.
In some embodiments, $R^3$ is ethyl.
In some embodiments, the alkylating-step base is an inorganic base.

In some embodiments, the alkylating-step base comprises a carbonate base.

In some embodiments, the alkylating-step base comprises sodium carbonate, potassium carbonate, or cesium carbonate.

In some embodiments, the alkylating-step base comprises cesium carbonate.

In some embodiments, the alkylating-step solvent comprises a suitable solvent.

In some embodiments, the alkylating-step solvent comprises an aprotic solvent.

In some embodiments, the alkylating-step solvent comprises acetone, 2-butanone, dimethylformamide (DMF), dimethylacetamide (DMA), tetrahydrofuran (THF) or acetonitrile.

In some embodiments, the alkylating-step solvent comprises acetonitrile.

In some embodiments, the alkylating-step solvent is substantially free of water.

In some embodiments, the step of alkylating a compound of Formula (IIj) or a salt thereof, with 4-(chloromethyl)-1-cyclopentyl-2-(trifluoromethyl)benzene (Formula (IIc)) in the presence of an alkylating-step base, and an alkylating-step solvent, is conducted wherein:
the compound of Formula (IIj) is:

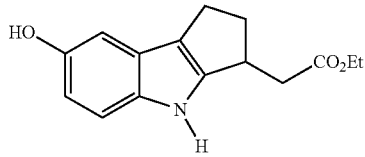

or a salt thereof;
the alkylating-step base comprises cesium carbonate; and
the alkylating-step solvent comprises acetonitrile.

In some embodiments, the step of alkylating a compound of Formula (IIj) or a salt thereof, with 4-(chloromethyl)-1-cyclopentyl-2-(trifluoromethyl)benzene (Formula (IIc)) in the presence of an alkylating-step base, and an alkylating-step solvent is conducted under a substantially inert atmosphere.

In some embodiments, the step of alkylating a compound of Formula (IIj) or a salt thereof, with 4-(chloromethyl)-1-cyclopentyl-2-(trifluoromethyl)benzene (Formula (IIc)) in the presence of an alkylating-step base, and an alkylating-step solvent is conducted under a substantially inert atmosphere comprising argon or nitrogen.

In some embodiments, the step of alkylating a compound of Formula (IIj) or a salt thereof, with 4-(chloromethyl)-1- cyclopentyl-2-(trifluoromethyl)benzene (Formula (IIc)) in the presence of an alkylating-step base, and an alkylating-step solvent is conducted under a substantially inert atmosphere comprising nitrogen.

In some embodiments, the molar ratio between 4-(chloromethyl)-1-cyclopentyl-2-(trifluoromethyl)benzene (Formula (IIc)), the compound of Formula (IIj) or a salt thereof, and the alkylating-step base is about 1.0:1.0:0.5 to about 2.0:1.0:3.0.

In some embodiments, the molar ratio between 4-(chloromethyl)-1-cyclopentyl-2-(trifluoromethyl)benzene (Formula (IIc)), the compound of Formula (IIj) or a salt thereof, and the alkylating-step base is about 1.0:1.0:1.0 to about 1.5:1.0:2.0.

In some embodiments, the molar ratio between 4-(chloromethyl)-1-cyclopentyl-2-(trifluoromethyl)benzene (Formula (IIc)), the compound of Formula (IIj) or a salt thereof, and the alkylating-step base is about 1.0:1.0:1.0 to about 1.2:1.0:1.5.

In some embodiments, the molar ratio between 4-(chloromethyl)-1-cyclopentyl-2-(trifluoromethyl)benzene (Formula (IIc)), the compound of Formula (IIj) or a salt thereof, and the alkylating-step base is about 1.1:1.0:1.3

In some embodiments, the step of alkylating a compound of Formula (IIj) or a salt thereof, with 4-(chloromethyl)-1-cyclopentyl-2-(trifluoromethyl)benzene (Formula (IIc)) in the presence of an alkylating-step base, and an alkylating-step solvent is conducted at a temperature of about 15° C. to about 90° C.

In some embodiments, the step of alkylating a compound of Formula (IIIj) or a salt thereof, with 4-(chloromethyl)-1-cyclopentyl-2-(trifluoromethyl)benzene (Formula (IIc)) in the presence of an alkylating-step base, and an alkylating-step solvent is conducted at a temperature of about 21° C. to about 85° C.

In some embodiments, the step of alkylating a compound of Formula (IIj) or a salt thereof, with 4-(chloromethyl)-1-cyclopentyl-2-(trifluoromethyl)benzene (Formula (IIc)) in the presence of an alkylating-step base, and an alkylating-step solvent is conducted at a temperature of about 65° C. to about 80° C.

In some embodiments, the step of alkylating a compound of Formula (IIj) or a salt thereof, with 4-(chloromethyl)-1-cyclopentyl-2-(trifluoromethyl)benzene (Formula (IIc)) in the presence of an alkylating-step base, and an alkylating-step solvent, further comprises the step of adding 4-(chloromethyl)-1-cyclopentyl-2-(trifluoromethyl)benzene (Formula (IIc)) to a mixture comprising the compound of Formula (IIj) or a salt thereof, alkylating-step base, and alkylating-step solvent to form an alkylating mixture.

In some embodiments, adding 4-(chloromethyl)-1-cyclopentyl-2-(trifluoromethyl)benzene (Formula (IIc)) to the mixture comprising the compound of Formula (IIj) or a salt thereof, alkylating-step base, and alkylating-step solvent is conducted with heating so the internal temperature during the addition of 4-(chloromethyl)-1-cyclopentyl-2-(trifluoromethyl)benzene (Formula (IIc)) to the alkylating mixture comprising the compound of Formula (IIj) or a salt thereof, alkylating-step base, and alkylating-step solvent is about 20° C. to about 85° C.

In some embodiments, the alkylating mixture is maintained at about 60° C. to about 85° C.

In some embodiments, the alkylating mixture is maintained at about 70° C. to about 85° C.

In some embodiments, the alkylating mixture is maintained at about 75° C. to about 80° C.

In some embodiments, the step of alkylating a compound of Formula (IIj) or a salt thereof, with 4-(chloromethyl)-1-cyclopentyl-2-(trifluoromethyl)benzene (Formula (IIc)) in the presence of an alkylating-step base, and an alkylating-step solvent, further comprises the steps of cooling the alkylating mixture to a temperature of about 50° C. to about 60° C. and filtering the alkylating mixture to form a filtered mixture.

In some embodiments, the step of alkylating a compound of Formula (IIj) or a salt thereof, with 4-(chloromethyl)-1-cyclopentyl-2-(trifluoromethyl)benzene (Formula (IIc)) in the presence of an alkylating-step base, and an alkylating-step solvent, further comprises the step of precipitating the compound of Formula (IIk) from the filtered mixture.

In some embodiments, precipitating the compound of Formula (IIk) from the filtered mixture comprises reducing the volume of the filtered mixture.

In some embodiments, precipitating the compound of Formula (IIk) from the filtered mixture comprises reducing the volume of the filtered mixture by about one half.

In some embodiments, the step of alkylating a compound of Formula (IIj) or a salt thereof, with 4-(chloromethyl)-1-cyclopentyl-2-(trifluoromethyl)benzene (Formula (IIc)) in the presence of an alkylating-step base, and an alkylating-step solvent, further comprises isolating the precipitate of the compound of Formula (IIk) from the filtered mixture.

In some embodiments, isolating the precipitate of the compound of Formula (IIk) is conducted by filtration.

VII. Hydrolyzing Step

One aspect of the present invention pertains to processes for preparing (R)-2-(7-(4-cyclopentyl-3-(trifluoromethyl)benzyloxy)-1,2,3,4-tetrahydrocyclopenta[b]indol-3-yl)acetic acid of Formula (Ia):

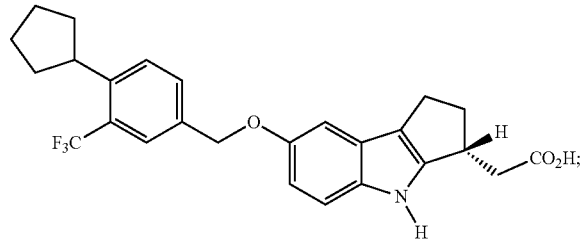

(Ia)

comprising the step of hydrolyzing a compound of Formula (IIk):

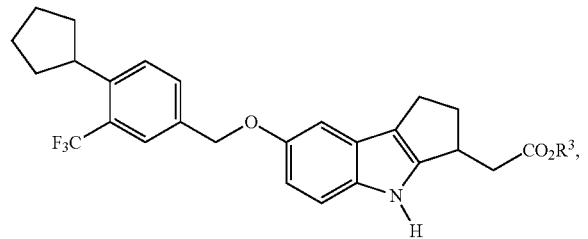 [SMILES: CCOC(=O)CC1CCc2c1[nH]c1ccc(OCc3ccc(C4CCCC4)c(C(F)(F)F)c3)cc21]

(IIk)

$R^3$ is $C_1$-$C_6$ alkyl;
in the presence of a lipase and a hydrolyzing-step solvent to form (R)-2-(7-(4-cyclopentyl-3-(trifluoromethyl)benzyloxy)-1,2,3,4-tetrahydrocyclopenta[b]indol-3-yl)acetic acid of Formula (Ia).

In some embodiments, R³ is methyl or ethyl.

In some embodiments, R³ is ethyl.

In some embodiments, the lipase is selected from the group consisting of lipase B *Candida Antarctica*, lipase *Mucor miehei*, and *P. fluorescens*.

In some embodiments, the lipase is *Candida antarctica* lipase B.

In some embodiments, the lipase is immobilized *Candida antarctica* lipase B.

In some embodiments, the hydrolyzing-step solvent comprises a suitable solvent.

In some embodiments, the hydrolyzing-step solvent comprises dimethylformamide (DMF), dimethylacetamide (DMA), dimethylsulfoxide (DMSO), tetrahydrofuran (THF), or acetonitrile.

In some embodiments, the hydrolyzing-step solvent comprises acetonitrile.

In some embodiments, the step of hydrolyzing the compound of Formula (IIk) in the presence of a lipase and a hydrolyzing-step solvent, is conducted wherein:
the compound of Formula (IIk) is:

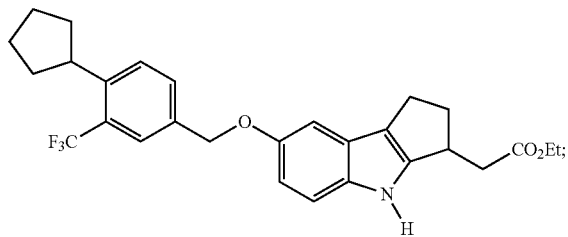 [SMILES: CCOC(=O)CC1CCc2c1[nH]c1ccc(OCc3ccc(C4CCCC4)c(C(F)(F)F)c3)cc21]

the lipase is immobilized *Candida antarctica* lipase B; and
the hydrolyzing-step solvent comprises acetonitrile.

In some embodiments, the step of hydrolyzing the compound of Formula (IIk) in the presence of a lipase and a hydrolyzing-step solvent is conducted in the presence of a phosphate buffer.

In some embodiments, the step of hydrolyzing the compound of Formula (IIk) in the presence of a lipase and a hydrolyzing-step solvent is conducted in the presence of a phosphate buffer at a pH of about 6.0 to about 9.0.

In some embodiments, the step of hydrolyzing the compound of Formula (IIk) in the presence of a lipase and a hydrolyzing-step solvent is conducted in the presence of a phosphate buffer at a pH of about 7.0 to about 8.5.

In some embodiments, the step of hydrolyzing the compound of Formula (IIk) in the presence of a lipase and a hydrolyzing-step solvent is conducted in the presence of a phosphate buffer at a pH of about 7.3 to about 8.3.

In some embodiments, the step of hydrolyzing the compound of Formula (IIk) in the presence of a lipase and a hydrolyzing-step solvent is conducted in the presence of a phosphate buffer at a pH of about 7.6 to about 8.0.

In some embodiments, the step of hydrolyzing the compound of Formula (IIk) in the presence of a lipase and a hydrolyzing-step solvent is conducted in the presence of a phosphate buffer at a pH of about 7.8.

In some embodiments, the phosphate buffer is a sodium phosphate buffer.

In some embodiments, the phosphate buffer is a potassium phosphate buffer.

In some embodiments, the step of hydrolyzing the compound of Formula (IIk) in the presence of a lipase and a hydrolyzing-step solvent is conducted at a temperature of about 0° C. to about 75° C.

In some embodiments, the step of hydrolyzing the compound of Formula (IIk) in the presence of a lipase and a hydrolyzing-step solvent is conducted at a temperature of about 20° C. to about 65° C.

In some embodiments, the step of hydrolyzing the compound of Formula (IIk) in the presence of a lipase and a hydrolyzing-step solvent is conducted at a temperature of about 30° C. to about 55° C.

In some embodiments, the step of hydrolyzing the compound of Formula (IIk) in the presence of a lipase and a hydrolyzing-step solvent is conducted at a temperature of about 35° C. to about 45° C.

In some embodiments, the step of hydrolyzing the compound of Formula (IIk) in the presence of a lipase and a hydrolyzing-step solvent is conducted at a temperature of about 40° C.

In some embodiments, the step of hydrolyzing the compound of Formula (IIIk) in the presence of a lipase and a hydrolyzing-step solvent, further comprises the step of isolating the (R)-2-(7-(4-cyclopentyl-3-(trifluoromethyl)benzyloxy)-1,2,3,4-tetrahydrocyclopenta[b]indol-3-yl)acetic acid of Formula (Ia).

In some embodiments, after the step of isolating (R)-2-(7-(4-cyclopentyl-3-(trifluoromethyl)benzyloxy)-1,2,3,4-tetrahydrocyclopenta[b]indol-3-yl)acetic acid of Formula (Ia), (R)-2-(7-(4-cyclopentyl-3-(trifluoromethyl)benzyloxy)-1,2,3,4-tetrahydrocyclopenta[b]indol-3-yl)acetic acid of Formula (Ia) has an enantiomeric excess of about 95% or greater.

In some embodiments, after the step of isolating (R)-2-(7-(4-cyclopentyl-3-(trifluoromethyl)benzyloxy)-1,2,3,4-tetrahydrocyclopenta[b]indol-3-yl)acetic acid of Formula (Ia), (R)-2-(7-(4-cyclopentyl-3-(trifluoromethyl)benzyloxy)-1,2,3,4-tetrahydrocyclopenta[b]indol-3-yl)acetic acid of Formula (Ia) has an enantiomeric excess of about 98% or greater.

In some embodiments, after the step of isolating (R)-2-(7-(4-cyclopentyl-3-(trifluoromethyl)benzyloxy)-1,2,3,4-tetrahydrocyclopenta[b]indol-3-yl)acetic acid of Formula (Ia), (R)-2-(7-(4-cyclopentyl-3-(trifluoromethyl)benzyloxy)-1,2,3,4-tetrahydrocyclopenta[b]indol-3-yl)acetic acid of Formula (Ia) has an enantiomeric excess of about 99% or greater.

VIII. Hydrolyzing Step and Salt Formation Step

One aspect of the present invention pertains to processes for preparing an L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia):

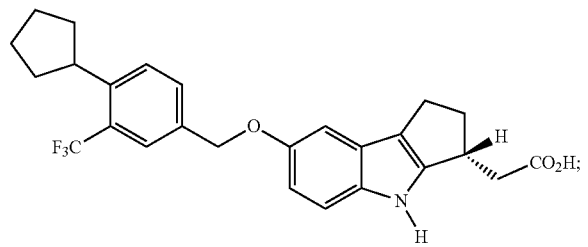

comprising the following steps:
a) hydrolyzing a compound of Formula (IIk):

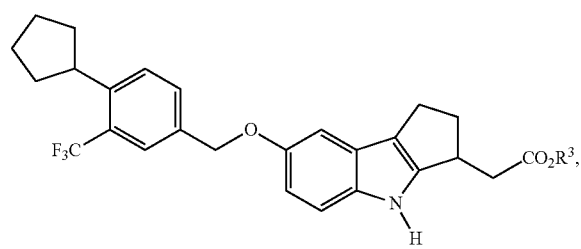

(IIk)

wherein $R^3$ is $C_1$-$C_6$ alkyl;
in the presence of a lipase and a hydrolyzing-step solvent to form (R)-2-(7-(4-cyclopentyl-3-(trifluoromethyl)benzyloxy)-1,2,3,4-tetrahydrocyclopenta[b]indol-3-yl)acetic acid of Formula (Ia); and
b) contacting (R)-2-(7-(4-cyclopentyl-3-(trifluoromethyl)benzyloxy)-1,2,3,4-tetrahydrocyclopenta[b]indol-3-yl)acetic acid (Formula (Ia)) with L-arginine or a salt thereof, in the presence of a contacting-step solvent and $H_2O$ to form the L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia).

VIIIa. Hydrolyzing Step a)
In some embodiments, $R^3$ is methyl or ethyl.
In some embodiments, $R^3$ is ethyl.
In some embodiments, the lipase is *Candida antarctica* lipase B.
In some embodiments, the lipase is immobilized *Candida antarctica* lipase B.
In some embodiments, the hydrolyzing-step solvent comprises a suitable solvent.
In some embodiments, the hydrolyzing-step solvent comprises dimethylformamide (DMF), dimethylacetamide (DMA), dimethylsulfoxide (DMSO), tetrahydrofuran (THF), or acetonitrile.
In some embodiments, the hydrolyzing-step solvent comprises acetonitrile.
In some embodiments, the step of hydrolyzing the compound of Formula (IIk) in the presence of a lipase and a hydrolyzing-step solvent, is conducted wherein:
the compound of Formula (IIIk) is:

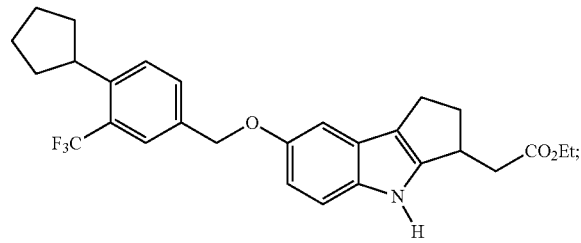 [SMILES: CCOC(=O)CC1CCc2c1[nH]c1ccc(OCc3ccc(C4CCCC4)c(C(F)(F)F)c3)cc21]

the lipase is immobilized *Candida antarctica* lipase B; and
the hydrolyzing-step solvent comprises acetonitrile.
In some embodiments, the step of hydrolyzing the compound of Formula (IIk) in the presence of a lipase and a hydrolyzing-step solvent is conducted in the presence of a phosphate buffer.

In some embodiments, the step of hydrolyzing the compound of Formula (IIk) in the presence of a lipase and a hydrolyzing-step solvent is conducted in the presence of a phosphate buffer at a pH of about 6.0 to about 9.0.
In some embodiments, the step of hydrolyzing the compound of Formula (IIk) in the presence of a lipase and a hydrolyzing-step solvent is conducted in the presence of a phosphate buffer at a pH of about 7.0 to about 8.5.
In some embodiments, the step of hydrolyzing the compound of Formula (IIk) in the presence of a lipase and a hydrolyzing-step solvent is conducted in the presence of a phosphate buffer at a pH of about 7.3 to about 8.3.
In some embodiments, the step of hydrolyzing the compound of Formula (IIk) in the presence of a lipase and a hydrolyzing-step solvent is conducted in the presence of a phosphate buffer at a pH of about 7.6 to about 8.0.
In some embodiments, the step of hydrolyzing the compound of Formula (IIk) in the presence of a lipase and a hydrolyzing-step solvent is conducted in the presence of a phosphate buffer at a pH of about 7.8.
In some embodiments, the phosphate buffer is a sodium phosphate buffer.
In some embodiments, the phosphate buffer is a potassium phosphate buffer.
In some embodiments, the step of hydrolyzing the compound of Formula (IIk) in the presence of a lipase and a hydrolyzing-step solvent is conducted at a temperature of about 0° C. to about 75° C.
In some embodiments, the step of hydrolyzing the compound of Formula (IIk) in the presence of a lipase and a hydrolyzing-step solvent is conducted at a temperature of about 20° C. to about 65° C.
In some embodiments, the step of hydrolyzing the compound of Formula (IIk) in the presence of a lipase and a hydrolyzing-step solvent is conducted at a temperature of about 30° C. to about 55° C.
In some embodiments, the step of hydrolyzing the compound of Formula (IIk) in the presence of a lipase and a hydrolyzing-step solvent is conducted at a temperature of about 35° C. to about 45° C.
In some embodiments, the step of hydrolyzing the compound of Formula (IIk) in the presence of a lipase and a hydrolyzing-step solvent, further comprises the step of isolating (R)-2-(7-(4-cyclopentyl-3-(trifluoromethyl)benzyloxy)-1,2,3,4-tetrahydrocyclopenta[b]indol-3-yl)acetic acid of Formula (Ia).
In some embodiments, after the step of isolating (R)-2-(7-(4-cyclopentyl-3-(trifluoromethyl)benzyloxy)-1,2,3,4-tetrahydrocyclopenta[b]indol-3-yl)acetic acid of Formula (Ia), (R)-2-(7-(4-cyclopentyl-3-(trifluoromethyl)benzyloxy)-1,2,3,4-tetrahydrocyclopenta[b]indol-3-yl)acetic acid of Formula (Ia) has an enantiomeric excess of about 95% or greater.
In some embodiments, after the step of isolating (R)-2-(7-(4-cyclopentyl-3-(trifluoromethyl)benzyloxy)-1,2,3,4-tetrahydrocyclopenta[b]indol-3-yl)acetic acid of Formula (Ia), (R)-2-(7-(4-cyclopentyl-3-(trifluoromethyl)benzyloxy)-1,2,3,4-tetrahydrocyclopenta[b]indol-3-yl)acetic acid of Formula (Ia) has an enantiomeric excess of about 98% or greater.
In some embodiments, after the step of isolating (R)-2-(7-(4-cyclopentyl-3-(trifluoromethyl)benzyloxy)-1,2,3,4-tetrahydrocyclopenta[b]indol-3-yl)acetic acid of Formula (Ia), (R)-2-(7-(4-cyclopentyl-3-(trifluoromethyl)benzyloxy)-1,2,3,4-tetrahydrocyclopenta[b]indol-3-yl)acetic acid of Formula (Ia) has an enantiomeric excess of about 99% or greater.
Representative HPLC Method for Chemical Purity Determination It is understood that the HPLC methods that retention times provided herein are approximate and are depend on numerous parameters that are know by those skilled in art, for example, the column, the column temperature, flow rate, solvent(s), the HPLC system; and the like. A standard for any of the compounds described herein can be readily prepared and the retention time easily determined for a HPLC system and conditions other than those described herein.

A representative HPLC method to determine the chemical purity of (R)-2-(7-(4-cyclopentyl-3-(trifluoromethyl)benzyloxy)-1,2,3,4-tetrahydrocyclopenta[b]indol-3-yl)acetic acid of Formula (Ia) or the L-arginine salt thereof is described below:

HPLC Conditions:
Column: Agilent SB-CN, 3.0×150 mm, 3.5 μm
Mobile Phase: A: $H_2O$ with 0.05% Trifluoroacetic Acid (TFA)
B: 70% Methanol/30% Acetonitrile/0.05% (TFA)
Needle Rinse Methanol
Flow Rate: 0.75 mL/min
Column Temperature: 50° C.
Detector Wavelength: 225 nm
Sample Injection Volume: 5 μL
Data acquisition time: 26 minutes
Sample Diluent Methanol
Sample Concentration 0.69 mg/mL

| Gradient (Using HPLC Conditions as Described Above For Determining Chemical Purity) | | | | | | | |
|---|---|---|---|---|---|---|---|
| Time (min) | | | | | | | |
| | 0 | 4 | 16 | 22 | 23 | 23.1 | 26 |
| % (A)* | 75 | 55 | 35 | 5 | 5 | 75 | 75 |
| % (B)* | 25 | 45 | 65 | 95 | 95 | 25 | 25 |

*(A) $H_2O$ with 0.05% Trifluoroacetic Acid (TFA) (B) 70% Methanol/30% Acetonitrile/0.05% (TFA)

| Compound Identification (Using HPLC Conditions as Described Above For Determining Chemical Purity) | |
|---|---|
| Compound ID | Retention Time (min)* |
| Compound of Formula (IIj, $R^3$ is ethyl) | 6.2 |
| Compound of Formula (IIb) | 10.9 |
| Impurity 1 | 11.6 |
| Impurity 2 | 12.2 |
| Compound of Formula (IIc) | 12.8 |
| Compound of Formula (IIi, $R^3$ is ethyl, E isomer) | 15.1 |
| Compound of Formula (IIi, $R^3$ is ethyl, Z isomer) | 16.8 |
| Compound of Formula (Ia) | 18.0 |
| Compound of Formula (IIk, $R^3$ is ethyl) | 19.6 |

*Retention times can vary depending on the HPLC system and conditions.

Representative HPLC Method for Enantiomeric Purity Determination

A representative HPLC method to determine the enantiomeric excess of (R)-2-(7-(4-cyclopentyl-3-(trifluoromethyl)benzyloxy)-1,2,3,4-tetrahydrocyclopenta[b]indol-3-yl)acetic acid of Formula (Ia) is described below:

HPLC Conditions:
Column: Chiralpak 1B, 5 μm, 4.6×250 mm
Mobile Phase: Hexanes/IPA/TFA (97:3:0.05)
Needle Rinse Ethanol
Flow Rate: 1.0 mL/min
Column Temperature: 30° C.
Detector Wavelength: 269 nm
Sample Injection Volume: 10 μL
Data acquisition time: 45 minutes
Sample Diluent Methanol
Sample Concentration 1.2 mg/mL The retention time for (R)-2-(7-(4-cyclopentyl-3-(trifluoromethyl)benzyloxy)-1,2,3,4-tetrahydrocyclopenta[b]indol-3-yl)acetic acid using the above conditions is about 24.9 minutes.

The retention time for (5)-2-(7-(4-cyclopentyl-3-(trifluoromethyl)benzyloxy)-1,2,3,4-tetrahydrocyclopenta[b]indol-3-yl)acetic acid using the above conditions is about 30.3 minutes.

VIIIb. Contacting Step b)—Salt Formation Step

In some embodiments, the contacting-step solvent comprises a suitable solvent.

In some embodiments, the contacting-step solvent comprises a $C_1$-$C_6$ alcohol.

In some embodiments, the contacting-step solvent comprises isopropyl alcohol.

In some embodiments, the contacting in step b), is conducted under a substantially inert atmosphere.

In some embodiments, the contacting in step b), is conducted under a substantially inert atmosphere comprising argon or nitrogen.

In some embodiments, the contacting in step b), is conducted under a substantially inert atmosphere comprising nitrogen.

In some embodiments, the molar ratio between (R)-2-(7-(4-cyclopentyl-3-(trifluoromethyl)benzyloxy)-1,2,3,4-tetrahydrocyclopenta[1)]indol-3-yl)acetic acid (Formula (Ia)) and L-arginine is about 1.0:1.0 to about 1.0:1.2.

In some embodiments, the molar ratio between (R)-2-(7-(4-cyclopentyl-3-(trifluoromethyl)benzyloxy)-1,2,3,4-tetrahydrocyclopenta[b]indol-3-yl)acetic acid (Formula (Ia)) and L-arginine is about 1.0:1.0.

In some embodiments, the contacting in step b) further comprises the step of adding an aqueous solution of L-arginine to a first contacting mixture comprising (R)-2-(7-(4-cyclopentyl-3-(trifluoromethyl)benzyloxy)-1,2,3,4-tetrahydrocyclopenta[1)]indol-3-yl)acetic acid (Formula (Ia)) and the $C_1$-$C_6$ alcohol to form a second contacting mixture.

In some embodiments, the first contacting mixture is at a temperature of about 45° C. to about 75° C.

In some embodiments, the first contacting mixture is at a temperature of about 50° C. to about 70° C.

In some embodiments, the first contacting mixture is at a temperature of about 55° C. to about 65° C.

In some embodiments, the first contacting mixture is at a temperature of about 60° C.

In some embodiments, further comprising the steps of cooling the second contacting mixture and crystallizing the L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia).

In some embodiments, the cooling is conducted at a rate of about 0.04° C./minute to about 4.0° C./minute.

In some embodiments, the cooling is conducted at a rate of about 0.1° C./minute to about 2.0° C./minute.

In some embodiments, the cooling is conducted at a rate of about 0.4° C./minute to about 1.0° C./minute.

In some embodiments, the cooling is conducted at a rate of about 0.4° C./minute.

In some embodiments, contacting (R)-2-(7-(4-cyclopentyl-3-(trifluoromethyl)benzyloxy)-1,2,3,4-tetrahydrocyclopenta[b]indol-3-yl)acetic acid (Formula (Ia)) with L-arginine or a salt thereof, in the presence of a contacting-step solvent and H₂O, further comprises the step of isolating the L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia).

In some embodiments, the isolating is conducted by filtration.

In some embodiments, after isolating, the L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia) has a purity of about 95% or greater as determined by HPLC.

In some embodiments, after isolating, the L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia) has a purity of about 98% or greater as determined by HPLC.

In some embodiments, after isolating, the L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia) has a purity of about 99% or greater as determined by HPLC.

In some embodiments, after isolating the L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia), the (R)-2-(7-(4-cyclopentyl-3-(trifluoromethyl)benzyloxy)-1,2,3,4-tetrahydrocyclopenta[b]indol-3-yl) acetic acid of Formula (Ia) has an enantiomeric excess of about 95% or greater.

In some embodiments, after isolating the L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia), the (R)-2-(7-(4-cyclopentyl-3-(trifluoromethyl)benzyloxy)-1,2,3,4-tetrahydrocyclopenta[b]indol-3-yl) acetic acid of Formula (Ia) has an enantiomeric excess of about 98% or greater.

In some embodiments, after isolating the L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia), the (R)-2-(7-(4-cyclopentyl-3-(trifluoromethyl)benzyloxy)-1,2,3,4-tetrahydrocyclopenta[b]indol-3-yl) acetic acid of Formula (Ia) has an enantiomeric excess of about 99% or greater.

A representative HPLC method to determine the enantiomeric excess of (R)-2-(7-(4-cyclopentyl-3-(trifluoromethyl)benzyloxy)-1,2,3,4-tetrahydrocyclopenta[b]indol-3-yl)acetic acid of Formula (Ia) is as described above.

A representative HPLC method for the analysis of L-arginine for the L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia) is described below.

Representative HPLC Method for Analysis of L-Arginine

HPLC Conditions

Column: SeQuant ZIC®-HILIC, 2.1×150 mm, 5 vim

Mobile Phase: (A) 20 mM Ammonium formate, pH 6.2

(B) Acetonitrile

Needle Rinse Methanol

Flow Rate: 0.4 mL/min

Column Temperature: 30° C.

Detector Wavelength: 206 nm

Sample Injection Volume: 5 μL

Data acquisition time: 15 minutes

Sample Diluent Methanol

Sample Concentration 4.0 mg/mL

| Gradient Program | | | | | |
|---|---|---|---|---|---|
| Time (min) | 0 | 8 | 10 | 10.1 | 15 |
| % (A) | 20 | 80 | 80 | 20 | 20 |
| % (B) | 80 | 20 | 20 | 80 | 80 |

The retention time of (R)-2-(7-(4-cyclopentyl-3-(trifluoromethyl)benzyloxy)-1,2,3,4-tetrahydrocyclopenta[b]indol-3-yl)acetic acid present in the L-arginine salt of (R)-2-(7-(4-cyclopentyl-3-(trifluoromethyl)benzyloxy)-1,2,3,4-tetrahydrocyclopenta[b]indol-3-yl)acetic acid using the above conditions is about 1.2 minutes.

The retention time of L-arginine present in the L-arginine salt of (R)-2-(7-(4-cyclopentyl-3-(trifluoromethyl)benzyloxy)-1,2,3,4-tetrahydrocyclopenta[b]indol-3-yl)acetic acid using the above conditions is about 8.6 minutes.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatography (HPLC) or thin layer chromatography.

In some embodiments, preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, *Protective Groups in Organic Synthesis*, 3$^{rd}$ Ed., Wiley & Sons, 1999.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as: carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, 1,2-dichlorobenzene, 1,3-dichlorobenzene, 1,4-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluorethane and hexafluoroethane.

Suitable solvents can include ether solvents, such as: dimethoxymethane, tetrahydrofuran, 2-methyltetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, or t-butyl methyl ether.

Suitable solvents can include protic solvents, such as: water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, isobutyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable solvents can include aprotic solvents, such as: benzene, cyclohexane, pentane, hexane, toluene, cycloheptane, methylcyclohexane, heptane, ethylbenzene, o, m-, or p-xylene, octane, indane, nonane, naphthalene, tetrahydrofuran, acetonitrile, dimethyl sulfoxide, propionitrile, ethyl formate, methyl acetate, hexachloroacetone, acetone, ethyl methyl ketone, ethyl acetate, isopropyl acetate, sulfolane, 1,3-dimethyl-3,4,5,6-tetrahydro-2(1H)-pyrimidinone, 1,3-dimethyl-2-imidazolidinone, N-methylpyrrolidinone, tetramethylurea, nitromethane, and nitrobenzene, and amides, including but not limited to, N,N-dimethylformamide, N,N-dimethylacetamide, formamide, N-methylacetamide, N-methylformamide, N,N-dimethylpropionamide, and hexamethylphosphoramide. It is understood by a person of ordinary skill in the art that that the term amide refers to the following formula:

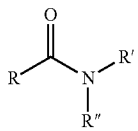

wherein R, R', and R" may be the same or different. In some embodiments, R, R', and R" are each independently selected from H and $C_1$-$C_6$ alkyl. In some embodiments, R, R', and R" are each independently selected from H and $C_1$-$C_4$ alkyl. In some embodiments, R, R', and R" are each independently selected from H and $C_1$-$C_2$ alkyl.

Supercritical carbon dioxide can also be used as a solvent.

The reactions of the processes described herein can be carried out at appropriate temperatures which can be readily determined by one skilled in the art. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures).

The reactions of the processes described herein can be carried out in air or under an inert atmosphere. Typically, reactions containing reagents or products that are substantially reactive with air can be carried out using air-sensitive synthetic techniques that are well known to one skilled in the art.

In some embodiments, preparation of compounds can involve the addition of acids or bases to effect, for example, catalysis of a desired reaction or formation of salt forms such as acid addition salts.

Example acids can be inorganic or organic acids. Inorganic acids include hydrochloric acid, hydrobromic acid, sulfuric acid, phosphoric acid, and nitric acid. Organic acids include formic acid, acetic acid, trifluoroacetic acid, propionic acid, butanoic acid, methanesulfonic acid, p-toluene sulfonic acid, benzenesulfonic acid, propiolic acid, butyric acid, 2-butynoic acid, vinyl acetic acid, pentanoic acid, hexanoic acid, heptanoic acid, octanoic acid, nonanoic acid and decanoic acid.

Example bases include lithium hydroxide, sodium hydroxide, potassium hydroxide, lithium carbonate, sodium carbonate, and potassium carbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include sodium and potassium salts of methyl, ethyl, n-propyl, isopropyl, n-butyl, t-butyl, trimethylsilyl and cyclohexyl substituted amides.

The compounds described herein can be asymmetric (e.g., having one or more stereocenters). All stereoisomers, such as enantiomers and diastereomers, are intended unless otherwise indicated. Salts of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis.

The processes described herein can be stereoselective such that any given reaction starting with one or more chiral reagents enriched in one stereoisomer forms a product that is also enriched in one stereoisomer. The reaction can be conducted such that the product of the reaction substantially retains one or more chiral centers present in the starting materials. The reaction can also be conducted such that the product of the reaction contains a chiral center that is substantially inverted relative to a corresponding chiral center present in the starting materials.

Resolution of racemic mixtures of compounds can be carried out by any of numerous methods known in the art. An example method includes fractional recrystallization (for example, diastereomeric salt resolution) using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of β-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

The compounds described herein and salts thereof can also include all isotopes of atoms occurring in the intermediates or final compounds or salts thereof. Isotopes include those atoms having the same atomic number but different mass numbers. For example, isotopes of hydrogen include tritium and deuterium.

The compounds described herein and salts thereof can also include tautomeric forms, such as keto-enol tautomers. Tautomeric forms can be in equilibrium or sterically locked into one form by appropriate substitution.

Upon carrying out preparation of compounds according to the processes described herein, the usual isolation and purification operations such as concentration, filtration, extraction, solid-phase extraction, recrystallization, chromatography, and the like may be used, to isolate the desired products.

Uses and Intermediates

One aspect of the present invention provides, inter alia, intermediates prepared by any of the processes described herein.

The present invention further provides pharmaceutical compositions comprising compounds prepared by any of the processes as described herein.

The present invention further provides processes of preparing a pharmaceutical composition comprising admixing Compound of Formula (Ia) or a salt thereof with a pharmaceutically acceptable carrier, wherein the Compound of Formula (Ia) or a salt thereof is prepared by any of the processes as described herein.

The present invention further provides intermediates, as described herein, for use in processes for preparing pharmaceutical compositions for treating an S1P1 receptor-associated disorder in an individual.

The present invention further provides uses of compounds, as described herein, in processes for preparing pharmaceutical compositions for treating an S1P1 receptor-associated disorder.

One aspect of the present invention pertains to compounds represented by any of the formulae described herein.

One aspect of the present invention pertains to compounds represented by any of the formulae described herein for use in a process for preparing a pharmaceutical composition for treating an S1P1 receptor-associated disorder in an individual.

One aspect of the present invention pertains to compounds represented by any of the formulae described herein prepared according to any of the processes described herein.

One aspect of the present invention pertains to compounds represented by any of the formulae described herein prepared according to any of the processes described herein, for use in a process for preparing a pharmaceutical composition for treating an S1P1 receptor-associated disorder in an individual.

Compound of Formula (IIb)

One aspect of the present invention pertains to a compound that is 1-cyclopentyl-2-(trifluoromethyl)benzene of Formula (IIb):

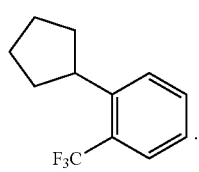

One aspect of the present invention pertains to a compound that is 1-cyclopentyl-2-(trifluoromethyl)benzene of Formula (IIb):

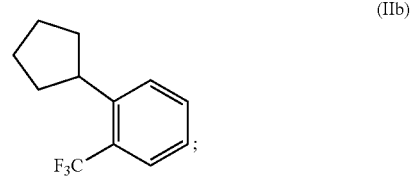 [SMILES: FC(F)(F)c1ccccc1C1CCCC1]

for use in a process for preparing a pharmaceutical composition for treating an S1P1 receptor-associated disorder in an individual.

One aspect of the present invention pertains to a compound that is 1-cyclopentyl-2-(trifluoromethyl)benzene of Formula (IIb) prepared according to any of the processes described herein.

One aspect of the present invention pertains to a compound that is 1-cyclopentyl-2-(trifluoromethyl)benzene of Formula (IIb) prepared according to any of the processes described herein, for use in a process for preparing a pharmaceutical composition for treating an S1P1 receptor-associated disorder in an individual.

Compound of Formula (IIc)

One aspect of the present invention pertains to a compound that is 4-(chloromethyl)-1-cyclopentyl-2-(trifluoromethyl)benzene of Formula (IIc):

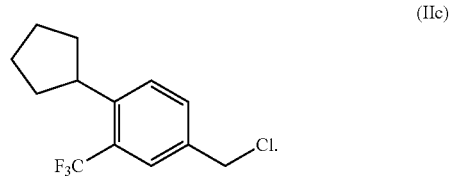 [SMILES: FC(F)(F)c1cc(CCl)ccc1C1CCCC1]

One aspect of the present invention pertains to a compound that is 4-(chloromethyl)-1-cyclopentyl-2-(trifluoromethyl)benzene of Formula (IIc):

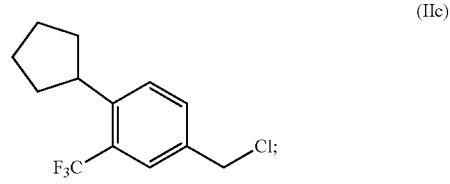 [SMILES: FC(F)(F)c1cc(CCl)ccc1C1CCCC1]

for use in a process for preparing a pharmaceutical composition for treating an S1P1 receptor-associated disorder in an individual.

One aspect of the present invention pertains to a compound that is 4-(chloromethyl)-1-cyclopentyl-2-(trifluoromethyl)benzene of Formula (IIc) prepared according to any of the processes described herein.

One aspect of the present invention pertains to a compound that is 4-(chloromethyl)-1-cyclopentyl-2-(trifluoromethyl)benzene of Formula (IIc) prepared according to any of the processes described herein, for use in a process for preparing a pharmaceutical composition for treating an S1P1 receptor-associated disorder in an individual.

Compounds of Formula (IIi)

One aspect of the present invention pertains to a compound of Formula (IIi):

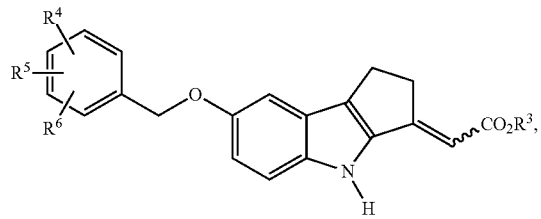

(IIi)

wherein $R^3$ is $C_1$-$C_6$ alkyl; and $R^4$, $R^5$, and $R^6$ are each selected independently from the group consisting of H, $C_1$-$C_4$ alkyl, $C_1$-$C_4$ alkoxy, halogen, $C_1$-$C_4$ haloalkyl, $C_1$-$C_4$ haloalkoxy, and nitro.

In some embodiments, $R^3$ is ethyl.

In some embodiments, $R^4$, $R^5$, and $R^6$ are each H.

In some embodiments, $R^3$ is ethyl, and $R^4$, $R^5$, and $R^6$ are each H.

One aspect of the present invention pertains to uses of a compound of Formula (IIi):

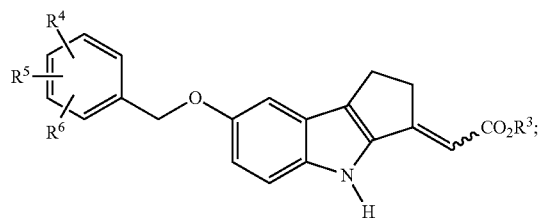

(IIi)

wherein $R^3$ is $C_1$-$C_6$ alkyl; and $R^4$, $R^5$, and $R^6$ are each selected independently from the group consisting of H, $C_1$-$C_4$ alkyl, $C_1$-$C_4$ alkoxy, halogen, $C_1$-$C_4$ haloalkyl, $C_1$-$C_4$ haloalkoxy, and nitro; in the manufacture of a medicament for treating an S1P1 receptor-associated disorder.

One aspect of the present invention pertains to uses of a compound of the formula:

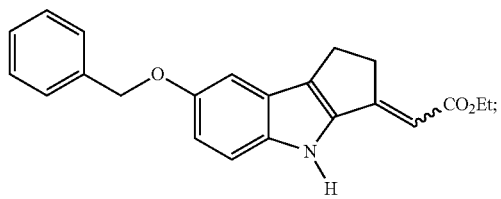 [SMILES: CCOC(=O)C=C1CCc2c1[nH]c1ccc(OCc3ccccc3)cc21]

in the manufacture of a medicament for treating an S1P1 receptor-associated disorder.

One aspect of the present invention pertains to uses of a compound of Formula (IIi):

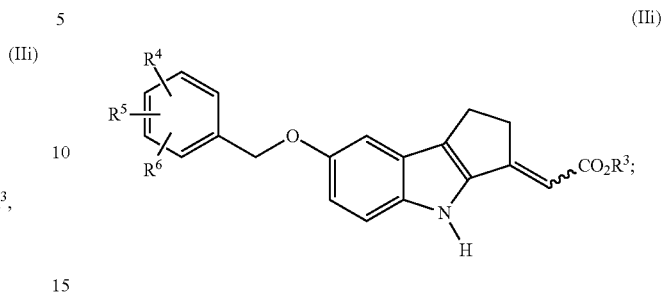

(IIi)

wherein $R^3$ is $C_1$-$C_6$ alkyl; and $R^4$, $R^5$, and $R^6$ are each selected independently from the group consisting of H, $C_1$-$C_4$ alkyl, $C_1$-$C_4$ alkoxy, halogen, $C_1$-$C_4$ haloalkyl, $C_1$-$C_4$ haloalkoxy, and nitro; in a process for preparing a pharmaceutical composition for treating an S1P1 receptor-associated disorder in an individual.

One aspect of the present invention pertains to a compound of Formula (IIi):

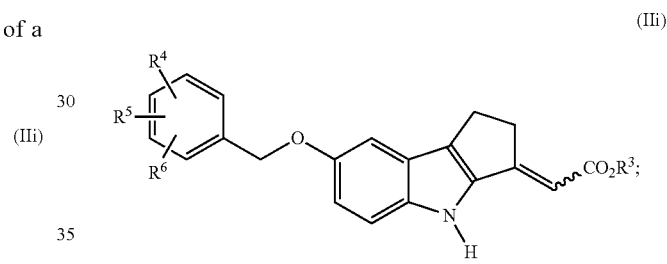

(IIi)

wherein $R^3$ is $C_1$-$C_6$ alkyl; and $R^4$, $R^5$, and $R^6$ are each selected independently from the group consisting of H, $C_1$-$C_4$ alkyl, $C_1$-$C_4$ alkoxy, halogen, $C_1$-$C_4$ haloalkyl, $C_1$-$C_4$ haloalkoxy, and nitro; for use in a process for preparing a pharmaceutical composition for treating an S1P1 receptor-associated disorder in an individual.

One aspect of the present invention pertains to a compound of Formula (IIi) prepared according to any of the processes described herein.

One aspect of the present invention pertains to a compound of Formula (IIi) prepared according to any of the processes described herein, for use in a process for preparing a pharmaceutical composition for treating an S1P1 receptor-associated disorder in an individual.

Compounds of Formula (IIj)

One aspect of the present invention pertains to a compound of Formula (IIj):

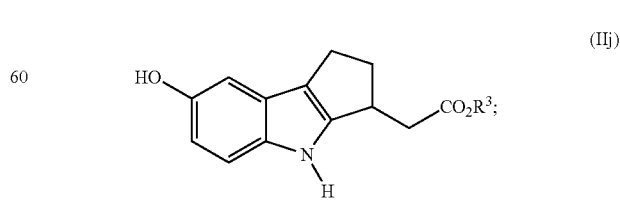

(IIj)

wherein $R^3$ is $C_1$-$C_6$ alkyl.

One aspect of the present invention pertains to a compound of Formula (IIj):

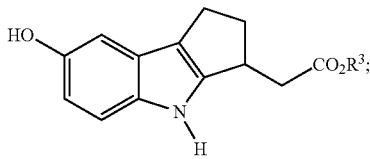

(IIj)

wherein $R^3$ is $C_1$-$C_6$ alkyl; for use in a process for preparing a pharmaceutical composition for treating an S1P1 receptor-associated disorder in an individual.

One aspect of the present invention pertains to a compound of Formula (IIj) prepared according to any of the processes described herein.

One aspect of the present invention pertains to a compound of Formula (IIj) prepared according to any of the processes described herein, for use in a process for preparing a pharmaceutical composition for treating an S1P1 receptor-associated disorder in an individual.

In some embodiments, $R^3$ is ethyl.
In some embodiments, $R^3$ is other than ethyl.
In some embodiments, $R^3$ is other than methyl.

Compounds of Formula (IIk)

One aspect of the present invention pertains to a compound of Formula (IIk):

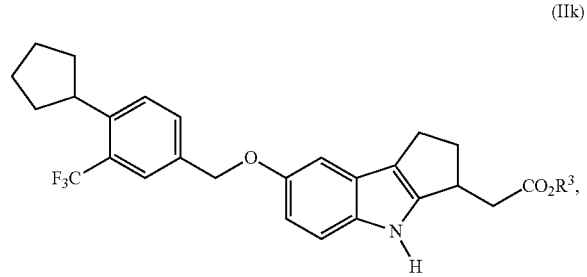

(IIk)

wherein $R^3$ is $C_1$-$C_6$ alkyl.

One aspect of the present invention pertains to a compound of Formula (IIk):

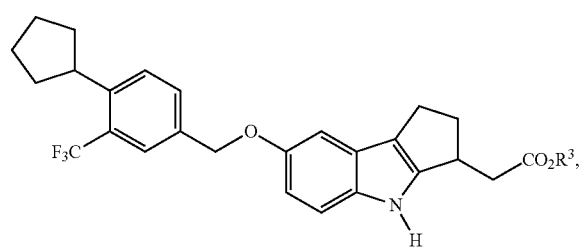

(IIk)

wherein $R^3$ is $C_1$-$C_6$ alkyl; for use in a process for preparing a pharmaceutical composition for treating an S1P1 receptor-associated disorder in an individual.

One aspect of the present invention pertains to a compound of Formula (IIk) prepared according to any of the processes described herein.

One aspect of the present invention pertains to a compound of Formula (IIk) prepared according to any of the processes described herein, for use in a process for preparing a pharmaceutical composition for treating an S1P1 receptor-associated disorder in an individual.

In some embodiments, $R^3$ is ethyl.
In some embodiments, $R^3$ is other than ethyl.
In some embodiments, $R^3$ is other than methyl.

Compounds of Formula (Ia)

One aspect of the present invention pertains to pharmaceutical compositions comprising (R)-2-(7-(4-cyclopentyl-3-(trifluoromethyl)benzyloxy)-1,2,3,4-tetrahydrocyclopenta[b]indol-3-yl)acetic acid of Formula (Ia), or a salt thereof:

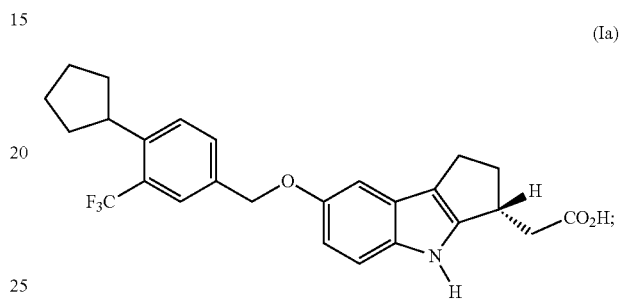

(Ia)

and a pharmaceutically acceptable carrier, wherein the (R)-2-(7-(4-cyclopentyl-3-(trifluoromethyl)benzyloxy)-1,2,3,4-tetrahydrocyclopenta[b]indol-3-yl)acetic acid of Formula (Ia) is prepared according to any of the processes described herein.

In some embodiments, (R)-2-(7-(4-cyclopentyl-3-(trifluoromethyl)benzyloxy)-1,2,3,4-tetrahydrocyclopenta[b]indol-3-yl)acetic acid of Formula (Ia) is used for treating an S1P1 receptor-associated disorder in an individual, wherein (R)-2-(7-(4-cyclopentyl-3-(trifluoromethyl)benzyloxy)-1,2,3,4-tetrahydrocyclopenta[b]indol-3-yl)acetic acid of Formula (Ia) is prepared according to any of the processes described herein.

In some embodiments, the pharmaceutical composition comprising (R)-2-(7-(4-cyclopentyl-3-(trifluoromethyl)benzyloxy)-1,2,3,4-tetrahydrocyclopenta[b]indol-3-yl)acetic acid of Formula (Ia) is used for treating an S1P1 receptor-associated disorder in an individual, wherein (R)-2-(7-(4-cyclopentyl-3-(trifluoromethyl)benzyloxy)-1,2,3,4-tetrahydrocyclopenta[b]indol-3-yl)acetic acid of Formula (Ia) is prepared according to any of the processes described herein.

One aspect of the present invention pertains to processes of preparing a pharmaceutical composition comprising admixing (R)-2-(7-(4-cyclopentyl-3-(trifluoromethyl)benzyloxy)-1,2,3,4-tetrahydrocyclopenta[b]indol-3-yl)acetic acid of Formula (Ia), or a salt thereof:

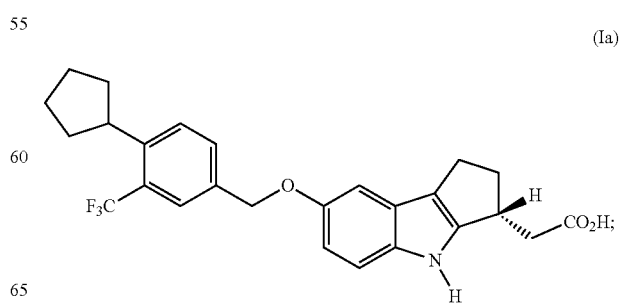

(Ia)

and a pharmaceutically acceptable carrier, wherein the (R)-2-(7-(4-cyclopentyl-3-(trifluoromethyl)benzyloxy)-1,2,3,4-tetrahydrocyclopenta[b]indol-3-yl)acetic acid of Formula (Ia) is prepared according to any of the processes described herein.

One aspect of the present invention pertains to (R)-2-(7-(4-cyclopentyl-3-(trifluoromethyl)benzyloxy)-1,2,3,4-tetrahydrocyclopenta indol-3-yl)acetic acid of Formula (Ia) or a salt thereof, prepared according to any of the processes described herein.

One aspect of the present invention pertains to (R)-2-(7-(4-cyclopentyl-3-(trifluoromethyl)benzyloxy)-1,2,3,4-tetrahydrocyclopenta[b]indol-3-yl)acetic acid of Formula (Ia) or a salt thereof, prepared according to any of the processes described herein, for use in a process for preparing a pharmaceutical composition for treating an S1P1 receptor-associated disorder in an individual.

L-Arginine salt of Compound of Formula (Ia)

One aspect of the present invention pertains to pharmaceutical compositions comprising an L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia):

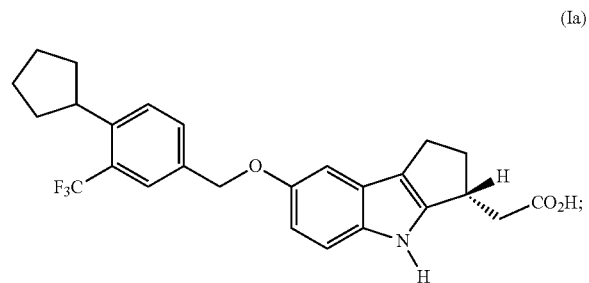 [SMILES: O=C(O)C[C@H]1CCc2c1[nH]c1ccc(OCc3ccc(C4CCCC4)c(C(F)(F)F)c3)cc21]

(Ia)

and a pharmaceutically acceptable carrier, wherein the L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia) is prepared according to any of the processes described herein.

In some embodiments, L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia) is used for treating an S1P1 receptor-associated disorder in an individual, wherein the L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia) is prepared according to any of the processes described herein.

In some embodiments, the pharmaceutical composition comprising an L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia) is used for treating an S1P1 receptor-associated disorder in an individual, wherein the L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia) is prepared according to any of the processes described herein.

One aspect of the present invention pertains to processes of preparing a pharmaceutical composition comprising admixing an L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia):

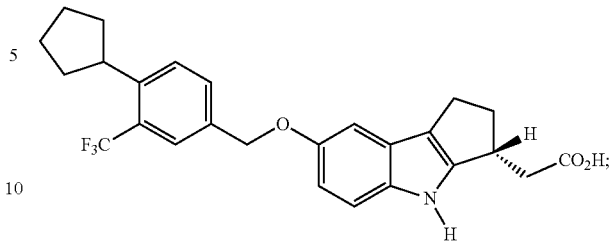

(Ia)

and a pharmaceutically acceptable carrier, wherein the L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia) is prepared according to any of the processes described herein.

One aspect of the present invention pertains to the L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia) or a salt thereof, prepared according to any of the processes described herein.

One aspect of the present invention pertains to the L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia) or a salt thereof, prepared according to any of the processes described herein, for use in a process for preparing a pharmaceutical composition for treating an S1P1 receptor-associated disorder in an individual.

Indications

S1P receptor agonists having agonist activity on the S1P1 receptor have been shown to rapidly and reversibly induce lymphopenia (also referred to as peripheral lymphocyte lowering (PLL); Hale et al., Bioorg. Med. Chem. Lett., 14:3351-3355, 2004). This is attended by clinically useful immunosuppression by virtue of sequestering T- and B-cells in secondary lymphoid tissue (lymph nodes and Peyer's patches) and thus apart from sites of inflammation and organ grafts (Rosen et al., Immunol. Rev., 195:160-177, 2003; Schwab et al., Nature Immunol., 8:1295-1301, 2007). This lymphocyte sequestration, for example in lymph nodes, is thought to be a consequence of concurrent agonist-driven functional antagonism of the S1P1 receptor on T-cells (whereby the ability of S1P to mobilize T-cell egress from lymph nodes is reduced) and persistent agonism of the S1P1 receptor on lymph node endothelium (such that barrier function opposing transmigration of lymphocytes is increased) (Matloubian et al., Nature, 427:355-360, 2004; Baumruker et al., Expert Opin. Investig. Drugs, 16:283-289, 2007). It has been reported that agonism of the S1P1 receptor alone is sufficient to achieve lymphocyte sequestration (Sanna et al., J Biol. Chem., 279:13839-13848, 2004) and that this occurs without impairment of immune responses to systemic infection (Brinkmann et al., Transplantation, 72:764-769, 2001; Brinkmann et al., Transplant Proc., 33:530-531, 2001).

That agonism of endothelial S1P1 receptors has a broader role in promoting vascular integrity is supported by work implicating the S1P1 receptor in capillary integrity in mouse skin and lung (Sanna et al., Nat Chem. Biol., 2:434-441, 2006). Vascular integrity can be compromised by inflammatory processes, for example as may derive from sepsis, major trauma and surgery so as to lead to acute lung injury or respiratory distress syndrome (Johan Groeneveld, Vascul. Pharmacol., 39:247-256, 2003).

An exemplary S1P receptor agonist having agonist activity on the S1P1 receptor is FTY720 (fingolimod), an immunosuppressive agent currently in clinical trials (Martini et al., *Expert Opin. Investig. Drugs*, 16:505-518, 2007). FTY720 acts as a prodrug which is phosphorylated in vivo; the phosphorylated derivative is an agonist for SIP 1, S1P3, S1P4, and S1P5 receptors (but not the S1P2 receptor) (Chiba, *Pharmacology & Therapeutics*, 108:308-319, 2005). FTY720 has been shown to rapidly and reversibly induce lymphopenia (also referred to as peripheral lymphocyte lowering (PLL); Hale et al., *Bioorg. Med. Chem. Lett.*, 14:3351-3355, 2004). This is attended by clinically useful immunosuppression by virtue of sequestering T- and B-cells in secondary lymphoid tissue (lymph nodes and Peyer's patches) and thus apart from sites of inflammation and organ grafts (Rosen et al., *Immunol. Rev.*, 195:160-177, 2003; Schwab et al., *Nature Immunol.*, 8:1295-1301, 2007).

In clinical trials, FTY720 elicited an adverse event (i.e., transient asymptomatic bradycardia) due to its agonism of the S1P3 receptor (Budde et al., *J. Am. Soc. Nephrol.*, 13:1073-1083, 2002; Sanna et al., *J. Biol. Chem.*, 279:13839-13848, 2004; Ogawa et al., *BBRC*, 361:621-628, 2007).

FTY720 has been reported to have therapeutic efficacy in at least: a rat model for autoimmune myocarditis and a mouse model for acute viral myocarditis (Kiyabayashi et al., *J. Cardiovasc. Pharmacol.*, 35:410-416, 2000; Miyamoto et al., *J. Am. Coll. Cardiol.*, 37:1713-1718, 2001); mouse models for inflammatory bowel disease including colitis (Mizushima et al., *Inflamm. Bowel Dis.*, 10:182-192, 2004; Deguchi et al., *Oncology Reports*, 16:699-703, 2006; Fujii et al., *Am. J. Physiol. Gastrointest. Liver Physiol.*, 291:G267-G274, 2006; Daniel et al., *J. Immunol.*, 178:2458-2468, 2007); a rat model for progressive mesangioproliferative glomerulonephritis (Martini et al., *Am. J. Physiol. Renal Physiol.*, 292:F1761-F1770, 2007); a mouse model for asthma, suggested to be primarily through the S1P1 receptor on the basis of work using the S1P1 receptor agonist SEW2871 (Idzko et al, J. Clin. Invest., 116:2935-2944, 2006); a mouse model for airway inflammation and induction of bronchial hyperresponsiveness (Sawicka et al., *J. Immunol.*, 171; 6206-6214, 2003); a mouse model for atopic dermatitis (Kohno et al., *Biol. Pharm. Bull.*, 27:1392-1396, 2004); a mouse model for ischemia-reperfusion injury (Kaudel et al., *Transplant. Proc*, 39:499-502, 2007); a mouse model for systemic lupus erythematosus (SLE) (Okazaki et al., *J. Rheumatol.*, 29:707-716, 2002; Herzinger et al, Am. J. Clin. Dermatol., 8:329-336, 2007); rat models for rheumatoid arthritis (Matsuura et al., *Int. J. Immunopharmacol.*, 22:323-331, 2000; Matsuura et al., *Inflamm. Res.*, 49:404-410, 2000); a rat model for autoimmune uveitis (Kurose et al., *Exp. Eye Res.*, 70:7-15, 2000); mouse models for type I diabetes (Fu et al, *Transplantation*, 73:1425-1430, 2002; Maki et al., *Transplantation*, 74:1684-1686, 2002; Yang et al., *Clinical Immunology*, 107:30-35, 2003; Maki et al., *Transplantation*, 79:1051-1055, 2005); mouse models for atherosclerosis (Nofer et al., *Circulation*, 115:501-508, 2007; Keul et al., *Arterioscler. Thromb. Vasc. Biol.*, 27:607-613, 2007); a rat model for brain inflammatory reaction following traumatic brain injury (TBI) (Zhang et al., *J. Cell. Mol. Med.*, 11:307-314, 2007); and mouse models for graft coronary artery disease and graft-versus-host disease (GVHD) (Hwang et al., *Circulation*, 100:1322-1329, 1999; Taylor et al., *Blood*, 110:3480-3488, 2007). In vitro results suggest that FTY720 may have therapeutic efficacy for β-amyloid-related inflammatory diseases including Alzheimer's disease (Kaneider et al., *FASEB J.*, 18:309-311, 2004). KRP-203, an S1P receptor agonist having agonist activity on the S1P1 receptor, has been reported to have therapeutic efficacy in a rat model for autoimmune myocarditis (Ogawa et al., *BBRC*, 361:621-628, 2007). Using the S1P1 receptor agonist SEW2871, it has been shown that agonism of endothelial S1P1 receptors prevents proinflammatory monocyte/endothelial interactions in type I diabetic vascular endothelium (Whetzel et al., *Circ. Res.*, 99:731-739, 2006) and protects the vasculature against TNFα-mediated monocyte/endothelial interactions (Bolick et al., *Arterioscler. Thromb. Vasc. Biol.*, 25:976-981, 2005).

Additionally, FTY720 has been reported to have therapeutic efficacy in experimental autoimmune encephalomyelitis (EAE) in rats and mice, a model for human multiple sclerosis (Brinkmann et al., *J. Biol. Chem.*, 277:21453-21457, 2002; Fujino et al., *J. Pharmacol. Exp. Ther.*, 305:70-77, 2003; Webb et al., *J. Neuroimmunol.*, 153:108-121, 2004; Rausch et al., *J. Magn. Reson. Imaging*, 20:16-24, 2004; Kataoka et al., *Cellular & Molecular Immunology*, 2:439-448, 2005; Brinkmann et al., *Pharmacology & Therapeutics*, 115:84-105, 2007; Baumruker et al., *Expert Opin. Investig. Drugs*, 16:283-289, 2007; Balatoni et al., *Brain Research Bulletin*, 74:307-316, 2007). Furthermore, FTY720 has been found to have therapeutic efficacy for multiple sclerosis in clinical trials. In Phase II clinical trials for relapsing-remitting multiple sclerosis, FTY720 was found to reduce the number of lesions detected by magnetic resonance imaging (MRI) and clinical disease activity in patients with multiple sclerosis (Kappos et al., *N Engl. J. Med.*, 355:1124-1140, 2006; Martini et al., *Expert Opin. Investig. Drugs*, 16:505-518, 2007; Zhang et al., *Mini-Reviews in Medicinal Chemistry*, 7:845-850, 2007; Brinkmann, *Pharmacology & Therapeutics*, 115:84-105, 2007). FTY720 is currently in Phase III studies of remitting-relapsing multiple sclerosis (Brinkmann, *Pharmacology & Therapeutics*, 115:84-105, 2007; Baumruker et al., *Expert. Opin. Investig. Drugs*, 16:283-289, 2007; Dev et al., *Pharmacology and Therapeutics*, 117:77-93, 2008).

Recently, FTY720 has been reported to have anti-viral activity. Specific data has been presented in the lymphocytic choriomeningitis virus (LCMV) mouse model, wherein the mice were infected with either the Armstrong or the clone 13 strain of LCMV (Premenko-Lanier et al., *Nature*, 454, 894, 2008).

FTY720 has been reported to impair migration of dendritic cells infected with *Francisella tularensis* to the mediastinal lymph node, thereby reducing the bacterial colonization of it. *Francisella tularensis* is associated with tularemia, ulceroglandular infection, respiratory infection and a typhoidal disease (E. Bar-Haim et al., PLoS Pathog 4(11): e1000211. doi:10.1371/journal.ppat.1000211, 2008).

It has also been recently reported that a short-term high dose of FTY720 rapidly reduced ocular infiltrates in experimental autoimmune uveoretinitis. When given in the early stages of ocular inflammation, FTY720 rapidly prevented retinal damage. It was reported to not only prevent infiltration of target organs, but also reduce existing infiltration (Raveney et al., *Arch. Ophthalmol.* 126(10), 1390, 2008).

It has been reported that treatment with FTY720 relieved ovariectomy-induced osteoporosis in mice by reducing the number of mature osteoclasts attached to the bone surface. The data provided evidence that SIP controled the migratory behaviour of osteoclast precursors, dynamically regulating bone mineral homeostasis (Ishii et al., *Nature,* 458(7237), 524-528, 2009).

Agonism of the S1P1 receptor has been implicated in enhancement of survival of oligodendrocyte progenitor cells. Survival of oligodendrocyte progenitor cells is a required component of the remyelination process. Remyelination of multiple sclerosis lesions is considered to promote recovery from clinical relapses. (Miron et al., *Ann. Neurol.*, 63:61-71, 2008; Coelho et al., *J. Pharmacol. Exp. Ther.*, 323:626-635, 2007; Dev et al., *Pharmacology and Therapeutics*, 117:77-93, 2008). It also has been shown that the S1P1 receptor plays a role in platelet-derived growth factor (PDGF)-induced oligodendrocyte progenitor cell mitogenesis (Jung et al., *Glia*, 55:1656-1667, 2007).

Agonism of the S1P1 receptor has also been reported to mediate migration of neural stem cells toward injured areas of the central nervous system (CNS), including in a rat model of spinal cord injury (Kimura et al., *Stem Cells*, 25:115-124, 2007).

Agonism of the S1P1 receptor has been implicated in the inhibition of keratinocyte proliferation (Sauer et al., *J. Biol. Chem.*, 279:38471-38479, 2004), consistent with reports that SIP inhibits keratinocyte proliferation (Kim et al., *Cell Signal*, 16:89-95, 2004). The hyperproliferation of keratinocytes at the entrance to the hair follicle, which can then become blocked, and an associated inflammation are significant pathogenetic factors of acne (Koreck et al., *Dermatology*, 206:96-105, 2003; Webster, *Cutis*, 76:4-7, 2005).

FTY720 has been reported to have therapeutic efficacy in inhibiting pathologic angiogenesis, such as that as may occur in tumor development. Inhibition of angiogenesis by FTY720 is thought to involve agonism of the S1P1 receptor (Oo et al., *J. Biol. Chem.*, 282; 9082-9089, 2007; Schmid et al., *J. Cell Biochem.*, 101:259-270, 2007). FTY720 has been reported to have therapeutic efficacy for inhibiting primary and metastatic tumor growth in a mouse model of melanoma (LaMontagne et al., *Cancer Res.*, 66:221-231, 2006). FTY720 has been reported to have therapeutic efficacy in a mouse model for metastatic hepatocellular carcinoma (Lee et al., *Clin. Cancer Res.*, 11:84588466, 2005).

It has been reported that oral administration of FTY720 to mice potently blocked VEGF-induced vascular permeability, an important process associated with angiogenesis, inflammation, and pathological conditions such as sepsis, hypoxia, and solid tumor growth (T Sanchez et al., *J. Biol. Chem.*, 278(47), 47281-47290, 2003).

Cyclosporin A and FK506 (calcineurin inhibitors) are drugs used to prevent rejection of transplanted organs. Although they are effective in delaying or suppressing transplant rejection, classical immunosuppressants such as cyclosporin A and FK506 are known to cause several undesirable side effects including nephrotoxicity, neurotoxicity, β-cell toxicity and gastrointestinal discomfort. There is an unmet need in organ transplantation for an immunosuppressant without these side effects which is effective as a monotherapy or in combination with a classical immunosuppressant for inhibiting migration of, e.g., alloantigen-reactive T-cells to the grafted tissue, thereby prolonging graft survival.

FTY720 has been shown to have therapeutic efficacy in transplant rejection both as a monotherapy and in synergistic combination with a classical immunosuppressant, including cyclosporin A, FK506 and RAD (an mTOR inhibitor). It has been shown that, unlike the classical immunosuppressants cyclosporin A, FK506 and RAD, FTY720 has efficacy for prolonging graft survival without inducing general immunosuppression, and this difference in drug action is believed to be relevant to the synergism observed for the combination (Brinkmann et al., *Transplant Proc.*, 33:530-531, 2001; Brinkmann et al., *Transplantation*, 72:764-769, 2001).

Agonism of the S1P1 receptor has been reported to have therapeutic efficacy for prolonging allograft survival in mouse and rat skin allograft models (Lima et al., *Transplant Proc.*, 36:1015-1017, 2004; Yan et al., *Bioorg. & Med. Chem. Lett.*, 16:3679-3683, 2006). FTY720 has been reported to have therapeutic efficacy for prolonging allograft survival in a rat cardiac allograft model (Suzuki et al., *Transpl. Immunol.*, 4:252-255, 1996). FTY720 has been reported to act synergistically with cyclosporin A to prolong rat skin allograft survival (Yanagawa et al., *J. Immunol.*, 160:5493-5499, 1998), to act synergistically with cyclosporin A and with FK506 to prolong rat cardiac allograft survival, and to act synergistically with cyclosporin A to prolong canine renal allograft survival and monkey renal allograft survival (Chiba et al., *Cell Mol. Biol.*, 3:11-19, 2006). KRP-203, an SIP receptor agonist has been reported to have therapeutic efficacy for prolonging allograft survival in a rat skin allograft model and both as monotherapy and in synergistic combination with cyclosporin A in a rat cardiac allograft model (Shimizu et al., *Circulation*, 111:222-229, 2005). KRP-203 also has been reported to have therapeutic efficacy in combination with mycophenolate mofetil (MMF; a prodrug for which the active metabolite is mycophenolic acid, an inhibitor of purine biosynthesis) for prolonging allograft survival both in a rat renal allograft model and in a rat cardiac allograft model (Suzuki et al., *J. Heart Lung Transplant*, 25:302-209, 2006; Fujishiro et al., *J. Heart Lung Transplant*, 25:825-833, 2006). It has been reported that an agonist of the S1P1 receptor, AUY954, in combination with a subtherapeutic dose of RAD001 (Certican/Everolimus, an mTOR inhibitor) can prolong rat cardiac allograft survival (Pan et al., *Chemistry & Biology*, 13:1227-1234, 2006). In a rat small bowel allograft model, FTY720 has been reported to act synergistically with cyclosporin A to prolong small bowel allograft survival (Sakagawa et al., *Transpl. Immunol.*, 13:161-168, 2004). FTY720 has been reported to have therapeutic efficacy in a mouse islet graft model (Fu et al., *Transplantation*, 73:1425-1430, 2002; Liu et al., *Microsurgery*, 27:300-304; 2007) and in a study using human islet cells to evidence no detrimental effects on human islet function (Truong et al., *American Journal of Transplantation*, 7:2031-2038, 2007).

FTY720 has been reported to reduce the nociceptive behavior in the spared nerve injury model for neuropathic pain which does not depend on prostaglandin synthesis (O. Costu et al., *Journal of Cellular and Molecular Medicine* 12(3), 995-1004, 2008).

FTY720 has been reported to impair initiation of murine contact hypersensitivity (CHS). Adoptive transfer of immunized lymph node cells from mice treated with FTY720 during the sensitization phase was virtually incapable of inducing CHS response in recipients (D. Nakashima et al., *J. Investigative Dermatology* (128(12), 2833-2841, 2008).

It has been reported that prophylactic oral administration of FTY720 (1 mg/kg, three times a week), completely prevented the development of experimental autoimmune myasthenia gravis (EAMG) in C57BL/6 mice (T. Kohono et al., *Biological & Pharmaceutical Bulletin*, 28(4), 736-739, 2005).

In one embodiment, the present invention encompasses compounds which are agonists of the S1P1 receptor having selectivity over the S1P3 receptor. The S1P3 receptor, and not the S1P1 receptor, has been directly implicated in bradycardia (Sanna et al., *J. Biol. Chem.*, 279:13839-13848, 2004). An S1P1 receptor agonist selective over at least the S1P3 receptor has advantages over current therapies by virtue of an enhanced therapeutic window, allowing better tolerability with higher dosing and thus improving efficacy as therapy. The present invention encompasses compounds which are agonists of the S1P1 receptor and which exhibit no or substantially no activity for bradycardia.

S1P1 receptor agonists are useful for treating or preventing conditions where suppression of the immune system or agonism of the S1P1 receptor is in order, such as diseases and disorders mediated by lymphocytes, transplant rejection, autoimmune diseases and disorders, inflammatory diseases and disorders, and conditions that have an underlying defect in vascular integrity or that relate to angiogenesis such as may be pathologic.

S1P1 receptor agonists are useful for treating or preventing conditions where suppression of the immune system or agonism of the S1P1 receptor is in order, such as diseases and disorders mediated by lymphocytes, transplant rejection, autoimmune diseases and disorders, inflammatory diseases and disorders (e.g., acute and chronic inflammatory conditions), cancer, and conditions that have an underlying defect in vascular integrity or that are associated with angiogenesis such as may be pathologic (e.g., as may occur in inflammation, tumor development and atherosclerosis). Such conditions where suppression of the immune system or agonism of the S1P1 receptor is in order include diseases and disorders mediated by lymphocytes; conditions that have an underlying defect in vascular integrity; autoimmune diseases and disorders; inflammatory diseases and disorders (e.g., acute and chronic inflammatory conditions); acute or chronic rejection of cells; tissue or solid organ grafts; arthritis, including psoriatic arthritis, and rheumatoid arthritis; diabetes, including type I diabetes; demyelinating disease, including multiple sclerosis; ischemia-reperfusion injury, including renal and cardiac ischemia-reperfusion injury; inflammatory skin disease, including psoriasis, atopic dermatitis, and acne; hyperproliferative skin disease, including acne; inflammatory bowel disease, including Crohn's disease, and ulcerative colitis; systemic lupus erythematosis; asthma; uveitis; myocarditis; allergy; atherosclerosis; brain inflammation, including Alzheimer's disease, and brain inflammatory reaction following traumatic brain injury; central nervous system disease, including spinal cord injury, or cerebral infarction; pathologic angiogenesis, including as may occur in primary and metastatic tumor growth; rheumatoid arthritis; diabetic retinopathy, atherosclerosis; cancer; chronic pulmonary disease; acute lung injury; acute respiratory disease syndrome; sepsis; and the like. In addition, S1P1 receptor agonists are useful for treating microbial infections, and viral infections or diseases.

In some embodiments, the S1P1 receptor-associated disorder is a disease or disorder mediated by lymphocytes.

In some embodiments, the S1P1 receptor-associated disorder is an autoimmune disease or disorder.

In some embodiments, the S1P1 receptor-associated disorder is an inflammatory disease or disorder.

In some embodiments, the S1P1 receptor-associated disorder is a microbial infection or microbial disease.

In some embodiments, the S1P1 receptor-associated disorder is a viral infection or viral disease.

In some embodiments, the S1P1 receptor-associated disorder is cancer.

In some embodiments, the S1P1 receptor-associated disorder is a disorder in an individual, wherein the disorder is selected from the group consisting of: psoriasis, rheumatoid arthritis, Crohn's disease, transplant rejection, multiple sclerosis, systemic lupus erythematosus, ulcerative colitis, type I diabetes, acne, myocardial ischemia-reperfusion injury, hypertensive nephropathy, glomerulosclerosis, gastritis, polymyositis, thyroiditis, vitiligo, hepatitis, and biliary cirrhosis.

In some embodiments, the S1P1 receptor-associated disorder is psoriasis.

In some embodiments, the S1P1 receptor-associated disorder is rheumatoid arthritis.

In some embodiments, the S1P1 receptor-associated disorder is Crohn's disease.

In some embodiments, the S1P1 receptor-associated disorder is transplant rejection.

In some embodiments, the S1P1 receptor-associated disorder is multiple sclerosis.

In some embodiments, the S1P1 receptor-associated disorder is systemic lupus erythematosus.

In some embodiments, the S1P1 receptor-associated disorder is ulcerative colitis.

In some embodiments, the S1P1 receptor-associated disorder is type I diabetes.

In some embodiments, the S1P1 receptor-associated disorder is acne.

In some embodiments, the S1P1 receptor-associated disorder is myocardial ischemia-reperfusion injury.

In some embodiments, the S1P1 receptor-associated disorder is hypertensive nephropathy.

In some embodiments, the S1P1 receptor-associated disorder is glomerulosclerosis.

In some embodiments, the S1P1 receptor-associated disorder is gastritis.

In some embodiments, the S1P1 receptor-associated disorder is polymyositis.

In some embodiments, the S1P1 receptor-associated disorder is thyroiditis.

In some embodiments, the S1P1 receptor-associated disorder is vitiligo.

In some embodiments, the S1P1 receptor-associated disorder is hepatitis.

In some embodiments, the S1P1 receptor-associated disorder is biliary cirrhosis.

Pharmaceutical Compositions

One aspect of the present invention pertains to compounds represented by any of the formulae described herein used in the preparation of pharmaceutical compositions.

A further aspect of the present invention pertains to pharmaceutical compositions comprising Compound of Formula (Ia) or a pharmaceutically acceptable salt thereof and one or more pharmaceutically acceptable carriers. Some embodiments pertain to pharmaceutical compositions comprising Compound of Formula (Ia) or a pharmaceutically acceptable salt and a pharmaceutically acceptable carrier.

Some embodiments of the present invention include a method of producing a pharmaceutical composition comprising admixing Compound of Formula (Ia) or a pharmaceutically acceptable salt thereof and a pharmaceutically acceptable carrier.

Formulations may be prepared by any suitable method, typically by uniformly mixing Compound of Formula (Ia) or a pharmaceutically acceptable salt thereof with liquids or finely divided solid carriers, or both, in the required proportions and then, if necessary, forming the resulting mixture into a desired shape.

Conventional excipients, such as binding agents, fillers, acceptable wetting agents, tabletting lubricants and disintegrants may be used in tablets and capsules for oral administration. Liquid preparations for oral administration may be in the form of solutions, emulsions, aqueous or oily suspensions and syrups. Alternatively, the oral preparations may be in the form of a dry powder that can be reconstituted with water or another suitable liquid vehicle before use. Additional additives such as suspending or emulsifying agents, non-aqueous vehicles (including edible oils), preservatives and flavorings and colorants may be added to the liquid preparations. Parenteral dosage forms may be prepared by dissolving Compound of Formula (Ia) or a pharmaceutically acceptable salt thereof in a suitable liquid vehicle and filter sterilizing the solution before filling and sealing an appropriate vial or ampule. These are just a few examples of the many appropriate methods well known in the art for preparing dosage forms.

Compound of Formula (Ia) or a pharmaceutically acceptable salt thereof can be formulated into pharmaceutical compositions using techniques well known to those in the art. Suitable pharmaceutically-acceptable carriers, outside those mentioned herein, are known in the art; for example, see Remington, *The Science and Practice of Pharmacy*, 20$^{th}$ Edition, 2000, Lippincott Williams & Wilkins, (Editors: Gennaro et al.)

While it is possible that, for use in treatment, Compound of Formula (Ia) or a pharmaceutically acceptable salt thereof may, in an alternative use, be administered as a raw or pure chemical, it is preferable however to present the active ingredient as a pharmaceutical formulation or composition further comprising a pharmaceutically acceptable carrier.

The invention thus further relates to pharmaceutical formulations comprising Compound of Formula (Ia) or a pharmaceutically acceptable salt thereof, together with one or more pharmaceutically acceptable carriers thereof and/or prophylactic ingredients. The carrier(s) must be "acceptable" in the sense of being compatible with the other ingredients of the formulation and not overly deleterious to the recipient thereof. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: *Polymorphism in Pharmaceutical Solids*, ed. Harry G. Brittain, Vol. 95, Marcel Dekker, Inc., New York, 1999.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

Compound of Formula (Ia) or a pharmaceutically acceptable salt thereof, together with a conventional adjuvant, carrier, or diluent, may thus be placed into the form of pharmaceutical formulations and unit dosages thereof and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active ingredients and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or suspensions, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Compound of Formula (Ia) and pharmaceutically acceptable salts thereof can be used as active ingredients in pharmaceutical compositions, specifically as S1P1 receptor modulators. The term "active ingredient" in the context of a "pharmaceutical composition" is intended to mean a component of a pharmaceutical composition that provides the primary pharmacological effect, as opposed to an "inactive ingredient" which would generally be recognized as providing no pharmaceutical benefit.

The dose when using Compound of Formula (Ia) or a pharmaceutically acceptable salt thereof can vary within wide limits and as is customary and as is known to the physician, it is to be tailored to the individual conditions in each individual case. It depends, for example, on the nature and severity of the illness to be treated; on the condition of the patient; on the formulation employed; on whether an acute or chronic disease state is treated, or prophylaxis is conducted; or on whether further active ingredients are administered in addition to Compound of Formula (Ia) or a pharmaceutically acceptable salt thereof. Representative doses of the present invention include, but are not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg and about 0.001 mg to about 25 mg. Multiple doses may be administered during the day, especially when relatively large amounts are deemed to be needed, for example two, three or four doses. Depending on the individual and as deemed appropriate from the patient's physician or caregiver it may be necessary to deviate upward or downward from the doses described herein.

The amount of active ingredient required for use in treatment will vary not only with the particular ingredient selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular active ingredient employed, whether a drug delivery system is utilized, on whether an acute or chronic disease state is being treated or prophylaxis is conducted or on whether further active ingredients are administered in addition to Compound of Formula (Ia) or a pharmaceutically acceptable salt thereof as part of a drug combination. The dosage regimen for treating a disease condition with Compound of Formula (Ia) or a pharmaceutically acceptable salt thereof is selected in accordance with a variety factors as cited above. Thus, the actual dosage regimen employed may vary widely and therefore may deviate from a preferred dosage regimen and one skilled in the art will recognize that dosages and dosage regimens outside these typical ranges can be tested and, where appropriate, may be used in the methods described herein.

The desired dose may conveniently be presented in a single dose or as divided doses administered at appropriate intervals, for example, as two, three, four or more sub-doses per day. The sub-dose itself may be further divided, for example, into a number of discrete loosely spaced administrations. The daily dose can be divided, especially when relatively large amounts are administered as deemed appropriate, into several, for example, two, three or four part administrations. If appropriate, depending on individual behavior, it may be necessary to deviate upward or downward from the daily dose indicated.

Compound of Formula (Ia) or a pharmaceutically acceptable salt thereof can be administrated in a wide variety of oral and parenteral dosage forms. It will be obvious to those skilled in the art that the following dosage forms may comprise, as the active component, either Compound of Formula (Ia) or a pharmaceutically acceptable salt thereof.

For preparing pharmaceutical compositions from Compound of Formula (Ia) or a pharmaceutically acceptable salt thereof, the pharmaceutically acceptable carrier can be either solid, liquid or a mixture of both. Solid form preparations include powders, tablets, pills, capsules, cachets, suppositories and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component. In tablets, the active component is mixed with the carrier having the necessary binding capacity in suitable proportions and compacted to the desired shape and size. The powders and tablets may contain varying percentages of the active ingredient. A representative amount in a powder or tablet may contain from 0.5 to about 90 percent of the active ingredient; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active ingredient with encapsulating material as a carrier providing a capsule in which the active component, with or without carriers, is surrounded by a carrier, and which is thus in association with it. Similarly, cachets and lozenges are included. Tablets, powders, capsules, pills, cachets and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool and thereby to solidify.

Formulations suitable for vaginal administration may be presented as pessaries, tampons, creams, gels, pastes, foams or sprays containing, in addition to the active ingredient, such carriers as are known in the art to be appropriate.

Liquid form preparations include solutions, suspensions and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compound of Formula (Ia) or a pharmaceutically acceptable salt thereof may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations which are intended to be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents and the like.

For topical administration to the epidermis Compound of Formula (Ia) or a pharmaceutically acceptable salt thereof may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If Compound of Formula (Ia) or a pharmaceutically acceptable salt thereof or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of Compound of Formula (Ia) or a pharmaceutically acceptable salt thereof as an aerosol can be prepared by processes well known to the person skilled in the art. For their preparation, for example, solutions or dispersions of Compound of Formula (Ia) or a pharmaceutically acceptable salt thereof in water, water/alcohol mixtures or suitable saline solutions can be employed using customary additives, for example benzyl alcohol or other suitable preservatives, absorption enhancers for increasing the bioavailability, solubilizers, dispersants and others and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the pharmaceutical composition will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the salt in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

Pharmaceutically acceptable salts including pharmaceutically acceptable acid addition salts may be prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like, such as those pharmaceutically acceptable salts listed in Berge, et al., *Journal of Pharmaceutical Sciences*, 66:1-19 (1977).

The acid addition salts may be obtained as the direct products of compound synthesis. In the alternative, the free base may be dissolved in a suitable solvent containing the appropriate acid and the salt isolated by evaporating the solvent or otherwise separating the salt and solvent. Compound of Formula (Ia) or a pharmaceutically acceptable salt thereof may form solvates with standard low molecular weight solvents using methods known to the skilled artisan.

Compound of Formula (Ia) or a pharmaceutically acceptable salt thereof can be converted to "pro-drugs." The term "pro-drugs" refers to compounds that have been modified with specific chemical groups known in the art and when administered into an individual these groups undergo biotransformation to give the parent compound. Pro-drugs can thus be viewed as compounds containing one or more specialized non-toxic protective groups used in a transient manner to alter or to eliminate a property of the compound. In one general aspect, the "pro-drug" approach is utilized to facilitate oral absorption. A thorough discussion is provided in T. Higuchi and V. Stella, Pro-drugs as Novel Delivery Systems Vol. 14 of the A.C.S. Symposium Series; and in *Bioreversible Carriers in Drug Design*, ed. Edward B. Roche, American Pharmaceutical Association and Pergamon Press, 1987.

Some embodiments of the present invention include a method of producing a pharmaceutical composition for "combination-therapy" comprising admixing Compound of Formula (Ia) or a pharmaceutically acceptable salt thereof, together with at least one known pharmaceutical agent as described herein and a pharmaceutically acceptable carrier.

It is noted that when S1P1 modulators are utilized as active ingredients in pharmaceutical compositions, these are not intended for use only in humans, but in other non-human mammals as well. Indeed, recent advances in the area of animal health-care mandate that consideration be given for the use of active agents, such as S1P1 modulators, for the treatment of an S1P1-associated disease or disorder in companionship animals (e.g., cats, dogs, etc.) and in livestock animals (e.g., cows, chickens, fish, etc.) Those of ordinary skill in the art are readily credited with understanding the utility of such salts in such settings.

Hydrates and Solvates

It is understood that when the phrase "pharmaceutically acceptable salts, solvates and hydrates" is used in reference to a particular compound herein, it is intended to embrace solvates and/or hydrates of the particular compound, pharmaceutically acceptable salts of the particular compound as well as solvates and/or hydrates of pharmaceutically acceptable salts of the particular compound. It is also understood by a person of ordinary skill in the art that hydrates are a subgenus of solvates.

Compound of Formula (Ia) and pharmaceutically acceptable salts, solvates and hydrates thereof can be administrated in a wide variety of oral and parenteral dosage forms. It will be apparent to those skilled in the art that the dosage forms may comprise, as the active component, either Compound of Formula (Ia) and pharmaceutically acceptable salts, solvates and hydrates thereof. Moreover, various hydrates and solvates of Compound of Formula (Ia) and pharmaceutically acceptable salts thereof will find use as intermediates in the manufacture of pharmaceutical compositions. Typical procedures for making and identifying suitable hydrates and solvates, outside those mentioned herein, are well known to those in the art; see for example, pages 202-209 of K. J.

Guillory, "Generation of Polymorphs, Hydrates, Solvates, and Amorphous Solids," in: *Polymorphism in Pharmaceutical Solids*, ed. Harry G. Brittan, Vol. 95, Marcel Dekker, Inc., New York, 1999. Accordingly, one aspect of the present invention relates to processes for preparing hydrates and solvates of Compound of Formula (Ia) and/or pharmaceutically acceptable salts thereof, as described herein, that can be isolated and characterized by methods known in the art, such as, thermogravimetric analysis (TGA), TGA-mass spectroscopy, TGA-Infrared spectroscopy, powder X-ray diffraction (PXRD), Karl Fisher titration, high resolution X-ray diffraction, and the like. There are several commercial entities that provide quick and efficient services for identifying solvates and hydrates on a routine basis. Example companies offering these services include Wilmington PharmaTech (Wilmington, Del.), Avantium Technologies (Amsterdam) and Aptuit (Greenwich, Conn.).

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Illustrated syntheses of the present invention are shown in the following examples. The following examples are provided to further define the invention without, however, limiting the invention to the particulars of these examples. The compounds and salts thereof described herein, supra and infra, are named according to the CS ChemDraw Ultra Version 7.0.1, AutoNom version 2.2, or CS ChemDraw Ultra Version 9.0.7. In certain instances common names are used and it is understood that these common names would be recognized by those skilled in the art.

Chemical shifts of proton nuclear magnetic resonance ($^1$H NMR) spectra are given in parts per million (ppm) with the residual solvent signal used as reference. NMR abbreviations are used as follows: s=singlet, d=doublet, t=triplet, q=quartet, m=multiplet, bs=broad singlet, dd=doublet of doublets.

LCMS spec: HPLC-pumps: LC-10AD VP, Shimadzu Inc.; HPLC system controller: SCL-10A VP, Shimadzu Inc; UV-Detector: SPD-10A VP, Shimadzu Inc; Autosampler: CTC HTS, PAL, Leap Scientific; Mass spectrometer: API 150EX with Turbo Ion Spray source, AB/MDS Sciex; Software: Analyst 1.2.

Example 1

Preparation of
1-Cyclopentyl-2-(trifluoromethyl)benzene
(Compound of Formula (IIb))

Method 1

Preparation of
1-Cyclopentyl-2-(trifluoromethyl)benzene
(Compound of Formula (IIb)), 500 g scale reaction To a 10 L jacketed reactor was added dry THF (2.4 L) and magnesium turnings (81.0 g, 3.33 mol, 1.5 eq.) under $N_2$. In a separate flask FeCl$_3$ (36 g, 0.22 mol, 0.1 eq.) was dissolved in THF (150 mL) (caution, exothermic) under $N_2$. This dark brown solution was allowed to cool to ambient temperature and then added over 10 min to the reactor content under $N_2$ at an internal temperature of about 10° C. TMEDA (402 mL) was added to this yellow/green mixture keeping the internal temperature below about 20° C. (slightly exothermic). The resulting rust brown mixture was stirred at ambient temperature for 1 h under $N_2$ then 1 h at 45° C. The reactor contents were allowed to cool below about 20° C. and a mixture of 1-bromo-2-(trifluoromethyl)benzene (500 g, 2.22 mol) and bromocyclopentane (397 g, 2.66 mol, 1.2 eq.) added dropwise under $N_2$ at a rate as to maintain the internal temperature between about 25-30° C. After the addition, the reaction mixture was stirred at about 25° C. under $N_2$ overnight, allowed to cool to an internal temperature of about 0° C. and quenched with 6 N HCl (2 L) at a rate as to maintain the internal temperature below about 15° C. (caution, exothermic). [Note: 1PC's after completing the addition and stirring overnight were similar indicating that the reaction may have been completed much sooner.] After the quench, hexane (3 L) was added and the reactor contents were stirred at ambient temperature for 1 h. The phases were separated and the aqueous layer back extracted with hexane (1 L). The combined organic layers were dried (Na$_2$SO$_4$), slurried with silica (750 g) and filtered washing the solids with hexane (1 L). The filtrate was concentrated under reduced pressure (100 torr at 37° C.) to give an amber oil (317 g, 97.3 Area % by HPLC, 87.7 wt % by HPLC (contained residual hexane by NMR), corrected yield 58%) which was used in the next step without further purification.

Method 2

Preparation of
1-Cyclopentyl-2-(trifluoromethyl)benzene
(Compound of Formula (IIb)), 1.5 kg scale reaction To a 30 L jacketed reactor, dry THF (6 L) and magnesium turnings (243.0 g, 10 mol, 1.5 eq.) were added under $N_2$. In a separate flask, FeCl$_3$ (162 g, 1.0 mol, 0.15 eq.) was dissolved in THF (800 mL) (caution, exothermic) under $N_2$. This dark brown solution was cooled to ambient temperature using an ice bath and then added over 35 min to the 30 L reactor contents under $N_2$ at an internal temperature of 10° C. To this yellow/green mixture, TMEDA (1.2 L) was added keeping the internal temperature below 20° C. (slightly exothermic). The resulting rust brown mixture was stirred at 45° C. for 1 h under $N_2$. The reactor content was allowed to cool below 20° C. and a mixture of 1-bromo-2-(trifluoromethyl)benzene (1500 g, 6.67 mol) and bromocyclopentane (1192 g, 8.00 mol, 1.2 eq.) added dropwise under $N_2$ at such a rate as to maintain the internal temperature between 25-30° C. (caution, exothermic). After the addition (3.33 h) and the exotherm subsided, the reaction mixture was stirred at 25° C. under $N_2$ overnight, allowed to cool to an internal temperature of 0° C. and quenched with 6 NHCL (3 L, 1.5 h) at such a rate as to maintain the internal temperature below 15° C. (caution, very exothermic). After the quench, ethyl acetate (4 L) was added and the reactor content stirred at ambient temperature for 1 h. The phases were separated and the aqueous layer back extracted with ethyl acetate (2.5 L). The combined organic layers were washed with $H_2O$ (1 L), brine (1.5 L) and dried (Na$_2$SO$_4$). The solvent was rotary evaporated at 35° C. and the residue fraction distilled under high vacuum (65-70° C., 0.15 Torr) to give 823 g of product (58%, not wt % corrected) as a clear colorless liquid. $^1$H NMR (Bruker, 400 MHz, DMSO-d$_6$) δ ppm 7.58-7.64 (m, 3H, ArH), 7.34-7.4 (m, 1H, ArH), 3.21-3.29 (m, 1H, —CH), 1.95-2.04 (m, 2H, —CH$_2$), 1.76-1.88 (m, 2H, —CH$_2$), 1.49-1.71 (m, 4H, —CH$_2$).

Method 3

Preparation of 1-Cyclopentyl-2-(trifluoromethyl) benzene (Compound of Formula (IIb)), two step process using 1-bromo-2-(trifluoromethyl)benzene Step A: Preparation of 1-(2-(Trifluoromethyl)phenyl)cyclopentanol A solution of 1-bromo-2-(trifluoromethyl)benzene (0.5 g, 2.222 mmol) in anhydrous THF (10 mL) was cooled to −78° C. (dry ice WA bath) under argon atmosphere. BuLi (2.5 M in hexanes, 1.068 mL, 2.67 mmol) was added in drops with efficient stirring. The reaction mixture was stirred at −78° C. for 40 min. A solution of cyclopentanone (0.243 g, 2.89 mmol) in anhydrous THF (1.5 mL) was added slowly (in drops) at −78° C. The reaction mixture was stirred at −78° C. for 30 min, gradually brought to room temperature, and stirred for 1 h. The reaction mixture was cooled by an ice bath, quenched with water, and acidified to pH 4-5 by addition of concentrated HCl. The solvent was removed under reduced pressure. The residue was dissolved in methylene chloride, washed with water (2 times), dried over $Na_2SO_4$, filtered and concentrated under reduced pressure. The residue was purified by silica gel chromatography to give the title compound as an oil (250 mg). LCMS m/z=213.1 $[M-H_2O+H]^+$.

Step B: Preparation of 1-Cyclopentyl-2-(trifluoromethyl)benzene

To a solution of 1-(2-(trifluoromethyl)phenyl)cyclopentanol (5.1 g, 22.15 mmol) in ethanol (32 mL) was added 10% Pd—C (500 mg; Degussa; wet) and the mixture was hydrogenated overnight with a hydrogen balloon. The reaction mixture was filtered through Celite®. The filtrate was poured into ice-water (100 mL) and extracted with $CH_2Cl_2$ (2×70 mL). The combined $CH_2Cl_2$ layer was washed with water (1×75 mL), dried over $Na_2SO_4$, filtered and the solvent was removed under reduced pressure to give the title compound (4.3 g). $^1$H NMR (400 MHz, $CDCl_3$) δ ppm 1.58-1.67 (m, 4H), 1.81-1.90 (m, 2H), 2.06-2.15 (m, 2H), 3.32-3.43 (m, 1H), 7.22-7.26 (m, 1H), 7.45-7.51 (m, 2H), 7.58 (d, J=8 Hz, 1H).

Example 2

Preparation of 4-(Chloromethyl)-1-cyclopentyl-2-(trifluoromethyl)benzene (Compound of Formula (IIc))

Method 1

Preparation of 4-(Chloromethyl)-1-cyclopentyl-2-(trifluoromethyl)benzene (Compound of Formula (IIc)), use of 1,3,5-trioxane and chlorosulfonic acid To a 5 L jacketed reactor concentrated sulphuric acid (718 mL) was added and cooled to an internal temperature of about −10° C. under $N_2$. 1-Cyclopentyl-2-(trifluoromethyl)benzene (405 g, 89 wt %, 1.68 mol) was added to the reactor content at once. To the resulting dark brown solution chlorosulfonic acid (225 mL, 3.37 mol, 2 eq.) was added under $N_2$ while maintaining the internal temperature below about −10° C. (caution, HCl evolution). Then, 1,3,5-trioxane (606 g, 6.73 mol, 4 eq.) was added at such a rate as to maintain the temperature below about −10° C. (caution, delayed exotherm: temperature rose to 17° C. over 30 min, HCl evolution. Controlling the exotherm minimizes the formation of the dimer (i.e., bis(4-cyclopentyl-3-(trifluoromethyl)-phenyl)methane) . After the addition and stirring at 0° C. for 1 h (IPC showed no more starting material) under $N_2$, the reaction mixture was slowly poured over ice water (5 L) with stirring while maintaining the internal temperature below 25° C. The reactor was rinsed with ice water (1.5 L) and the combined aqueous layers extracted with hexane (3.6 L). The phases were separated and the aqueous layer back extracted with hexane (3.6 L). The combined organic layers were filtered through a pad of Celite® and washed with saturated $NaHCO_3$ (1.44 L) then water (1.44 L). The organics were concentrated (30 torr at 30° C.) and the resulting dark brown oil passed through a plug of silica eluting and washing with hexane. The solvent was rotary evaporated (30 ton at 30° C.) to afford the product (314 g, 81 wt % by NMR, corrected yield 58%) as a yellow oil. A sample of the crude product was further purified by distillation at 72° C. and 0.12 atm (91 ton) to yield the title compound (98 wt % by HPLC) as a clear colorless oil. The distillation residue contained mostly the dimer species and nearly all of the title compound is recovered in the distillate.

Method 2

Preparation of 4-(Chloromethyl)-1-cyclopentyl-2-(trifluoromethyl)benzene (Compound of Formula (IIc)), use of 1,3,5-trioxane and thionyl chloride Sulfuric acid (1.606 L, 3.01 mol) was transferred into the 30 L jacketed reaction vessel, fitted with a temperature probe, a mechanical stirrer, nitrogen inlet and connected to a chiller/heater. The acid was cooled to −4.5° C. and thionyl chloride (547 mL, 7.49 mol) was added at −4.5° C. via an addition funnel. The reaction temperature was maintained between −5 to −3.5° C. during addition. The mixture was cooled to −6.5° C. and 1,3,5-trioxane (506 g, 5.621 mol) added in four batches (126.5 g each batch) maintaining the reaction temperature between −6.5 to −2° C. (addition of trioxane was exothermic). The mixture was cooled to −5° C. and 1-cyclopentyl-2-(trifluoromethyl)benzene (802.8 g, 3.747 mol) was added slowly via an addition funnel (controlled addition), the addition was exothermic and the temperature was maintained exotherm between −5 to −2.5° C. The reaction was held between −2.5 to +3.5° C. for 1.5 and at 5° C. for 30 min. The reaction mixture was gradually warmed up to 15° C. and stirred overnight. Analysis of the reaction sample by TLC (5% EtOAc-hexane)) showed only product. Analysis by LC/MS showed the product and the slight presence of the dimer (i.e., bis(4-cyclopentyl-3-(trifluoromethyl)-phenyl) methane). The reaction mixture was cooled to −2° C. and quenched with controlled addition of water (11 L) and the temperature was maintained below 15° C. during the aqueous quench (caution: very exothermic). The aqueous slurry was extracted with MTBE (two times: 5 L and 4 L respectively). The combined MTBE layer was washed with satd. $NaHCO_3$ (1×4 L) followed by brine (1 L) solution. The MTBE layer was finally washed with water (2 L) and brine (2 L). The MTBE layer was dried (anhydrous $Na_2SO_4$), filtered and the solvent removed under reduced pressure to obtain the product as an oil, 913 g (crude weight). The crude product was purified by vacuum distillation at 90-93° C./0.15 to 0.2 Ton to obtain the purified product as a very faint yellow oil, 788.4 g (80%); $^1$H NMR similar to previous experimental; HPLC purity, 98.37% (by peak area).

Method 3

Preparation of 4-(Chloromethyl)-1-cyclopentyl-2-(trifluoromethyl)benzene (Compound of Formula (IIc))

Step A: Preparation of Methyl 4-Chloro-3-(trifluoromethyl)benzoate

To a solution of 4-chloro-3-(trifluoromethyl)benzoic acid (10.37 g, 46.2 mmol) in methanol (100 mL) was added concentrated sulfuric acid (0.51 mL, 9.24 mmol). The mixture was heated under reflux overnight. The mixture was allowed to cool to room temperature and concentrated under reduced pressure to form a solid. The solid was filtered and washed with water. The solid was then stirred with saturated aqueous sodium bicarbonate solution to remove any residual sulfuric acid, filtered and dried under vacuum to give the title compound as a white solid (10.18 g). $^1$H NMR (400 MHz, CDCl$_3$) δ ppm 3.96 (s, 3H), 7.60 (d, J=8.34 Hz, 1H), 8.14 (dd, J=8.34, 2.02 Hz, 1H), 8.37 (d, J=2.02 Hz, 1H).

Step B: Preparation of Methyl 4-Cyclopentyl-3-(trifluoromethyl)benzoate

To zinc(II) chloride (0.5 M solution in tetrahydrofuran, 88.0 mL, 44.0 mmol) was added cyclopentylmagnesium chloride (2 M solution in ether, 20.5 mL, 41.1 mmol). The resulting suspension was stirred at room temperature for 1 h. To the above suspension was added methyl 4-chloro-3-(trifluoromethyl)benzoate (7.00 g, 29.3 mmol) and bis(tri-tert-butylphosphine)palladium (1.35 g, 2.64 mmol) at room temperature. The mixture was heated under reflux for 2 h. The mixture was allowed to cool to room temperature, quenched with saturated aqueous sodium bicarbonate solution and filtered. The filtrate was extracted with ethyl acetate. The organic layer was dried over anhydrous sodium sulfate, concentrated under reduced pressure and purified by silica gel column chromatography to give the title compound as an oil (7.64 g). LCMS m/z=273.2 [M+H]$^+$; $^1$H NMR (400 MHz, CDCl$_3$) δ ppm 1.57-1.66 (m, 2H), 1.68-1.82 (m, 2H), 1.82-1.94 (m, 2H), 2.04-2.21 (m, 2H), 3.33-3.49 (m, 1H), 3.93 (s, 3H), 7.54 (d, J=8.21 Hz, 1H), 8.13 (dd, J=8.34, 1.77 Hz, 1H), 8.27 (s, 1H).

Step C: Preparation of (4-Cyclopentyl-3-(trifluoromethyl)phenyl)methanol

To a solution of methyl 4-cyclopentyl-3-(trifluoromethyl)benzoate (8.16 g, 30.0 mmol) in 1,4-dioxane (200 mL) was added lithium borohydride solution (2 M in tetrahydrofuran, 30.0 mL, 59.9 mmol). The mixture was heated under reflux for 2.5 h. The mixture was allowed to cool to room temperature and carefully quenched with 1 N aqueous HCl solution to pH 5. The organic layer was separated and the aqueous layer was extracted with ethyl acetate. The combined organic layers were dried over anhydrous sodium sulfate, concentrated under reduced pressure and purified by silica gel column chromatography to give the title compound as a colorless oil (1.21 g). $^1$H NMR (400 MHz, CDCl$_3$) δ ppm 1.56-1.63 (m, 2H), 1.66-1.77 (m, 2H), 1.81-1.91 (m, 2H), 2.03-2.15 (m, 2H), 3.37 (quintet, J=8.00 Hz, 1H), 4.71 (d, J=4.29 Hz, 2H), 7.45-7.47 (m, 1H), 7.49 (d, J=1.14 Hz, 1H), 7.60 (s, 1H).

Step D: Preparation of 4-(Chloromethyl)-1-cyclopentyl-2-(trifluoromethyl)benzene To (4-cyclopentyl-3-(trifluoromethyl)phenyl)methanol (1.21 g, 4.95 mmol) was added thionyl chloride (5.5 mL, 74.2 mmol). The mixture was heated at 50° C. for 2 h before it was allowed to cool to room temperature and stirred at room temperature overnight. The mixture was poured into ice and stirred for 5 min before it was extracted with dichloromethane. The organic extract was washed with saturated aqueous sodium bicarbonate solution, dried over anhydrous sodium sulfate and concentrated under reduced pressure to give the title compound as an oil (1.16 g). $^1$H NMR (400 MHz, CDCl$_3$) δ ppm 1.55-1.63 (m, 2H), 1.69-1.77 (m, 2H), 1.82-1.90 (m, 2H), 2.05-2.13 (m, 2H), 3.37 (quintet, J=8.59 Hz, 1H), 4.58 (s, 2H), 7.46 (d, J=8.00 Hz, 1H), 7.52 (d, J=8.00 Hz, 1H), 7.61 (d, J=1.52 Hz, 1H).

Method 4

Preparation of 4-(Chloromethyl)-1-cyclopentyl-2-(trifluoromethyl)benzene (Compound of Formula (IIc))

Step A: Preparation of Methyl 4-Chloro-3-(trifluoromethyl)benzoate

To a solution of 4-chloro-3-(trifluoromethyl)benzoic acid (200 g, 891 mmol) in MeOH (600 mL, 14.8 mol), sulfuric acid (27 mL, 445 mmol) was added. The mixture was stirred at reflux for 6 h, allowed to cool and the solvent evaporated under reduce pressure. The resulting liquid residue (~250 mL) was poured onto ice water whereby a white suspension formed. The solid was filtered and washed with 0.05 N NaOH (3×200 mL) followed by H$_2$O (3×200 mL). The solid was dried under vacuum for 16 h followed by 4 h at 40° C. to give the title compound as an off-white solid (197.0 g). $^1$H NMR (400 MHz, CDCl$_3$) δ ppm, 3.98 (s, 3H), 7.62 (d, J=8.4 Hz, 1H), 8.16 (dd, J=8.8 Hz, 2.0 Hz, 1H), 8.39 (d, J=2.0 Hz, 1H).

Step B: Preparation of Methyl 4-Cyclopentyl-3-(trifluoromethyl)benzoate

To a solution of 4-chloro-3-(trifluoromethyl)benzoate (196.7 g, 824 mmol) in THF (100 mL), cyclopentylzinc(II) bromide (1979 mL, 989 mmol) was added dropwise at 7.8° C. The temperature at the end of the addition rose to 22° C. Bis(tri-t-butylphosphine)palladium (21.07 g, 41.2 mmol) was added to the dark brown solution at the same temperature, and the resulting mixture was stirred at 70° C. for 8 h. The mixture was added to saturated aqueous NaHCO$_3$ (100 mL) at 0° C., stirred at the same temperature for 30 min and then at 22° C. for 2 h. The resulting suspension was filtered through Celite® and the filtrate concentrated under vacuum. The solids were washed with EtOAc (3×300 mL), the filtrate was combined with the previous concentrate and the combined organics were washed with H$_2$O (2×600 mL), brine (2×500 mL), dried (Na$_2$SO$_4$), decanted and concentrated under reduced pressure to give the title compound as an orange oil (227 g) without further purification. LCMS m/z=273.4 [M+H]$^+$; $^1$H NMR (400 MHz, CDCl$_3$) δ ppm 1.71-1.60 (m, 2H), 1.83-1.75 (m, 2H), 1.95-1.87 (m, 2H), 2.21-2.11 (m, 2H), 3.46 (quintet, J=8.8 Hz, 1H), 3.97 (s, 3H), 7.58 (d, J=8.4 Hz, 1H), 8.18 (dd, J=8.0 Hz, 1.6 Hz, 1H), 8.31 (d, J=1.6 Hz, 1H).

Step C: Preparation of (4-Cyclopentyl-3-(trifluoromethyl)phenyl)methanol

To a solution of 4-cyclopentyl-3-(trifluoromethyl)benzoate (224 g, 823 mmol) in 1,4-dioxane (600 mL), LiBH$_4$ (494 mL, 987 mmol, 2 M solution in THF) was added dropwise at 22° C. The resulting suspension was stirred at 85.5° C. for 5.5 h. The dark brown solution was cooled to 0° C. and the pH adjusted to 5 by slowly adding 6 N HCl (130 mL). The layers were separated and to the aqueous phase H$_2$O (250 mL) and NaCl (20 g) were added. The combined aqueous layers were extracted with EtOAc (2×250 mL). The EtOAc layer was added to the previously separated organic phase and the combined organics were concentrated under reduced pressure. The resulting suspension was filtered through a pad of Celite®/Na$_2$SO$_4$ and the solids were washed with EtOAc (3×400 mL). The combined organics were rotary evaporated and the dark brown oily residue was subjected to chromatography on silica to give the title compound as colorless liquid (110 g). LCMS m/z=243.3 [M−H]$^+$; $^1$H NMR (400 MHz, CDCl$_3$) δ ppm 1.67-1.55 (m, 2H), 1.82-1.69 (m, 2H), 1.95-1.83 (m, 2H), 2.19-2.04 (m, 2H), 3.39 (quintet, J=8.0 Hz, 1H), 4.72 (s, 2H), 7.55-7.46 (m, 2H), 7.62 (s, 1H).

Step D: Preparation of 4-(Chloromethyl)-1-cyclopentyl-2-(trifluoromethyl)benzene To (4-cyclopentyl-3-(trifluoromethyl)phenyl)methanol (110 g, 113 mmol), thionyl chloride (329 mL, 4.50 mol) was added dropwise at such a rate as to maintain the internal temperature between 10-25° C. (cooled with ice-water). The resulting mixture was stirred at 50° C. for 3.5 h followed by 6 h at 25° C. The mixture was concentrated under reduced pressure and the resulting oily residue poured into ice-water (450 mL) under vigorous stirring. The layers were separated and the aqueous phase extracted with CH$_2$Cl$_2$ (3×400 mL). The combined organic layers were washed with saturated NaHCO$_3$ (400 mL), brine (2×400 mL), dried (Na$_2$SO$_4$), filtered over fresh Na$_2$SO$_4$, and concentrated in vacuo to give the title compound as a pale yellow oil (113.3 g). $^1$H NMR (400 MHz, CDCl$_3$) δ ppm 1.67-1.57 (m, 2H), 1.81-1.71 (m, 2H), 1.94-1.84 (m, 2H), 2.16-2.07 (m, 2H), 3.39 (quintet, J=8.6 Hz, 1H), 4.61 (s, 2H), 7.49 (d, J=8.4 Hz, 1H), 7.54 (dd, J=8.4 Hz, 1.6 Hz, 1H), 7.63 (d, J=1.6 Hz, 1H).

Method 5

Preparation of 4-(Chloromethyl)-1-cyclopentyl-2-(trifluoromethyl)benzene (Compound of Formula (IIc))

Step A: Preparation of 4-Bromo-1-cyclopentyl-2-(trifluoromethyl)benzene

To a solution of 1-cyclopentyl-2-(trifluoromethyl)benzene (0.5 g, 2.334 mmol) in acetic acid (2.5 mL) was added bromine (1.202 mL, 23.34 mmol). The mixture was stirred well, concentrated H$_2$SO$_4$ (2.5 mL) was added, and stirred at 40° C. for 1.5 h. The reaction mixture was poured into ice-water and extracted with CH$_2$Cl$_2$. The CH$_2$Cl$_2$ layer was washed with water, followed by a solution of sodium thiosulfate, then with water. The organic layer was dried over Na$_2$SO$_4$ and the solvent was removed under reduced pressure. The residue was purified by silica gel chromatography to give the title compound (250 mg). $^1$H NMR (400 MHz, DMSO-d$_6$) ppm 1.52-1.75 (m, 4H), 1.78-1.88 (m, 2H), 1.95-2.04 (m, 2H), 3.16-3.26 (m, 1H), 7.57 (d, J=8.4 Hz, 1H), 7.76 (d, J=2 Hz, 1H), 7.81 (dd, J=8.4 Hz, 2 Hz, 1H).

Step B: Preparation of 4-Cyclopentyl-3-(trifluoromethyl)benzaldehyde

In a 15 mL round-bottomed flask were placed 4-bromo-1-cyclopentyl-2-(trifluoromethyl)benzene (0.186 g, 0.635 mmol) and anhydrous THF (1.86 mL) under argon atmosphere. The solution was stirred well and cooled to −78° C. (dry ice IPA bath). BuLi (2.5 M in hexanes, 0.281 mL, 0.703 mmol) was added in drops (slowly) and the reaction mixture was stirred at low temperature for 25 min. Anhydrous DMF (0.1 mL, 0.766 mmol) was added in drops at −78° C. (slowly). The mixture was stirred at −78° C. for 20 min then at room temperature for 30 min. The reaction was quenched with water, acidified with 2 M HCl and extracted with EtOAc. The EtOAc layer was washed with water, dried over Na$_2$SO$_4$, and concentrated in vacuo to give the title compound as an oil (60 mg). LCMS m/z=243.3 [M+H]$^+$. $^1$H NMR (400 MHz, DMSO-d$_6$) δ ppm 1.55-1.7 (m, 4H), 1.79-1.94 (m, 2H), 1.95-2.09 (m, 2H), 3.29-3.37 (m, 1H), 7.86 (d, J=8 Hz, 1H), 8.12 (d, J=8 Hz, 1H), 8.16 (d, J=1.2 Hz, 1H), 10.46 (s, 1H).

Step C: Preparation of (4-Cyclopentyl-3-(trifluoromethyl)phenyl)methanol

To a solution of 4-cyclopentyl-3-(trifluoromethyl)benzaldehyde (0.25 g, 1.032 mmol) in ethanol (2.5 mL) was added sodium borohydride (0.047 g, 1.238 mmol) and the mixture was stirred at room temperature for 2 h. The mixture was quenched with water, acidified with 6 N HCl, diluted with more water and extracted with CH$_2$Cl$_2$. The CH$_2$Cl$_2$ layer was washed with water, dried over Na$_2$SO$_4$, filtered and concentrated in vacuo to give the title compound (0.22 g). LCMS m/z=227.5 [M−H$_2$O+H]$^+$. $^1$H NMR (400 MHz, DMSO-d$_6$) δ ppm 1.54-1.72 (m, 4H), 1.77-1.89 (m, 2H), 1.93-2.05 (m, 2H), 3.19-3.28 (m, 1H), 4.52 (d, J=6 Hz, 2H), 5.28 (t, J=5.6 Hz, 1H), 7.52-7.6 (m, 3H).

Step D: Preparation of 4-(Chloromethyl)-1-cyclopentyl-2-(trifluoromethyl)benzene To (4-cyclopentyl-3-(trifluoromethyl)phenyl)methanol (110 g, 113 mmol) thionyl chloride (329 mL, 4.50 mol, 10 eq) was added dropwise at such a rate as to maintain the internal temperature between 10-25° C. (cooled with ice-water). The resulting mixture was stirred at 50° C. for 3.5 h followed by 6 h at 25° C. The mixture was concentrated under reduced pressure and the resulting oily residue poured into ice-water (450 mL) under vigorous stirring. The layers were separated and the aqueous phase extracted with CH$_2$Cl$_2$ (3×400 mL). The combined organic layers were washed with saturated NaHCO$_3$ (400 mL), brine (2×400 mL), dried (Na$_2$SO$_4$), filtered over fresh Na$_2$SO$_4$, and concentrated in vacuo to afford 4-(chloromethyl)-1-cyclopentyl-2-(trifluoromethyl)benzene as a pale yellow oil (113.3 g, 96%). $^1$H NMR (400 MHz, CDCl$_3$) δ ppm 1.67-1.57 (m, 2H), 1.81-1.71 (m, 2H), 1.94-1.84 (m, 2H), 2.16-2.07 (m, 2H), 3.39 (quintet, J=8.6 Hz, 1H), 4.61 (s, 2H), 7.49 (d, J=8.4 Hz, 1H), 7.54 (dd, J=8.4 Hz, 1.6 Hz, 1H), 7.63 (d, J=1.6 Hz, 1H).

Example 3

Preparation of Ethyl 2-(2-morpholinocyclopent-2-enylidene)acetate (Compound of Formula (IIg), Wherein R$^3$ is Ethyl)

Cyclopentanone (4.00 kg), morpholine (4.16 kg) and cyclohexane (7.96 kg) were charged to a 50-L glass-lined reactor equipped with overhead agitation, jacket temperature control, a nitrogen inlet, and a Dean-Stark trap. The reactor contents were heated to about 85° C. to 95° C. for approximately 26 h so as to collect approximately 1.29 kg of water in the Dean-Stark trap. The reaction to form the enamine (i.e., 4-cyclopentenylmorpholine, Compound of Formula (IIe) wherein $R^1$ and $R^2$ together with the nitrogen atom form a morpholine ring) is deemed complete when the morpholine amount by GC is verified to be less than 3% by GC peak area.

The reactor contents were cooled to about 60° C. and ethyl glyoxalate (Compound of Formula (IIf) wherein $R^3$ is ethyl; 10.70 kg, 50% solution in toluene) was added to the mixture slowly so as to maintain an internal temperature of ≤80° C. The reactor contents were heated to about 85° C. to 95° C. for approximately 26 hours so as to collect approximately 0.94 kg of water in the Dean-Stark trap. The reaction to form the enamine ester was deemed complete when the eneamine (i.e., 4-cyclopentenylmorpholine) amount by GC was verified to be less than 0.5% by GC peak area. The cyclohexane/toluene mixture was vacuum distilled at 41° C. and 4 mm of Hg to remove most of the cyclohexane (9.36 kg). Then, ethanol (47.59 kg) was charged to the reactor, and the resulting solution was vacuum distilled at 28.1° C. and 4 mm Hg to remove solvent (48.15 kg). Ethanol (6.32 kg) and water (8.00 kg) were charged to the reactor and the reactor contents stirred at 25° C. The mixture was stirred further for 16 h at about 0-5° C.

The product slurry was collected by filtration, washed with two portions of aqueous ethanol (6.31 kg ethanol dissolved in 32.27 kg water). The filter-cake was further washed with water (19.99 kg), dried at 45° C. to 50° C. under vacuum for 71 h. The product, ethyl 2-(2-morpholinocyclopent-2-enylidene)acetate (4.84 kg, Compound of Formula (IIg), wherein $R^3$ is ethyl) was obtained in 42.8% yield and 99.6 Area % by HPLC.

$^1$H NMR (400 MHz, DMSO-$d_6$) δ 1.21 (t, J=7.2 Hz, 3H), 2.39-2.45 (m, 2H), 2.73-2.79 (m, 4H), 2.91-2.96 (m, 2H), 3.64-3.70 (m, 4H), 4.09 (q, J=7.2 Hz, 2H), 5.65-5.68 (m, 1H), 5.89-5.92 (m, 1H). LCMS m/z calcd for $C_{13}H_{19}NO_3$: 237.29. Found 238.2 (M+H)$^+$.

Example 4

Preparation of E/Z Ethyl 2-(7-(Benzyloxy)-1,2-dihydrocyclopenta[b]indol-3(4H)-ylidene)acetate (Compound of Formula (IIi), Wherein $R^3$ is Ethyl, and $R^4$, $R^5$, and $R^6$ are each H)

Method 1

To a nitrogen-purged 5-L reactor was charged (4-(benzyloxy)phenyl)hydrazine hydrochloride (538 g, 2.15 mol), ethyl 2-(2-morpholinocyclopent-2-enylidene)acetate (560 g, 2.36 mol, 1.1 eq; Compound of Formula (IIg), wherein $R^3$ is ethyl), ethanol (1.4 L) and acetic acid (0.75 L). The internal temperature was raised to 60° C. and the reaction was monitored by HPLC for the disappearance of starting materials. TFA (1.2 eq, 294 g, 2.58 mol) was charged drop wise while maintaining an internal temperature of 62.5° C.±2.5° C. The reaction was monitored for completion by HPLC and was considered complete when the imine intermediate was less than 4 Area %. The internal temperature was decreased to room temperature (22° C.) and held for >12 hours to allow crystallization and isomerization of the Z-isomer to the E-isomer. The reaction mixture was cooled to 4° C.±2° C. and filtered. The filter cake was rinsed with chilled ethanol (3×500 ml at 5° C.±3° C.). The filter cake was rinsed with water (1×1.5 L, 1×500 mL, at 20±3° C.). The solids were dried under reduced pressure (45±5° C., 19 in Hg.) to afford 297.8 g (40%) as a yellow powder.

$^1$H NMR (400 MHz, DMSO-$d_6$) δ 1.27 (t, J=7.0 Hz, 3H), 2.93 (m, 2H), 3.49 (m, 2H), 4.15 (q, J=7.0 Hz, 2H), 5.13 (s, 2H), 6.02 (m, 1H), 6.98 (dd, J=2.4, 6.4 Hz, 1H), 7.16 (m, 1H), 7.54-7.30 (m, 5H), 11.27 (s, 1H). LCMS m/z calcd for $C_{22}H_{20}NO_3$: 347.41. Found: 348.4 (M+H)$^+$.

Method 2

Preparation of E/Z Ethyl 2-(7-(Benzyloxy)-1,2-dihydrocyclopenta[b]indol-3(4H)-ylidene)acetate (Compound of Formula (IIi), Wherein $R^3$ is Ethyl, and $R^4$, $R^5$, and $R^6$ are each H)

To a nitrogen-purged 250-mL round bottom flask equipped with an overhead mechanical stirring and condenser was charged (4-(benzyloxy)phenyl)hydrazine hydrochloride (40 g, 160 mmol) and zinc chloride anhydrous beads-10 mesh (25.01 g, 183 mmol). The reactor was alternatively evacuated then backfilled with nitrogen (3 times). A solution of ethyl 2-(2-morpholinocyclopent-2-enylidene)acetate (41.6 g, 175 mmol, 1.1 eq; Compound of Formula (IIg), wherein $R^3$ is ethyl), ethanol (80 mL) and acetic acid (80 mL) was charged. The internal temperature rose to an internal temperature of about 47° C. The resulting mixture was warmed to about 60° C. and monitored by HPLC. The internal temperature was decreased to about 5° C., the suspension filtered and the filtered cake rinsed with ethanol (3×100 mL). The solids are dried under reduced pressure (about 40° C., 19 in Hg.). NMR indicated the presence of morpholine. The resulting solids were triturated with water (300 mL) and filtered. The solids were dried under reduced pressure (45±5° C., 19 mm of Hg.) to afford the title compound (14.4 g, 26%).

Method 3

Preparation of E/Z Ethyl 2-(7-(Benzyloxy)-1,2-dihydrocyclopenta[b]indol-3(4H)-ylidene)acetate (Compound of Formula (IIi), Wherein $R^3$ is Ethyl, and $R^4$, $R^5$, and $R^6$ are each H)

Additional procedures to prepare E/Z ethyl 2-(7-(Benzyloxy)-1,2-dihydrocyclopenta[b]indol-3(4H)-ylidene)acetate have been conducted using similar procedures as cited above in Methods 1 and 2 (Example 4) with the exception that the Brønsted acid or Lewis acid in Methods 1 and 2 respectively was replaced with a Brønsted acid or Lewis acid selected from the following list: p-TsOH, $H_2SO_4$, methane sulfonic acid, formic acid, $ZnCl_2$, $FeCl_3$, HCl, CuCl, CuI, $BF_3OEt_2$, $Zn(Tf)_2$, $Yb(Tf)_2$, $Sc(Tf)_2$, and $AlCl_3$. Reactions using these alternative acids (i.e., Brønsted acid or Lewis acid) were shown to prepare E/Z ethyl 2-(7-(Benzyloxy)-1,2-dihydrocyclopenta[b]indol-3(4H)-ylidene)acetate.

Example 5

Preparation of Ethyl 2-(7-Hydroxy-1,2,3,4-tetrahydrocyclopenta[b]indol-3-yl)acetate (Compound of Formula (IIj), Wherein $R^3$ is Ethyl)

Method 1

Preparation of Ethyl 2-(7-Hydroxy-1,2,3,4-tetrahydrocyclopenta[b]indol-3-yl)acetate The E/Z mixture of ethyl 2-(7-(benzyloxy)-1,2-dihydrocyclopenta[b]indol-3(4H)-ylidene)acetate (7.5 g, 21.59 mmol) and 10% Pd/C (50% wet; 1.13 g, 10.58 mmol) were taken up in ethyl acetate (60 mL, 613 mmol). The suspension was degassed 3× with $N_2$ and followed with pre-activation of the catalyst with the addition of formic acid (2.48 mL, 64.8 mmol). The mixture was allowed to stir for 1-2 min. Triethylamine (9.03 mL, 64.8 mmol) was charged portion-wise maintaining the temperature<35° C. Upon complete addition of triethylamine, the mixture was stirred for about 5-10 minutes followed with heating to 50° C. The reaction progression was followed by HPLC to monitor the complete consumption of starting material (i.e., E/Z mixture of ethyl 2-(7-(benzyloxy)-1,2-dihydrocyclopenta[b]indol-3(4H)-ylidene)acetate) and the debenzylated intermediate. Approximately after 4 h at 50° C., the solution was cooled to about 20° C., the Pd/C was removed via vacuum filtration and rinsed with ethyl acetate (30 mL). To the filtrate was added water (75 mL) and the biphasic mixture was partitioned. The organics were washed with water (2×60 mL), concentrated under vacuum with a bath temp of 40° C. to a minimum stir volume, chased with ethyl acetate (1×37.5 mL) and further concentrated under vacuum to a minimum stir volume. Ethyl acetate (11 mL) was charged to the crude mixture and the resulting solution was heated to 60° C. Heptanes (34 mL) were charged maintaining the internal temperature at 60° C. The solution was slowly cooled to 10° C. and held for 30 min. The slurry was filtered, the filter cake rinsed with heptanes (2×52.5 mL) and the solids dried in the vacuum oven set to 40° C. to afford the title compound (2.78 g, 74.5% yield) as light beige solids.

$^1$H NMR (400 MHz, DMSO-$d_6$): δ 1.20 (t, J=7.1 Hz, 3H), 2.02-2.11 (m, 1H), 2.41 (q, J=8.9 Hz, 1H), 2.54-2.63 (m, 1H), 2.63-2.72 (m, 2H), 2.78 (dd, J=5.5, 15.7 Hz, 1H), 3.41-3.50 (m, 1H), 4.11 (q, J=7.1 Hz, 2H), 6.49 (dd, J=2.4, 8.7 Hz, 1H), 6.62 (d, J=2.3 Hz, 1H), 7.07 (d, J=8.6 Hz, 1H), 8.47 (s, 1H), 10.25 (s, 1H). LCMS m/z calcd for $C_{15}H_{17}NO_3$: 259.30. Found: 260.2 (M+H)$^+$.

Method 2

Preparation of Ethyl 2-(7-Hydroxy-1,2,3,4-tetrahydrocyclopenta[b]indol-3-yl)acetate (Compound of Formula, (IIj), Wherein $R^3$ is ethyl)

To a 3-neck 250 mL round bottom flask was charged E/Z mixture of ethyl 2-(7-(benzyloxy)-1,2-dihydrocyclopenta[b]indol-3(4H)-ylidene)acetate (15 g, 43.2 mmol) and purged with $N_2$. 10% Pd/C (50% wet; 2.34 g, 22.02 mmol) was charged and the contents degassed 3× with $N_2$ followed by addition of ethyl acetate (120 mL, 1226 mmol). The solution was degassed 3× with $N_2$ and followed by the pre-activation of the catalyst with the addition of formic acid (4.97 mL, 130 mmol). The mixture was allowed to stir for 1-2 minutes. Triethylamine (18.05 mL, 130 mmol) was charged drop-wise maintaining an internal temperature between about 24° C. to 30° C. The reaction was held at 30° C. for 1 h to allow for reaction completion. The reaction progression was monitored by HPLC. Upon reaction completion, the solution was cooled to 20° C. and the catalyst Pd/C was removed via vacuum filtration and rinsed with 30 mL of ethyl acetate. Water (90 mL) was charged to the filtrate and the biphasic mixture was partitioned. The organics were washed with water (2×90 mL), concentrated under vacuum in bath temp 40° C. to a minimum stir volume, chased with ethyl acetate (1×30 mL) and further concentrated under vacuum to a minimum stir volume. Ethyl acetate (22.5 mL) was charged to the crude and the resulting solution was heated to 60° C. Heptanes (67.5 mL) were charged maintaining the internal temperature at 60° C. whereupon crystallization was initiated. The slurry was cooled to 40° C. and aged for 1 h, further cooled to 5-10° C. and aged for 0.5 h. The slurry was filtered, the filter cake rinsed with heptanes (2×60 mL) and the solids dried in the vacuum oven set to 40° C. to afford the title compound (8.86 g, 79% yield) as light beige solids.

$^1$H NMR (400 MHz, DMSO-$d_6$): δ 1.20 (t, J=7.1 Hz, 31-1), 2.02-2.11 (m, 1H), 2.41 (q, J=8.9 Hz, 1H), 2.54-2.63 (m, 1H), 2.63-2.72 (m, 2H), 2.78 (dd, J=5.5, 15.7 Hz, 1H), 3.41-3.50 (m, 1H), 4.11 (q, J=7.1 Hz, 2H), 6.49 (dd, J=2.4, 8.7 Hz, 1H), 6.62 (d, J=2.3 Hz, 1H), 7.07 (d, J=8.6 Hz, 1H), 8.47 (s, 1H), 10.25 (s, 1H). LCMS m/z calcd for $C_{15}H_{17}NO_3$: 259.30. Found: 260.2 (M+H)$^+$.

Method 3

Preparation of Ethyl 2-(7-Hydroxy-1,2,3,4-tetrahydrocyclopenta[b]indol-3-yl)acetate (Compound of Formula (IIj), Wherein $R^3$ is ethyl)

Step A: Preparation of Ethyl 1-(2-Ethoxy-2-oxoethyl)-2-oxocyclopentanecarboxylate To a solution of ethyl 2-oxocyclopentanecarboxylate (93.27 g, 597 mmol) and ethyl 2-bromoacetate (144.64 g, 866 mmol) in acetone (1.2 L) was added $K_2CO_3$ (165 g, 1194 mmol). The mixture was heated at 56° C. for 24 h. The solid was filtered off and the filter cake was washed with acetone (3×100 mL). The filtrate was concentrated and the resultant liquid was purified by a silica gel plug to give the title compound as light yellow liquid (54.7 g). LCMS m/z=243.3 [M+H]$^+$; $^1$H NMR (400 MHz, CDCl$_3$) δ ppm 1.23 (t, J=7.14 Hz, 3H), 1.24 (t, J=7.14 Hz, 3H), 1.95-2.03 (m, 1H), 2.06-2.15 (m, 2H), 2.35-2.50 (m, 2H), 2.55-2.60 (m, 1H), 2.80 (dd, J=15.2, 2.09 Hz, 1H), 2.95 (dd, J=15.2, 2.09 Hz, 1H), 4.09 (q, J=7.14 Hz, 2H), 4.12 (q, J=7.14 Hz, 2H).

Step B: Preparation of 2-(2-Oxocyclopentyl)acetic Acid

A solution of ethyl 1-(2-ethoxy-2-oxoethyl)-2-oxocyclopentanecarboxylate (50.0 g, 206 mmol) in HOAc (500 mL) and 6 M HCl (250 mL) was heated at 100° C. for 6 h. The solvent was removed under reduced pressure and the residue was partitioned between EtOAc (500 mL) and $H_2O$ (200 mL). Aqueous layer was separated and extracted with EtOAc (2×250 mL). The combined organic layers were washed with $H_2O$ (300 mL), brine (300 mL), dried over $Na_2SO_4$, decanted and concentrated to yield the title compound as a white solid (22 g). $^1$H NMR (400 MHz, CDCl$_3$) δ ppm 1.59-1.72 (m, 1H), 1.75-1.90 (m, 1H), 2.03-2.10 (m, 1H), 2.20 (dd, J=10.9, 8.9 Hz, 1H), 2.30-2.40 (m, 2H), 2.40-2.50 (m, 2H), 2.80 (dd, J=15.7, 7.2 Hz, 1H), 11.5 (s, 1H).

Step C: Preparation of Ethyl 2-(2-Oxocyclopentyl)acetate

To a solution of 2-(2-oxocyclopentyl)acetic acid (23.6 g, 166 mmol) in absolute ethanol (400 mL) was added $H_2SO_4$ (16.28 g, 166 mmol). The resultant solution was heated under reflux overnight. The reaction mixture was concentrated and the liquid residue was added into ice-water (200 mL). The aqueous mixture was extracted with DCM (3×200 mL). The combined organic layers were washed with $H_2O$ (300 mL), brine (300 mL), dried over $Na_2SO_4$, decanted, concentrated and dried under vacuum to afford the title compound as a light yellow liquid (27.2 g). LCMS m/z=171.3 [M+H]$^+$; $^1$H NMR (400 MHz, CDCl$_3$) δ ppm 1.19 (t, J=7.14 Hz, 3H), 1.50-1.62 (m, 1H), 1.65-1.80 (m, 1H), 1.92-2.02 (m, 1H), 2.12 (dd, J=16.7, 8.86 Hz, 1H), 2.19-2.29 (m, 2H), 2.30-2.44 (m, 2H), 2.65 (dd, J=15.12, 2.6 Hz, 1H), 4.07 (q, J=7.14 Hz, 2H).

Step D: Preparation of Ethyl 2-(7-Hydroxy-1,2,3,4-tetrahydrocyclopenta[b]indol-3-yl)acetate 2-Iodo-4-methoxyaniline (2.0 g, 8.03 mmol) and ethyl 2-(2-oxocyclopentyl)acetate (2.05 g, 12.1 mmol) were dissolved in DMF (30 mL) and tetraethyl orthosilicate (2.12 g, 10.4 mmol) and pyridinump-toluenesulfonate (PPTS) (0.081 g, 0.321 mmol) were added. The reaction mixture was heated and stirred at 135° C. for 4 h. After cooling to 120° C., DIEA (3.11 g, 24.09 mmol) and palladium (II) acetate (0.054 g, 0.241 mmol) were added. The reaction mixture was stirred for 3 h and then partitioned between ethyl acetate and water. The aqueous layer was extracted twice with ethyl acetate. The combined organic extracts were dried over sodium sulfate, filtered and concentrated under reduced pressure. The resultant solution was diluted with 50% ethyl acetate in hexanes and filtered through a pad of silica gel. The filtrate was concentrated and purified by silica gel column chromatography to give 1.9 g of ethyl 2-(7-methoxy-1,2,3,4-tetrahydrocyclopenta[b]indol-3-yl)acetate containing residual ethyl 2-(2-oxocyclopentyl)acetate. The mixture was dissolved in DCM (80 mL) and cooled to 0° C. Boron tribromide (21.0 mL, 21.0 mmol, 1.0 M in DCM) was added and the reaction was stirred for 1.5 h. Ice water was added and the reaction mixture was allowed to reach room temperature. The aqueous mixture was extracted three times with DCM. The combined organics were dried over sodium sulfate, filtered and concentrated under reduced pressure. The residue was purified by silica gel column chromatography to give the title compound (650 mg). LCMS m/z=260.3 [M+H]$^+$; $^1$H NMR (400 MHz, CDCl$_3$) δ ppm 1.29 (t, J=7.2 Hz, 3H), 2.05-2.14 (m, 1H), 2.50 (dd, J=16.8, 11.2 Hz, 1H), 2.68-2.86 (m, 4H), 3.48-3.58 (m, 1H), 4.16-4.24 (m, 2H), 6.66 (dd, J=8.6, 2.4 Hz, 1H), 6.85 (d, J=2.4 Hz, 1H), 7.15 (d, J=8.7 Hz, 1H), 8.4 (s, 1H).

Method 4

Preparation of Ethyl 2-(7-Hydroxy-1,2,3,4-tetrahydrocyclopenta[b]indol-3-yl)acetate (Compound of Formula (IIj), Wherein R$^3$ is ethyl)

Step A: Preparation of Ethyl 2-(7-Methoxy-1,2,3,4-tetrahydrocyclopenta[b]indol-3-yl)acetate To a solution of 2-iodo-4-methoxyaniline (20.0 g, 80 mmol), ethyl-2-(2-oxocyclopentyl)acetate (20.5 g, 120 mmol, 1.5 eq) and tetraethyl orthosilicate (21.7 g, 104 mmol, 1.3 eq) in anhydrous DMF (100 mL), was added pyridine p-toluenesulfonate (0.807 g, 3.21 mmol, 0.04 eq). The dark brown solution was stirred at 135° C. for 5 h under N$_2$, allowed to cool to 100° C. and then added DIPEA (31.1 g, 241 mmol, 3 eq) followed by Pd(OAc)$_2$ (0.541 g, 2.41 mmol, 0.03 eq). The resulting mixture was stirred at 120° C. for 22 h under N$_2$, concentrated under reduced pressure. The residue was taken up in DCM, filtered through a plug of silica and the solvent was evaporated under reduced pressure. The residue was purified by silica gel column chromatography to give the title compound. LCMS m/z=274.4 [M+H]$^+$.

Step B: Preparation of Ethyl 2-(7-Hydroxy-1,2,3,4-tetrahydrocyclopenta[b]indol-3-yl)acetate DCM (305 mL) was transferred to a 1 L 3-necked round-bottomed flask and cooled to −11° C. (internal) (ice acetone bath). BBr$_3$ (72.0 mL, 761 mmol) was added to the DCM with stirring. A solution of ethyl 2-(7-methoxy-1,2,3,4-tetrahydrocyclopenta[b]indol-3-yl)acetate (41.62 g, 152 mmol) in DCM (145 mL) was added in drops maintaining the internal temperature of about −5 to 0° C. After the addition the reaction was stirred for 1 h below about 0° C. The reaction mixture was slowly poured into mixture of ice (400 mL) and saturated K$_2$CO$_3$ (400 mL) and stirred well (pH maintained at 9-7). The organic layer was separated, washed with brine (1×100 mL), dried over MgSO$_4$, filtered and concentrated under reduced pressure. The residual brown oil was purified by passing it through a pad of silica gel to give the title compound (8.03 g). LCMS m/z=260.2.

Example 6

Preparation of (R/S)-Ethyl 2-(7-(4-Cyclopentyl-3-(trifluoromethyl)benzyloxy)-1,2,3,4-tetrahydrocyclopenta[b]indol-3-yl)acetate (Compound of Formula (IIk), Wherein R$^3$ is Ethyl)

Method 1

Preparation of (R/S)-Ethyl 2-(7-(4-Cyclopentyl-3-(trifluoromethyl)benzyloxy)-1,2,3,4-tetrahydrocyclopenta[b]indol-3-yl)acetate Ethyl 2-(7-hydroxy-1,2,3,4-tetrahydrocyclopenta[b]indol-3-yl)acetate (24.0 g, 1.0 eq) was charged into a 1 L, 3-neck round bottom flask set in a heating mantel with a J-KEM controller. Cesium carbonate (39.2 g, 1.3 eq) was charged into the flask. Acetonitrile (250 mL) was charged into the flask and the reaction mixture was stirred with a magnetic stir bar. 4-(Chloromethyl)-1-cyclopentyl-2-(trifluoromethyl) benzene (26.7 g, 1.1 eq) was charged slowly over 20 minutes while heating the reaction mixture. The internal temperature at the beginning of the charge was about 21° C. and the internal temperature at the end of the charge was about 82° C. Reaction temperature was maintained at 78° C. 1PC taken after 2.0 hours indicated 95% conversion to product by HPLC. After 2.5 hours the reaction temperature was reduced from about 78° C. to about 54° C. over 33 minutes. 125 mL of acetonitrile (5 vol) was heated to 50° C. in a 250 mL Ehrlenmeyer flask. Celite® was placed in a glass sintered filter funnel and acetonitrile used to wash and pack the filter aid. The acetonitrile wash was discarded to waste. The packed Celite® was approximately 0.5 inches. The reaction mixture was cooled to about 54° C. and filtered through the Celite® filter aid in the glass sintered filter funnel and washed with the 125 mL acetonitrile heated to about 50° C. The acetonitrile filtrate was stirred under nitrogen at ambient temperature for 1.0 hour. The filtrate was concentrated under reduced pressure at about 24° C. forming a thick slurry; 260 mL of distillate was collected. 375 mL of methanol was used to transfer the slurry into a 1 L round bottom flask. The slurry was stirred under nitrogen at ambient temperature for 15.0 hours. The slurry was placed in an ice/salt bath and stirred under nitrogen for 1.2 hours. 150 mL of methanol was placed in an ice/salt bath. The solids were filtered in a Whatman disposable filter cup at about −11° C. and washed with chilled methanol (125 mL). The off-white solids were placed in a vacuum oven set at about 29° C. for 22.5 hours to afford 35.7 g of ethyl 2-(7-(4-cyclopentyl-3-(trifluoromethyl)benzyloxy)-1,2,3,4-tetrahydrocyclopenta[b]indol-3-yl)acetate (Compound of Formula (IIk), wherein R$^3$ is ethyl), 79% yield with 99.57 Area % by HPLC.

$^1$H NMR (400 MHz, Acetone-d$_6$) δ 1.23 (t, J=7.1 Hz, 3H), 1.61-1.80 (m, 4H), 1.83-1.95 (m, 2H), 2.05-2.19 (m, 2H), 2.53-2.61 (m, 2H), 2.64-2.84 (m, 4H), 3.31-3.42 (m, 1H), 3.51-3.60 (m, 1H), 4.15 (q, J=7.1, 2H), 5.16 (s, 2H), 6.79 (dd, J=2.5, 8.8 Hz, 1H), 7.01 (d, J=2.4 Hz, 1H), 7.27 (d, J=8.8 Hz, 1H), 7.63 (d, J=8.1 Hz, 1H), 7.73 (d, J=8.2 Hz, 1H), 7.77 (s, 1H), 9.51 (s, 1H). LCMS m/z calcd for C$_{28}$H$_{30}$F$_3$NO$_3$: 485.54. Found: 486.4 (M+H)$^+$.

Method 2

Preparation of (R/S)-Ethyl 2-(7-(4-Cyclopentyl-3-(trifluoromethyl)benzyloxy)-1,2,3,4-tetrahydrocyclopenta[b]indol-3-yl)acetate To a solution of ethyl 2-(7-hydroxy-1,2,3,4-tetrahydrocyclopenta[b]indol-3-yl)acetate (50.0 mg, 0.193 mmol) and 4-(chloromethyl)-1-cyclopentyl-2-(trifluoromethyl)benzene (152.0 mg, 0.578 mmol) in DMF (3 mL) was added cesium carbonate (75.0 mg, 0.231 mmol). The mixture was stirred at room temperature overnight, filtered through Celite®, and concentrated under reduced pressure. The residue was purified by HPLC to give the title compound as a light pink oil (38.7 mg). LCMS m/z=486.5 [M+H]$^+$.

Method 3

Preparation of (R/S)-Ethyl 2-(7-(4-Cyclopentyl-3-(trifluoromethyl)benzyloxy)-1,2,3,4-tetrahydrocyclopenta[b]indol-3-yl)acetate In a 2 L, 3-necked, round-bottomed flask under nitrogen atmosphere were placed ethyl 2-(7-hydroxy-1,2,3,4-tetrahydrocyclopenta[b]indol-3-yl)acetate (55.85 g, 215 mmol), cesium carbonate (84.2 g, 258 mmol), 4-(chloromethyl)-1-cyclopentyl-2-(trifluoromethyl)benzene (68 g, 259 mmol) in DMA (670 mL). The mixture was stirred for 15 minutes at room temperature and heated at 50° C. overnight. The mixture was cooled down to room temperature and filtered. The filtrate was concentrated under vacuum. Hexanes (400 mL) were added and the mixture was heated to 40° C. to give a dark solution. The solution was cooled down to room temperature over the weekend. The mixture was concentrated in vacuo and dried under vacuum to give the title compound (129.7 g). LCMS m/z=486.2.

Example 7

Preparation of (R)-2-(7-(4-Cyclopentyl-3-(trifluoromethyl)benzyloxy)-1,2,3,4-tetrahydrocyclopenta[b]indol-3-yl)acetic acid (Compound of Formula (Ia)) and L-Arginine Salt of (R)-2-(7-(4-cyclopentyl-3-(trifluoromethyl)benzyloxy)-1,2,3,4-tetrahydrocyclopenta[b]indol-3-yl)acetic acid (Compound of Formula (Ia))

Method 1

Preparation of (R)-2-(7-(4-Cyclopentyl-3-(trifluoromethyl)benzyloxy)-1,2,3,4-tetrahydrocyclopenta[b]indol-3-yl)acetic acid (Compound of Formula (Ia)) and L-Arginine Salt Thereof Step A: Preparation of (R)-2-(7-(4-cyclopentyl-3-(trifluoromethyl)benzyloxy)-1,2,3,4-tetrahydrocyclopenta[b]indol-3-yl)acetic acid To a solution of rac-ethyl 2-(7-(4-cyclopentyl-3-(trifluoromethyl)benzyloxy)-1,2,3,4-tetrahydrocyclopenta[b]indol-3-yl)acetate (20.00 g, 41.19 mmol) in acetonitrile (185 ml) in a 500 mL three-neck RBF equipped with magnetic stir bar, N$_2$ inlet, thermocouple, and condenser was added potassium phosphate buffer (15 ml, 1.0 M, pH=7.80) and followed by addition of lipase B, *Candida antarctica*, immobilized recombinant from yeast (1.0 g, 5865 U/g, 5865 U). The resultant yellow suspension was stirred at about 40° C. under N$_2$ for 16 hours. To the mixture, 1 M citric acid was added to adjust the pH to 3.96 which was then filtered on a Whatman filter cup. The solids were washed with ACN (3×15 mL). The combined filtrate and washings were concentrated at about 30° C. under vacuum to give an orange residue, which was partitioned between EtOAc (60 mL) and brine (60 mL). The layers were separated and the aqueous layer was extracted with EtOAc (2×40 mL). The combined organic layers were washed with H$_2$O (2×80 mL), brine (2×80 mL), dried over Na$_2$SO$_4$, decanted, and concentrated at 30° C. under vacuum to give an orange oil, which was dried under vacuum at room temperature overnight to give a light orange oil (22.203 g) containing (R)-2-(7-(4-cyclopentyl-3-(trifluoromethyl)benzyloxy)-1,2,3,4-tetrahydrocyclopenta[b]indol-3-yl)acetic acid. The crude was assayed to be 41.41 wt % (9.194 g) with 99.42% ee.

Step B: Preparation of L-Arginine Salt of (R)-2-(7-(4-Cyclopentyl-3-(trifluoromethyl)benzyloxy)-1,2,3,4-tetrahydrocyclopenta[b]indol-3-yl)acetic acid (Compound of Formula (Ia))

To the crude (21.837 g) (R)-2-(7-(4-cyclopentyl-3-(trifluoromethyl)benzyloxy)-1,2,3,4-tetrahydrocyclopenta[b]indol-3-yl)acetic acid (41.41% w/w; 9.043 g, 19.77 mmol) containing the (S)-isomer as the ester impurity in a 200 mL round bottom flask was added IPA (150.72 mL). The mixture was heated at 60° C. under N$_2$ till the oily residue dissolved completely. The resultant orange solution was heated at about 60° C. for 5 min. Seeds of L-arginine salt of (R)-2-(7-(4-cyclopentyl-3-(trifluoromethyl)benzyloxy)-1,2,3,4-tetrahydrocyclopenta[b]indol-3-yl)acetate (362 mg) were added. The seeds were suspended in the orange solution. A 2.27 M aqueous solution of L-arginine (8.709 mL, 3.44 g, 19.77 mmol) pre-warmed to about 60° C. was added into the mixture dropwise over 30 min. A light yellow precipitate formed gradually during the addition. The suspension was stirred for about an additional 30 min. The temperature of the suspension was allowed to drop at about 0.4° C. per minute to room temperature. The mixture was agitated occasionally at room temperature overnight. The suspension was filtered and the cake was washed with IPA (3×6 mL) and EtOAc (3×15 mL). The filter cake was dried at room temperature under vacuum overnight to give L-arginine salt of (R)-2-(7-(4-cyclopentyl-3-(trifluoromethyl)benzyloxy)-1,2,3,4-tetrahydrocyclopenta[b]indol-3-yl)acetate as a white solid (11.631 g, 44.7%): HPLC 99.38 Area %, 99.6% ee. TGA, PXRD, PLM, SEM and DSC indicated the solid as a non-solvated, crystalline compound with an average aggregates size of 18.05 microns and a melting point of 202.69° C.

$^1$H NMR (400 MHz, DMSO-d$_6$) δ ppm 1.53-1.80 (m, 8H), 1.81-1.92 (m, 2H), 1.93-2.13 (m, 3H), 2.19 (dd, J=15.12, 8.18 Hz, 1H), 2.46 (dd, J=15.12, 6.61 Hz, 1H), 2.57-2.77 (m, 3H), 3.03-3.19 (m, 2H), 3.21-3.35 (m, 2H), 3.39-3.51 (m, 1H), 5.13 (s, 21-1), 6.70 (dd, J=8.75, 2.40 Hz, 1H), 6.93 (d, J=2.40 Hz, 1H), 7.23 (d, J=8.75 Hz, 1H), 7.64 (d, J=8.08 Hz, 1H), 7.72 (d, J=8.08 Hz, 1H), 7.74 (s, 1H), 7.10-8.70 (br. s, 6H), 10.49 (s, 1H). LCMS m/z calcd for $C_{32}H_{40}F_3N_5O_5$: 631.69. Found: 632.1 ($M_{salt}$+H)$^+$, 458.3 (100, ($M_{acid}$+H)$^+$).

Method 2

Preparation of (R)-2-(7-(4-Cyclopentyl-3-(trifluoromethyl)benzyloxy)-1,2,3,4-tetrahydrocyclopenta[b]indol-3-yl)acetic acid (Compound of Formula (Ia))

Additional procedures to prepare (R)-2-(7-(4-Cyclopentyl-3-(trifluoromethyl)benzyloxy)-1,2,3,4-tetrahydrocyclopenta[b]indol-3-yl)acetic acid (Compound of Formula (Ia)) using other lipases were utilized, for example, the following were shown to hydrolyze rac-ethyl 2-(7-(4-cyclopentyl-3-(trifluoromethyl)benzyloxy)-1,2,3,4-tetrahydrocyclopenta[b]indol-3-yl)acetate to (R)-2-(7-(4-Cyclopentyl-3-(trifluoromethyl)benzyloxy)-1,2,3,4-tetrahydrocyclopenta[b]indol-3-yl)acetic acid (Compound of Formula (Ia)). General hydrolysis conditions and % enantiomeric excess (% ee) are shown below for the following enzymes, lipase B *Candida Antarctica*, lipase *Mucor miehei* (MML), and *P. fluorescens*.

| Solvents | Enzyme* | pH | Temperature | % ee |
| --- | --- | --- | --- | --- |
| 0~25% DMF in phosphate Buffer | lipase B *Candida antarctica* | 7.5 | 22~37 C. | 38~94 |
| 0~25% DMF in phosphate Buffer | lipase *Mucor miehei* (MML) | 7.5 | 22~37 C. | 29~44 |
| 5% DMF in phosphate Buffer | *P. fluorescens* | 7.5 | 30 C. | 19~20 |

*Free enzyme (i.e., non-imMoblized)

Each of the above enzymes provided the desired (R)-2-(7-(4-Cyclopentyl-3-(trifluoromethyl)benzyloxy)-1,2,3,4-tetrahydrocyclopenta[b]indol-3-yl)acetic acid (Compound of Formula (Ia)) with varying degrees of % ee.

Example 8

Preparation of L-Arginine Salt of (R)-2-(7-(4-Cyclopentyl-3-(trifluoromethyl)benzyloxy)-1,2,3,4-tetrahydrocyclopenta[b]indol-3-yl)acetic acid Method 1

(R)-2-(7-(4-Cyclopentyl-3-(trifluoromethyl)benzyloxy)-1,2,3,4-tetrahydrocyclopenta[b]indol-3-yl)acetic acid (174.7 mg, 0.381 mmol) was dissolved in IPA (1.57 mL) and L-arginine (66.4 mg, 0.381 mmol) was added as a solution in water (263 μL). The homogeneous solution was warmed to 40° C. After 15 min at this temperature, a precipitate had formed. The reaction mixture was warmed to 70° C. causing the precipitate to dissolve. The heat bath was turned off. A precipitate began to form at 40° C. and the reaction mixture was allowed to cool to about 28° C. before collecting the solids by filtration. The solids were washed with 14% water in IPA to give the L-arginine salt of (R)-2-(7-(4-cyclopentyl-3-(trifluoromethyl)benzyloxy)-1,2,3,4-tetrahydrocyclopenta[b]indol-3-yl)acetic acid (130 mg).

Method 2

Example 8

Preparation of L-Arginine Salt of (R)-2-(7-(4-Cyclopentyl-3-(trifluoromethyl)benzyloxy)-1,2,3,4-tetrahydrocyclopenta[b]indol-3-yl)acetic acid Step A: Preparation of 1-Cyclopentyl-2-(trifluoromethyl)benzene (Compound of Formula (IIb))

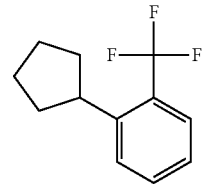 [SMILES: FC(F)(F)c1ccccc1C1CCCC1]

To a 50 L three-neck round-bottom flask equipped with a mechanical stirrer, thermocouple, and nitrogen inlet, was added dry THF (35 L) and cooled to 0-5° C. To the flask was added Iron (III) chloride (2.7 kg, 0.15 eq) portion wise over 30-60 min. and stirred for 15-30 min. resulting in a clear greenish solution. Under a nitrogen atmosphere in a dry 100 gallon glass lined reactor was added THF (87.5 L) and magnesium turnings (4.05 kg, 1.5 eq), and cooled to 0-5° C. To the THF and magnesium mixture was added the solution of FeCl$_3$ in THF at a rate to maintain the internal temperature below 10° C. To the resulting yellow/green mixture was added TMEDA (15.5 kg, 1.2 eq) at a rate to maintain the internal temperature below 20° C. The resulting reaction mixture was heated to 40-45° C. for 1 hour and a mixture of 1 bromo-2-(trifluoromethyl)benzene (25 kg, 1.0 eq) and bromocyclopentane (19.9 kg, 1.2 eq) was added to the reaction mixture at a rate to maintain an internal temperature below 25° C. The resulting reaction mixture was allowed to stir at room temperature overnight and subsequently cooled to an internal temperature of 0-5° C. To the resulting mixture was added 6 N HCl (100 L, 1.5 h) at such a rate as to maintain the internal temperature below 15° C. (caution, very exothermic). After the quench, MTBE (200 L) was added and the reactor contents was stirred for 30 min. The phases were separated and the aqueous layer back extracted with MTBE (75 L). The combined organic layers were washed with H$_2$O (50 L), brine (50 L) and dried (MgSO$_4$). The mixture was filtered through an in-line (1 micron) filter cartridge followed by an additional in-line (0.45 micron) filter cartridge into a clean dry reactor. The solvent was evaporated under vacuum (jacket≤30° C.) and co-evaporated with heptanes (2×25 L) to provide a viscous liquid. The viscous liquid was dissolved in heptanes (100 L) and passed through a silica plug (25 kg). The silica plug was eluted with heptanes (TLC, R$_f$~0.8, silica gel, heptanes) and the fractions containing the product were evaporated to provide the title compound as a yellow liquid, 11.7 kg Step B: Preparation of 4-(Chloromethyl)-1-cyclopentyl-2-(trifluoromethyl)benzene (Compound of Formula (IIc))

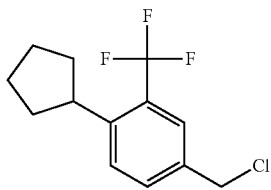 [SMILES: FC(F)(F)c1cc(CCl)ccc1C1CCCC1]

To a 100 gallon glass lined reactor equipped with a stirrer was added concentrated sulphuric acid (48.6 L) and cooled to an internal temperature between about −5 to −10° C. under an atmosphere of $N_2$. To the sulfuric acid was added thionyl chloride (26.99 kg, 2 eq) at a rate to maintain the internal temperature below −5° C. To the resulting mixture 1,3,5-trioxane (15.3 kg, 1.5 eq) was added portion wise at a rate to maintain the internal temperature below −5° C. After the addition of 1,3,5-trioxane, 1-cyclopentyl-2-(trifluoromethyl) benzene (24.0 kg) was added drop wise over a period of approximately 2-3 hours. The reaction mixture was stirred at 0° C. for approximately 3-4 hours, allowed to warm to room temperature overnight and subsequently cooled to an internal temperature of 0-5° C. To the resulting mixture was added water (316 L) drop wise over a period of approximately 5-6 hours (Note: Very exothermic). After the quench with water, the resulting aqueous mixture was extracted with MTBE (243 L and 123 L). The combined organics were washed with saturated $NaHCO_3$ (100 L), brine (100 L), water (100 L), brine (100 L), and dried ($MgSO_4$). The mixture was filtered through an in-line (1 micron) filter cartridge followed by an additional in-line (0.45 micron) filter cartridge into a clean dry reactor. The solvent was evaporated under vacuum (jacket≤30° C.) and further evaporated under vacuum at 35-40° C. The resulting oil was distilled under high vacuum to provide the title compound as a yellow liquid, 24.8 kg (83%), purity as determined by HPLC was 99.47%. $^1$H NMR conforms to reference standard.

Step C: Preparation of Ethyl 2-(2-Morpholinocyclopent-2-enylidene)acetate (Compound of Formula (IIg), Wherein $R^3$ is Ethyl)

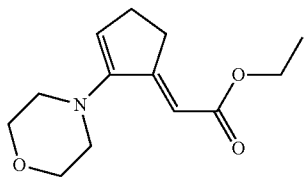 [SMILES: CCOC(=O)/C=C1\CCC=C1N1CCOCC1]

Cyclopentanone (22.00 kg), morpholine (22.88 kg) and cyclohexane (43.78 kg) were charged to a 400 L glass-lined reactor equipped with overhead agitation, jacket temperature control, a nitrogen inlet, and a Dean-Stark trap. The reactor contents were heated to about 85° C. to 95° C. for approximately 26 h while removing water using the Dean-Stark trap. The reaction to form the enamine (i.e., 4-cyclopentenylmorpholine, Compound of Formula (IIe) wherein $R^1$ and $R^2$ together with the nitrogen atom form a morpholine ring) is deemed complete when the morpholine amount is verified to be 3% by GC peak area.

The reactor contents were cooled to about 60° C. and ethyl glyoxalate (Compound of Formula (IIf) wherein $R^3$ is ethyl; 58.74 kg, 50% solution in toluene) was added to the mixture slowly so as to maintain an internal temperature of ≤80° C. The reactor contents were heated to about 85° C. to 95° C. for at least 25 hours while removing water using the Dean-Stark trap. The reaction was deemed complete when the eneamine (i.e., 4-cyclopentenylmorpholine) amount by GC was verified to be less than 0.5% by GC peak area. The cyclohexane/toluene mixture was distilled under vacuum, ethanol (261.80 kg) was charged to the reactor, and the resulting solution was again distilled under vacuum. Ethanol (34.76 kg) and water 44.00 kg) were charged to the reactor and the reactor contents stirred at 25° C. The mixture was stirred further for 6 h at about 0-5° C.

The resulting product slurry was collected by filtration, washed with aqueous ethanol (34.76 kg ethanol dissolved in 176.00 kg water). The filter-cake was further washed with water (110.00 kg), dried initially at approximately 36° C. for 1 hour under vacuum and subsequently at approximately 50° C. under vacuum for 17 h. The title compound was obtained as a tan solid (23.48 kg, 37.8% yield).

Step D: Preparation of E/Z Ethyl 2-(7-(Benzyloxy)-1,2-dihydrocyclopenta[b]indol-3(4H)-ylidene)acetate

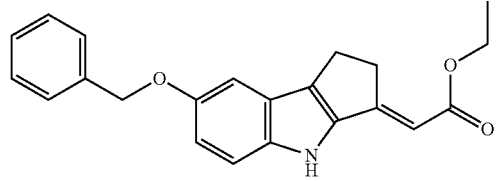 [SMILES: CCOC(=O)/C=C1\CCc2c1[nH]c1ccc(OCc3ccccc3)cc21]

To a 400 L glass-lined reactor equipped with overhead agitation, jacket temperature control, and a nitrogen inlet was added (4-(benzyloxy)phenyl)hydrazine hydrochloride (21.08 kg, 1.000 mole equiv.), ethyl 2-(2-morpholinocyclopent-2-enylidene)acetate (22.02 kg, 1.104 mole equiv.), ethanol (51.2 kg, 2.429 mass equiv.), and acetic acid (36.8 kg, 1.746 mass eq.). After the reactor contents are allowed to stand for 10 minutes, agitation and then heating to 60° C. to 65° C. (60° C. target) was started. While stirring at that temperature, samples of the reaction mixture were taken over intervals of approximately 30 minutes and analyzed by HPLC for (4-(benzyloxy)phenyl)hydrazine, ethyl 2-(2-morpholinocyclopent-2-enylidene)acetate, and hydrazone content. When (4-(benzyloxy)phenyl)hydrazine HPLC % area was <1, TFA (11.6 kg, 101.7 mol, 1.200 mole equiv., 0.550 mass equiv.) was charged over approximately 1 hour while the stirred reaction mixture was maintained at 60° C.±5° C. with reactor jacket cooling. As stirring at 60° C. to 65° C. was continued, the hydrazone and imine content of the reaction mixture was monitored by HPLC. After stirring at 60° C. to 65° C. for at least 12 hours the imine content of the reaction mixture was <5% area by HPLC, and the stirred reaction mixture was cooled to 20° C. to 25° C. over approximately 3 hours. Stirring was maintained at that temperature to allow isomerization of the Z isomer to the desired E isomer. The E isomer crystallizes from the reaction mixture. The Z isomer and E isomer % area content of the reaction mixture was monitored by HPLC during this period of stirring at 20° C. to 25° C., which was continued until the Z-isomer content of the reaction mixture was <15% area by HPLC.

The stirred reaction mixture was cooled (0° C. to 5° C.) over at least 2 hours and then filtered. The reactor was charged with ethanol (27.4 kg, 1.300 mass equiv.), which was stirred and chilled to 0° C. to 5° C. and then used in two approximately equal portions to slurry-wash the product filter cake twice. The reactor was charged with ethanol (13.8 kg, 0.655 mass equiv.), which was stirred and chilled to 0° C. to 5° C. and then used to wash the product filter cake by displacement. The reactor was charged with USP purified water (100 kg, 4.744 mass equiv.), and the temperature was adjusted to 20° C. to 25° C. The USP purified water was then used in three approximately equal portions to wash the product filter cake three times, the first two by reslurrying and the third by displacement. The reactor was charged with ethanol (16.4 kg, 0.778 mass equiv.), stirred and chilled to 0° C. to 5° C., and then used to wash the product filter cake by displacement. The washed product filter cake was dried under full vacuum first with a jacket temperature of 35° C. for 1 hour and then with a jacket temperature of 50° C. While drying continues with a jacket temperature of 50° C., the product solids are turned over every 1 hour to 3 hours, and product samples are analyzed for loss on drying (LOD) every ≥4 hours. When LOD was <1%, the product was cooled to <30° C. The yield of the title compound was 13.06 kg (37.59 mol, 44.7%).

Step E: Preparation of Ethyl 2-(7-Hydroxy-1,2,3,4-tetrahydrocyclopenta[b]indol-3-yl)acetate

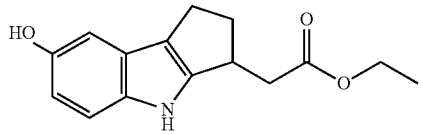 [SMILES: CCOC(=O)CC1CCc2c1[nH]c1ccc(O)cc21]

To a 200 liter Hastelloy reactor was added ethyl 2-(7-(benzyloxy)-1,2-dihydrocyclopenta[b]indol-3(4H)-ylidene)acetate (E/Z mixture, 12 kg), 10% Pd/C (50% wet with $H_2O$; 1.80 kg) and ethyl acetate (108 kg). The suspension was degassed 3× with $N_2$ and triethylamine (1.76 kg) was added. To the resulting mixture was added formic acid (3.34 kg) while maintaining the internal temperature at below 35° C. The reaction progression was followed by HPLC to monitor the complete consumption of starting material (i.e., E/Z mixture of ethyl 2-(7-(benzyloxy)-1,2-dihydrocyclopenta[b]indol-3(4H)-ylidene)acetate) and the debenzylated intermediate. After approximately 30 minutes an additional amount of formic acid (0.50 kg) was added and the combined peak area of ethyl 2-(7-(benzyloxy)-1,2-dihydrocyclopenta[b]indol-3(4H)-ylidene)acetate and the related debenzylated intermediate was determined to be <1% area by HPLC. The reactor contents were filtered through a 1.2 μm cartridge filter followed by an in-line 0.2 μm inline polishing filter. To the filtrate was added water (60 kg) and the biphasic mixture was partitioned. The organics were separated and concentrated under vacuum at approximately 60° C.±5° C. to a minimum stir volume, ethyl acetate (21.6 kg) was added and the mixture was further concentrated under vacuum to a minimum stir volume. Once again ethyl acetate (16.8 kg) was charged to the crude mixture and the resulting solution was heated to approximately 60° C. Heptanes (37.2 kg) were charged maintaining the internal temperature at 60° C. The solution was slowly cooled to approximately 0 to 5° C. and approximately 2-3 hr to facilitate crystallization. The slurry was filtered, the filter cake was reslurried in heptanes (27.12 kg) and ethyl acetate (7.08 kg). The resulting suspension was filtered and the solids dried under vacuum at approximately 40±5° C. (until the loss on drying (LOD) is <1%) to afford the title compound (6.23 kg, 70.3% yield) as a solid.

Step F: Preparation of (R/S)-Ethyl 2-(7-(4-Cyclopentyl-3-(trifluoromethyl)benzyloxy)-1,2,3,4-tetrahydrocyclopenta[b]indol-3-yl)acetate (Compound of Formula (IIk), Wherein $R^3$ is Ethyl)

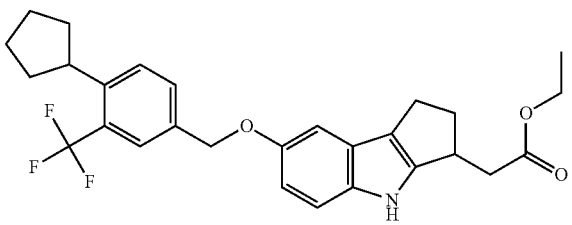 [SMILES: CCOC(=O)CC1CCc2c1[nH]c1ccc(OCc3ccc(C4CCCC4)c(C(F)(F)F)c3)cc21]

To a 50 liter glass reactor containing ethyl 2-(7-hydroxy-1,2,3,4-tetrahydrocyclopenta[b]indol-3-yl)acetate (2.000 kg, 1.000 equiv.) was added cesium carbonate (3.266 kg, 1.300 equiv.) and acetonitrile (15.720 kg) under nitrogen. To the resulting mixture was added 4-(chloromethyl)-1-cyclopentyl-2-(trifluoromethyl)benzene (2.228 kg, 1.100 equiv.) over approximately one hour while maintaining the stirred reactor contents at 40° C.±5° C. After the addition of 4-(chloromethyl)-1-cyclopentyl-2-(trifluoromethyl)benzene the reactor contents were heated to 65° C.±5° C. with stirring until the concentration of ethyl 2-(7-hydroxy-1,2,3,4-tetrahydrocyclopenta[b]indol-3-yl)acetate in the reaction mixture was less than 2.0% area by HPLC. The reaction mixture was cooled to 50° C.±5° C. and filtered under nitrogen through a fine filter cloth with suction to remove cesium salts (Note: ethyl 2-(7-(4-cyclopentyl-3-(trifluoromethyl)benzyloxy)-1,2,3,4-tetrahydrocyclopenta[b]indol-3-yl)acetate may precipitate below 30° C.). The filter cake was washed with fresh hot (50° C.±5° C.) acetonitrile (5.658 kg divided in approximately three equal portions). The filtrates were returned to the reactor. The combined filtrates were concentrated by vacuum distillation with a jacket temperature of 60° C.±10° C. To the reactor was added ethyl alcohol (3.156 kg) and once again concentrated with stirring by vacuum distillation with a jacket temperature of 60° C.±10° C. Once again, ethyl alcohol (3.156 kg) was added to the reactor and the contents were concentrated by vacuum distillation with a jacket temperature of 60° C.±10° C. to a reactor volume of approximately 14 L. The stirred reactor contents were cooled to 0° C. f 5° C. and the temperature maintained for 4 hours to facilitate the crystallization of the product. The resulting slurry was filtered. The filter cake was washed with cold 0° C.±5° C. ethyl alcohol (2×3.156 kg). The filter cake was dried under vacuum at 35° C.±5° C. until the weight loss over hour was to provide 3.0943 kg (81.0% yield) of the title compound as a solid.

Step G: Preparation of (R)-2-(7-(4-cyclopentyl-3-(trifluoromethyl)benzyloxy)-1,2,3,4-tetrahydrocyclopenta[b]indol-3-yl)acetic acid

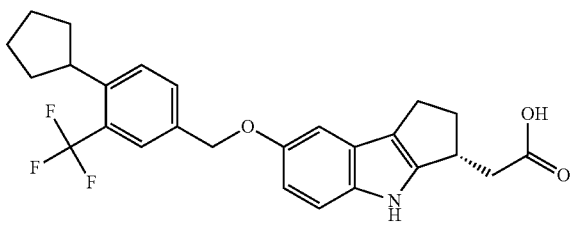 [SMILES: O=C(O)C[C@H]1CCc2c1[nH]c1ccc(OCc3ccc(C4CCCC4)c(C(F)(F)F)c3)cc21]

A 1.0 M buffer solution was prepared containing potassium phosphate monobasic (29.1 g, 0.0335 equiv.) in USP purified water (213 g) and potassium phosphate dibasic (368.2 g, 0.331 equiv.) in USP purified water (2.107 g). To a 50 liter glass reactor was added ethyl 2-(7-(4-cyclopentyl-3-(trifluoromethyl)benzyloxy)-1,2,3,4-tetrahydrocyclopenta[b]indol-3-yl)acetate (3.094 kg, 1.000 equiv.), Lipase B, *Candida antarctica*, immobilized (88.18 g, 293250 units/kg of ethyl ester starting material) and acetonitrile (22.32 kg). To the stirred contents of the reactor was added the previously prepared 1.0 M potassium phosphate buffer. The resulting mixture was stirred under nitrogen at a temperature of 40° C.±5° C. until the (R)-2-(7-(4-cyclopentyl-3-(trifluoromethyl)benzyloxy)-1,2,3,4-tetrahydrocyclopenta[b]indol-3-yl)acetic acid concentration was ≥35% area as determined by HPLC (Note: although the reaction usually is complete after about 10 hours, the reaction mixture may be held at 40° C. t 5° C. overnight). The stirred reactor contents were cooled to 25° C. f 5° C. and the pH was adjusted to between 4 and 5 by addition of a solution of citric acid (278.5 g, 0.228 equiv.) dissolved in USP purified water (1.454 kg). The reactor contents were filtered to remove immobilized lipase and phosphate and citrate salts. The reactor and solids were washed with acetonitrile (4.827 kg) and the combined filtrates were added backed into the reactor. The stirred reactor contents were concentrated to a volume of 1.0 L to 2.0 L by vacuum distillation at a jacket temperature of 55° C. f 5° C. To the reactor was added ethyl acetate (5.582 kg) and USP purified water (6.188 kg). The contents were stirred at 20° C.±5° C. for at least 10 minutes and a solution of sodium chloride (1 kg) in USP purified water (1 kg) was added to facilitate phase separation. After phase separation was complete, the lower aqueous layer was drained. A solution of sodium chloride (5.569 kg) in USP purified water (12.38 kg) was divided in two approximately equal portions and the ethyl acetate phase was washed (2×). The ethyl acetate phase was transferred into a carboy and the reactor was rinsed with ethyl acetate (838.5 g) and added to the carboy containing the ethyl acetate phase. The reactor was washed sequentially with USP purified water (12.38 kg), acetone (4.907 kg), and ethyl acetate (838.5 g) and the ethyl acetate mixture from the carboy was transferred back to the reactor and concentrated with stirring to a volume of 1 L to 2 L by vacuum distillation at a jacket temperature of 55° C.±5° C. To the reactor was added 2-propanol (14.67 kg) and after stirring the resulting mixture was concentrated to a volume of 1 L to 2 L by vacuum distillation at a jacket temperature of 55° C.±5° C. To the reactor was added 2-propanol (7.333 kg) and heated with stirring at 60° C.±5° C. until the contents dissolved. The stirred reactor contents were cooled to 20° C.±5° C. and filtered through a medium-porosity fritted-glass filter to remove any inorganic solids to provide a 2-propanol solution containing 1.3188 kg of the title compound.

Step H: Preparation of L-Arginine Salt of (R)-2-(7-(4-Cyclopentyl-3-(trifluoromethyl)benzyloxy)-1,2,3,4-tetrahydrocyclopenta[b]indol-3-yl)acetic acid (Compound of Formula (Ia))

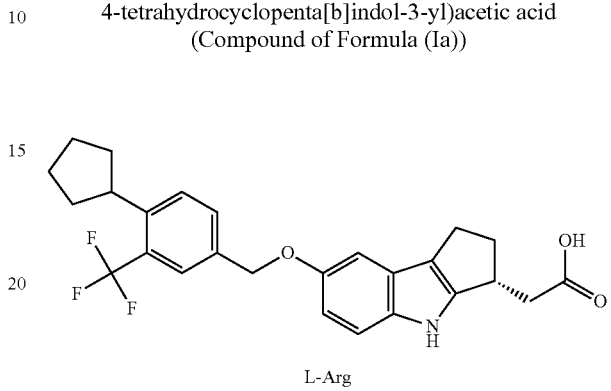

L-Arg

To a 50 liter glass reactor containing the 2-propanol solution prepared in Step G of (R)-2-(7-(4-cyclopentyl-3-(trifluoromethyl)benzyloxy)-1,2,3,4-tetrahydrocyclopenta[b]indol-3-yl)acetic acid (1.3188 kg, 1.000 equiv.) was added an additional amount of 2-propanol (6.3389 kg) to adjust the total volume to approximately 16.7 L/kg of (R)-2-(7-(4-cyclopentyl-3-(trifluoromethyl)benzyloxy)-1,2,3,4-tetrahydrocyclopenta[b]indol-3-yl)acetic acid. The reactor contents were stirred and heated to 60° C.±5° C. To the reactor was added seed material (L-arginine salt of (R)-2-(7-(4-cyclopentyl-3-(trifluoromethyl)benzyloxy)-1,2,3,4-tetrahydrocyclopenta[b]indol-3-yl)acetic acid, 26.4 g, 0.0145 equiv.). The reactor contents were stirred for approximately 5 minutes at 60° C.±5° C. and a solution of L-arginine (502.5 g, 1.000 equiv.) in USP purified water (1.27 kg) preheated to 60° C.±5° C. was added over approximately 1 hour while maintaining the stirred reactor contents at 60° C.±5° C. The stirring of the reactor contents at 60° C.±5° C. was maintained for approximately 1 hour and then allowed to cool at an approximate rate of 0.2° C./min to 1.0° C./min. to a temperature of 25° C.±5° C. Once at approximately 25° C. the contents of the reactor were stirred for approximately 1 hour maintaining the temperature of 25° C.±5° C. The resulting slurry was filtered and the filter cake was washed with 2-propanol (6.2511 kg divided in three approximately equal portions) and with ethyl acetate (13.560 kg divided in six approximately equal portions. The filter cake was dried under vacuum at 40° C.±5° C. (until the weight loss over ≥1 hour is ≤2%) to provide 1.657 kg of the title compound (32.9% yield) as a crystalline solid.

HPLC purity: 99.64 Area %; Enantiomeric purity: 99.3%; DSC melting onset temperature 203.46° C.; TGA Weight Loss out to ~110° C. was 0.05%. NMR confirms the structure of the L-salt.

Five additional lots of the L-arg salt have been prepared using substantially this same synthetic method as described above, the DSC melting onset temperatures for a sample from each of the lots is as follows: 203.96° C., 203.00° C., 203.11° C., 203.79° C. and 203.97° C.; the TGA Weight Loss out to ~110° C. for a sample from each of the lots is as follows: 0.04%, 0.04%, 0.03%, 0.10%, and 0.12%.

Example 9

Preparation of the Calcium salt of (R)-2-(7-(4-Cyclopentyl-3-(trifluoromethyl)benzyloxy)-1,2,3,4-tetrahydrocyclopenta[b]indol-3-yl)acetic acid Prior to use, (R)-2-(7-(4-cyclopentyl-3-(trifluoromethyl)benzyloxy)-1,2,3,4-tetrahydrocyclopenta[b]indol-3-yl)acetic acid, was slurried in acetonitrile overnight, filtered and dried to produce a crystalline form. To the crystalline form (40 mg) was added acetonitrile (1 mL) and the mixture was warmed to 60° C. The counterion was added by adding 20 μL of calcium acetate solution (2 M) and 20 μL of water then seeding with crystalline salt and allowing to slowly cool to room temperature. The resulting solid was filtered and dried to give the calcium salt of (R)-2-(7-(4-cyclopentyl-3-(trifluoromethyl)benzyloxy)-1,2,3,4-tetrahydrocyclopenta[b]indol-3-yl)acetic acid as a white solid.

Example 10

The Effect of (R)-2-(7-(4-Cyclopentyl-3-(trifluoromethyl)benzyloxy)-1,2,3,4-tetrahydrocyclopenta[b]indol-3-yl)acetic acid (Compound of Formula (Ia)) in the Peripheral Lymphocyte Lowering (PLL) Assay A. Mouse PLL Assay.

Animals:

Male BALB/c mice (Charles River Laboratories, Wilmington, Mass.) were housed four per cage and maintained in a humidity-controlled (40 to 60%) and temperature-controlled (68 to 72° F.) facility on a 12 h:12 h light/dark cycle (lights on at 6:30 am) with free access to food (Harlan Teklad, Orange, Calif., Rodent Diet 8604) and water. Mice were allowed one week of habituation to the animal facility before testing.

PLL Assay:

Mice were given a 1.00 mg/kg oral dose of the (R)-2-(7-(4-cyclopentyl-3-(trifluoromethyl)benzyloxy)-1,2,3,4-tetrahydrocyclopenta[b]indol-3-yl)acetic acid or dosing vehicle (0.5% methylcellulose in sterile water) in a total volume of 10 mL/kg. Peripheral blood samples were collected at 5 hours post-dose. The mice were anesthetized with isoflurane and blood was collected via cardiac puncture. A complete cell count (CBC), including lymphocyte count, was obtained using a CELL-DYN® 3700 (Abbott Laboratories, Abbott Park, Ill.) instrument. Results are presented in FIG. 1, in which peripheral blood lymphocyte (PBL) count is shown for the 5 hour group. Reduction of the PBL count by the test compound in comparison with vehicle is indicative of the test compound exhibiting activity or inducing peripheral lymphocyte lowering. It is apparent from inspection of FIG. 1 that (R)-2-(7-(4-cyclopentyl-3-(trifluoromethyl)benzyloxy)-1,2,3,4-tetrahydrocyclopenta[b]indol-3-yl)acetic acid exhibited activity for inducing PBL lowering (lymphopenia) in the mouse.

B. Rat PLL Assay.

Animals:

Male Sprague-Dawley rats (7 weeks of age at start of study) (Charles River Laboratories) were housed two per cage and maintained in a humidity-controlled (40-60%) and temperature-controlled (68-72° F.) facility on a 12 h:12 h light/dark cycle (lights on at 6:30 am) with free access to food (Harlan Teklad, Orange, Calif., Rodent Diet 8604) and water. Rats were allowed one week of habituation to the animal facility before testing.

Figure 2:
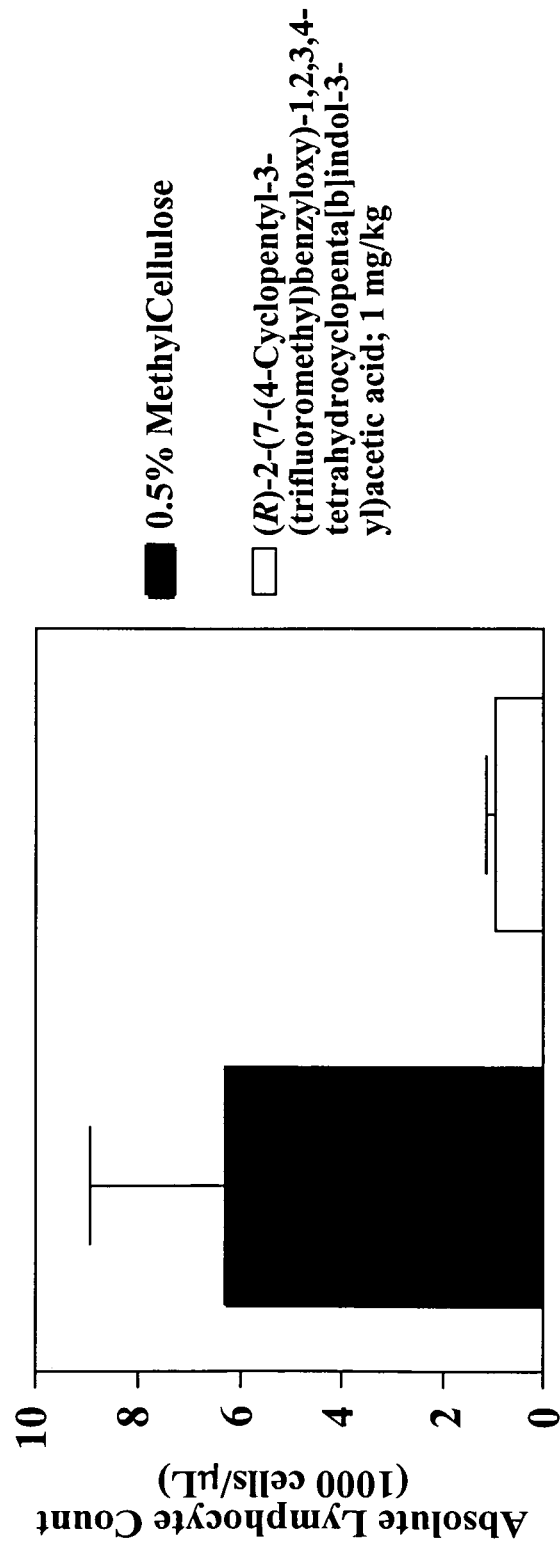
FIG. 2 shows the effect of (R)-2-(7-(4-cyclopentyl-3-(trifluoromethyl)benzyloxy)-1,2,3,4-tetrahydrocyclopenta[b]indol-3-yl)acetic acid (Compound of Formula (Ia)) in the Peripheral Lymphocyte Lowering (PLL) Assay after a 1 mg/kg oral dose in male Sprague-Dawley rats.

PLL Assay:

Rats were given a 1.00 mg/kg oral dose of (R)-2-(7-(4-cyclopentyl-3-(trifluoromethyl)benzyloxy)-1,2,3,4-tetrahydrocyclopenta[b]indol-3-yl)acetic acid, or dosing vehicle (0.5% methylcellulose in sterile water) in a total volume of 1.00 mL/kg. Peripheral blood samples were collected at 5 hours post-dose. Blood was collected via indwelling catheter. A complete cell count (CBC), including lymphocyte count, was obtained using a CELL-DYN® 3700 (Abbott Laboratories, Abbott Park, Ill.) instrument. Results are presented in FIG. 2, in which peripheral blood lymphocyte (PBL) count is shown for the 5 hour group. Reduction of the PBL count by the test compound in comparison with vehicle is indicative of the test compound exhibiting activity or inducing peripheral lymphocyte lowering. It is apparent from inspection of FIG. 2 that (R)-2-(7-(4-cyclopentyl-3-(trifluoromethyl)benzyloxy)-1,2,3,4-tetrahydrocyclopenta[b]indol-3-yl)acetic acid exhibited activity for inducing PBL lowering (lymphopenia) in the rat.

Example 11

The Effect of (R)-2-(7-(4-Cyclopentyl-3-(trifluoromethyl)benzyloxy)-1,2,3,4-tetrahydrocyclopenta[b]indol-3-yl)acetic acid in an arthritis rat model Female Lewis rats were used in this study. Acclimated animals were anesthetized with isoflurane and given the first collagen injection (day 0). On day 6, they were anesthetized again for the second collagen injection. Collagen was prepared by making a 4 mg/mL solution in 0.01 N acetic acid. Equal volumes of collagen and incomplete Freund's adjuvant were emulsified by hand mixing until a bead of this material held its form when placed in water. Each animal received 300 μL of the mixture each time, spread over 3 subcutaneous sites on the back.

Figure 3:
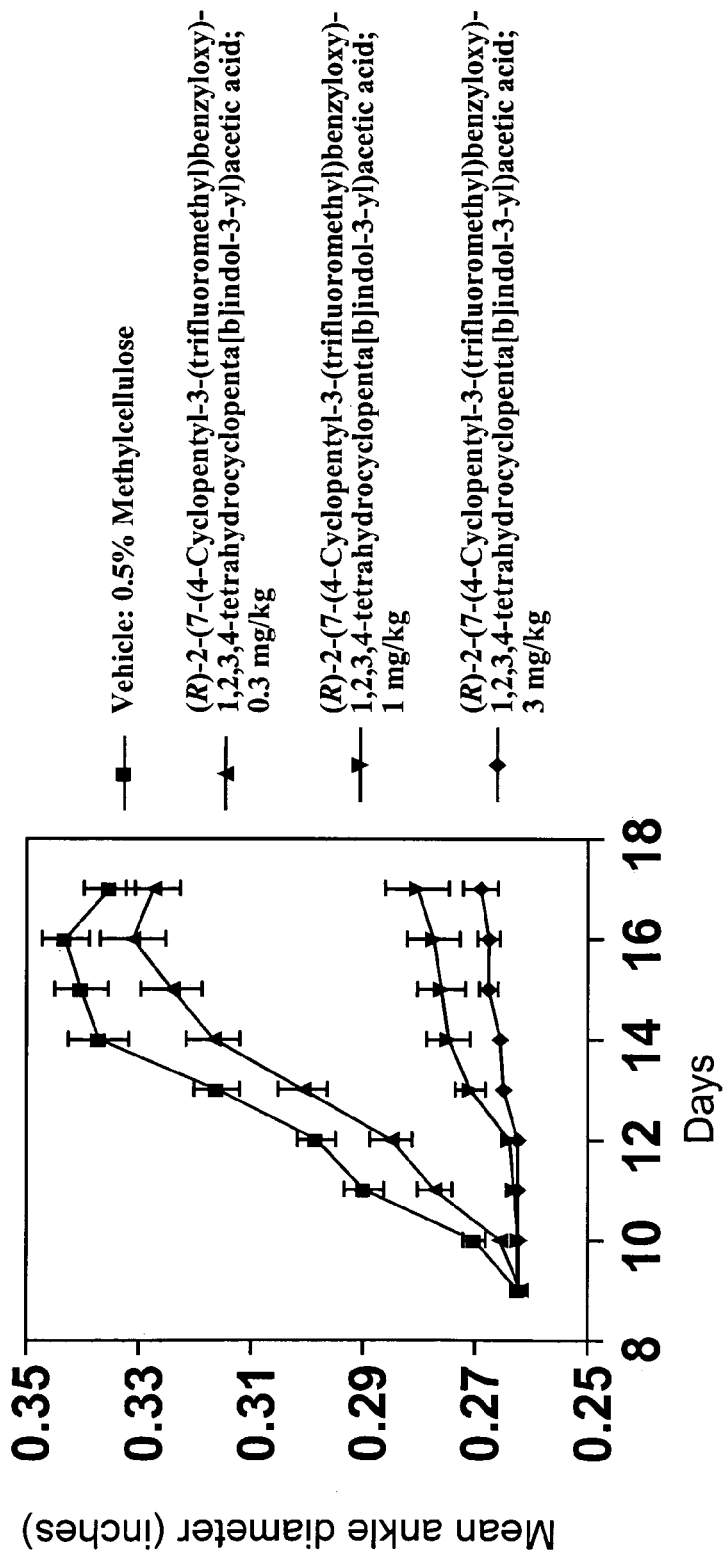
FIG. 3 shows the reduction of mean ankle diameter after 0.3 mg/kg, 1 mg/kg, and 3 mg/kg dosing of (R)-2-(7-(4-cyclopentyl-3-(trifluoromethyl)benzyloxy)-1,2,3,4-tetrahydrocyclopenta[b]indol-3-yl)acetic acid (Compound of Formula (Ia)) in the female Lewis rat collagen-induced arthritis assay.

Treatment (p.o., q. d., 5 mL/kg dosing volume) began on day 0 and continued through day 16 with vehicle or compounds given at 24 h intervals. Rats were weighed on days 0, 3, 6 and 9 through 17 and caliper measurements of the ankles taken on days 9 through 17. The compound, (R)-2-(7-(4-cyclopentyl-3-(trifluoromethyl)benzyloxy)-1,2,3,4-tetrahydrocyclopenta[b]indol-3-yl)acetic acid, was dosed at 0.3, 1 and 3 mg/kg. Results are presented in FIG. 3. It is apparent from inspection of FIG. 3 that (R)-2-(7-(4-cyclopentyl-3-(trifluoromethyl)benzyloxy)-1,2,3,4-tetrahydrocyclopenta[b]indol-3-yl)acetic acid exhibited activity for reducing mean ankle diameter in the rat.

Example 12

The Effect of (R)-2-(7-(4-Cyclopentyl-3-(trifluoromethyl)benzyloxy)-1,2,3,4-tetrahydrocyclopenta[b]indol-3-yl)acetic acid on Experimental Autoimmune Encephalomyelitis (EAE)

A compound of the invention can be shown to have therapeutic efficacy in multiple sclerosis by showing it to have therapeutic efficacy in experimental autoimmune encephalomyelitis (EAE), an animal model for multiple sclerosis. In certain exemplary well-established models, EAE is induced in rodents by injection of myelin oligodendrocyte glycoprotein (MOG) peptide, by injection of myelin basic protein (MBP) or by injection of proteolipid protein (PLP) peptide.

A. MOG-Induced EAE in Mice.

Animals:

Female C57BL/6 mice (8 to 10 weeks of age at start of study) (Jackson Laboratory, Bar Harbor, Me.) were housed four per cage and maintained in a humidity-controlled (40-60%) and temperature-controlled (68-72° F.) facility on a 12 h:12 h light/dark cycle (lights on at 6:30 am) with free access to food (Harlan Teklad, Orange, Calif., Rodent Diet 8604) and water. Mice were allowed one week of habituation to the animal facility before testing.

Induction of EAE:

Mice were immunized subcutaneously, 50 μL per hind flank, with a total of 100 μg $MOG_{35-55}$ peptide emulsified 1:1 with Complete Freund's adjuvant containing 4 mg/mL heat-killed *Mycobacterium tuberculosis*. Mice also received 200 ng pertussis toxin intraperitoneally on the day of immunization and 48 h later.

Clinical Scoring:

Severity of disease symptoms was scored as follows (in increasing order of severity): 0=normal; 1=limp tail OR hind limb weakness; 2=limp tail AND limb weakness/weakness of 2 or more limbs; 3=severe limb weakness or single limb paralysis; 432 paralysis of 2 or more limbs; 5=death.

Figure 4:
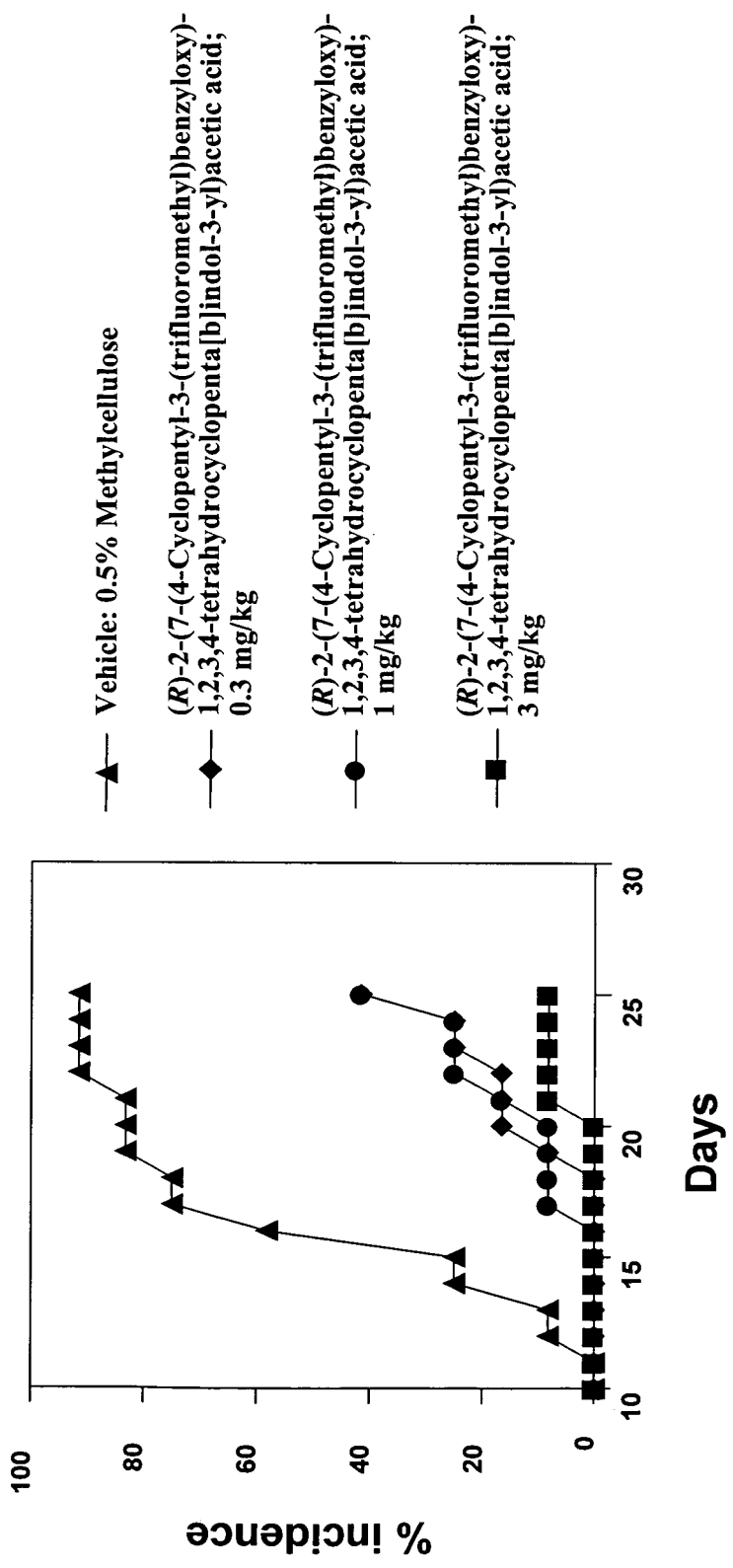
FIG. 4 shows the effect of (R)-2-(7-(4-cyclopentyl-3-(trifluoromethyl)benzyloxy)-1,2,3,4-tetrahydrocyclopenta[b]indol-3-yl)acetic acid (Compound of Formula (Ia)) in the experimental autoimmune encephalomyelitis (EAE) assay after daily oral dosing of 0.3 mg/kg, 1 mg/kg, and 3 mg/kg from day 3 to day 21.

Drug Treatment:

Mice were dosed orally, with vehicle or (R)-2-(7-(4-cyclopentyl-3-(trifluoromethyl)benzyloxy)-1,2,3,4-tetrahydrocyclopenta[b]indol-3-yl)acetic acid, once a day from day 3 until day 21. Dosing volume is 5 mL/kg. The compound, (R)-2-(7-(4-cyclopentyl-3-(trifluoromethyl)benzyloxy)-1,2,3,4-tetrahydrocyclopenta[b]indol-3-yl)acetic acid, was dosed at 0.3 mg/kg, 1 mg/kg and 3 mg/kg. Mice were weighed daily. Mice were monitored daily from day 7 onward for disease symptoms. After the last dose on day 21, disease progression was monitored daily for 2 more weeks. Reduction of the severity of disease symptoms by (R)-2-(7-(4-cyclopentyl-3-(trifluoromethyl)benzyloxy)-1,2,3,4-tetrahydrocyclopenta[b]indol-3-yl)acetic acid in comparison with vehicle was indicative of the test compound exhibiting therapeutic efficacy in EAE. It is apparent from inspection of FIG. 4 that (R)-2-(7-(4-cyclopentyl-3-(trifluoromethyl)benzyloxy)-1,2,3,4-tetrahydrocyclopenta[b]indol-3-yl)acetic acid exhibited activity in the mouse EAE assay.

Example 13

Effects of Compounds on Cardiac Telemetry in the Rat

Animals:

Male Sprague-Dawley rats (250-300 g at time of surgery) were implanted by Charles River Laboratories (Wilmington, Mass.) with cardiac transmitting devices (Data Sciences PhysioTel C50-PXT) into the peritoneal space, with a pressure-sensing catheter inserted into the descending aorta. Rats are allowed at least one week to recover. Rats were housed in individual cages and maintained in a humidity-controlled (30-70%) and temperature-controlled (20-22° C.) facility on a 12 h:12 h light/dark cycle (lights on at 7:00 am) with free access to food (Harlan-Teklad, Orange, Calif., Rodent Diet 8604) and water. Rats were allowed one week of habituation to the animal facility before testing.

Measurement of Cardiovascular Parameters:

The implanted transmitting devices transmitted continuous measurements of blood pressure (systolic, diastolic, mean arterial, pulse), heart rate, body temperature, and motor activity in freely moving conscious animals. These data were transmitted via radiofrequency to a computer which binned the data into min averages using DataSciences ART software. Telemetry recording occurred over a 21-h period, starting at noon and continuing until 9:00 am the following day. A maximum of eight rats were tested at a time, and the same eight rats were utilized for all treatment groups in a within-subject design.

Drug Treatment:

Rats were injected orally with vehicle (PEG400) and (R)-2-(7-(4-cyclopentyl-3-(trifluoromethyl)benzyloxy)-1,2,3,4-tetrahydrocyclopenta[b]indol-3-yl)acetic acid at 1:00 pm. A full study (vehicle+3 doses) required four separate testing sessions, which occur on Mondays-Tuesdays and Thursdays-Fridays. During each of the testing sessions, the eight rats were divided into four treatment groups such that each group comprised N=2 for any given session. Rats were re-tested in subsequent testing sessions in a crossover design such that by the end of the four sessions, all animals had received all treatments in a pseudo-random order, and each group comprised N=8.

Exemplary Bradycardia Assay:

It was expressly contemplated that the rats could be used to show that a compound of the invention had no or substantially no activity for bradycardia. By way of illustration and not limitation, the rats were administered vehicle (PEG 400) and (R)-2-(7-(4-cyclopentyl-3-(trifluoromethyl)benzyloxy)-1,2,3,4-tetrahydrocyclopenta[b]indol-3-yl)acetic acid and heart rate was then measured over a 120 min period. Results are presented in FIG. 5. It is apparent from inspection of FIG. 5 that no or substantially no reduction of heart rate was exhibited in response to the treatment of rats with (R)-2-(7-(4-cyclopentyl-3-(trifluoromethyl)benzyloxy)-1,2,3,4-tetrahydrocyclopenta[b]indol-3-yl)acetic acid in comparison with vehicle. No or substantially no reduction of heart rate was indicative for (R)-2-(7-(4-cyclopentyl-3-(trifluoromethyl)benzyloxy)-1,2,3,4-tetrahydrocyclopenta[b]indol-3-yl)acetic acid, thus exhibiting no or substantially no activity for bradycardia.

Example 14

Powder X-Ray Diffraction (PXRD)

Figure 5:
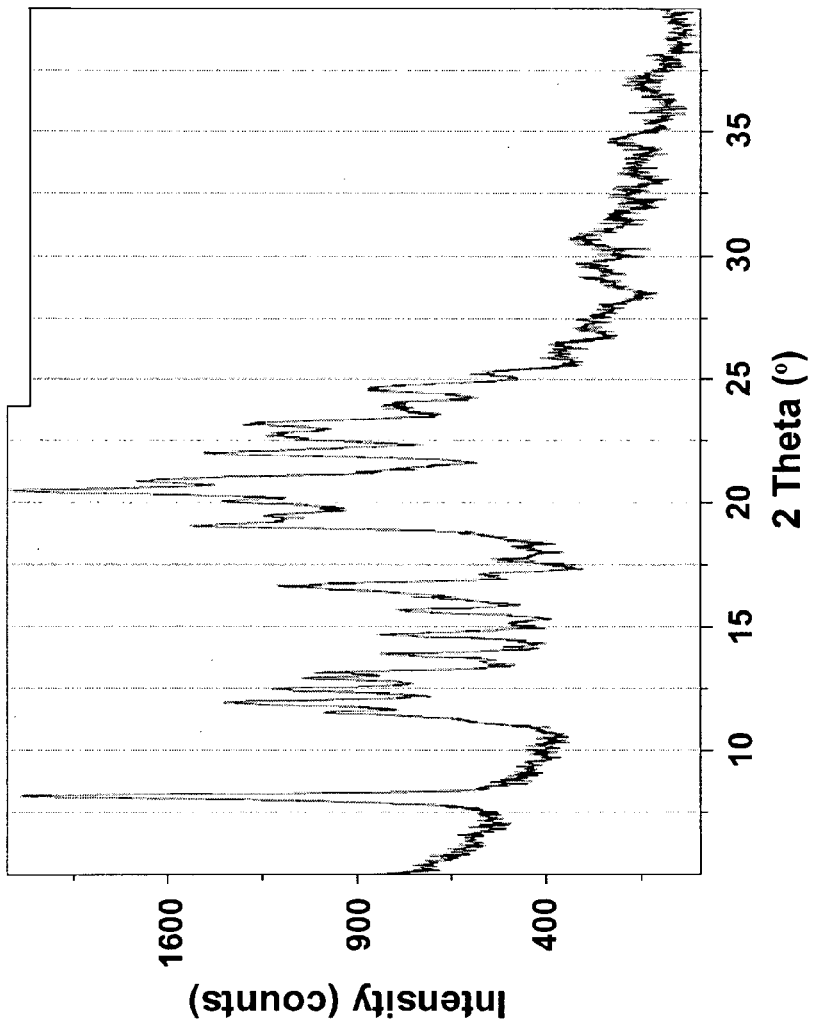
FIG. 5 shows a powder X-ray diffraction (PXRD) pattern for the L-arginine salt of (R)-2-(7-(4-cyclopentyl-3-(trifluoromethyl)benzyloxy)-1,2,3,4-tetrahydrocyclopenta[b]indol-3-yl)acetic acid (Compound of Formula (Ia)).

Powder X-ray Diffraction (PXRD) data were collected on an X'Pert PRO MPD powder diffractometer (PANalytical, Inc.) with a Cu source set at 45 kV and 40 mA, a Ni-filter to remove Cu Kβ radiation, and an X'Celerator detector. The instrument was calibrated by the vendor using a silicon powder standard NIST #640c. The calibration was found to be correct when it was tested with NIST #675 low-angle diffraction standard. Samples were prepared for PXRD scanning by placing several milligrams of gently ground compound onto a sample holder and smoothing as flat as possible by pressing weigh paper down on the sample with a flat object. The samples were analyzed using a spinning-sample stage. Scans cover the range of 5 to 40° 2θ. A continuous scan mode is used with a step size of 0.0167° 2θ. Diffraction data were viewed and analyzed with the X'Pert Data Viewer Software, version 1.0a and X'Pert HighScore Software, version 1.0b, FIG. 5 shows a powder X-ray diffraction (PXRD) pattern for the L-arginine salt of (R)-2-(7-(4-cyclopentyl-3-(trifluoromethyl)benzyloxy)-1,2,3,4-tetrahydrocyclopenta[b]indol-3-yl)acetic acid (Compound of Formula (Ia)).

Example 15

Differential Scanning Calorimetry (DSC)

Figure 6:
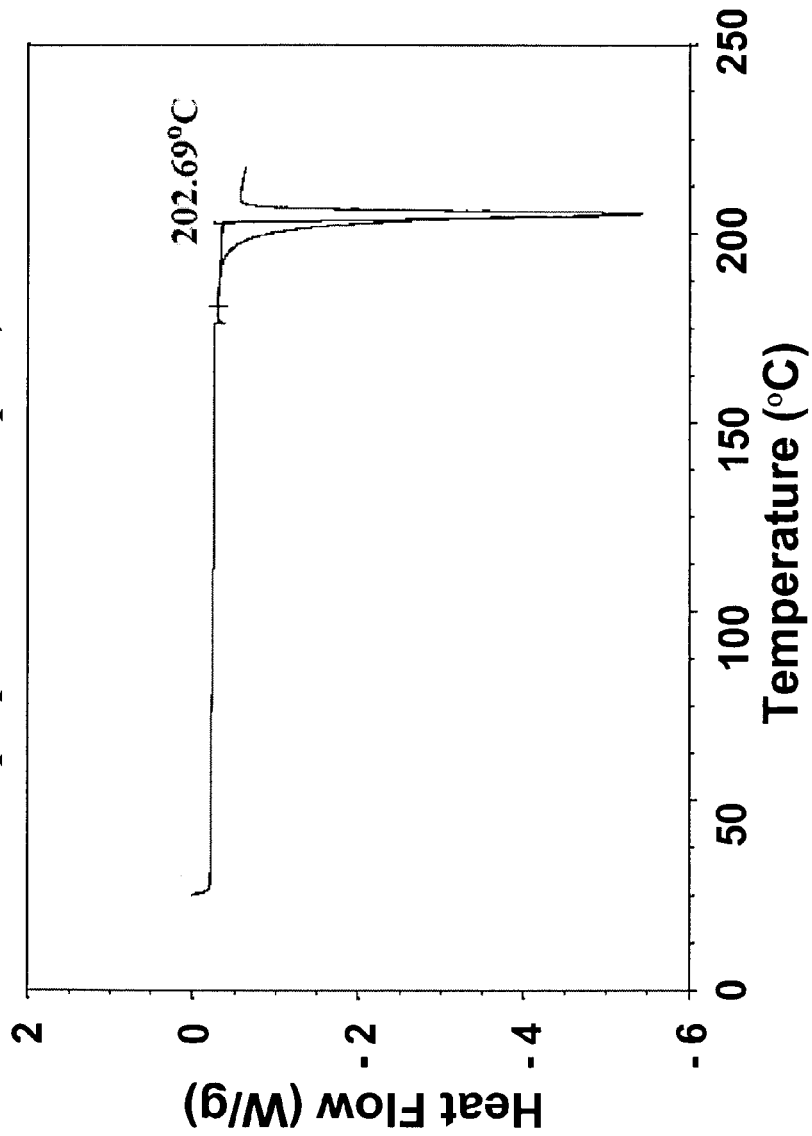
FIG. 6 shows a differential scanning calorimetry (DSC) thermogram for the L-arginine salt of (R)-2-(7-(4-cyclopentyl-3-(trifluoromethyl)benzyloxy)-1,2,3,4-tetrahydrocyclopenta[b]indol-3-yl)acetic acid (Compound of Formula (Ia)).

Differential Scanning calorimetry (DSC) was performed on a TA instruments, Inc. DSC Q2000 at 10° C./min. from ~25 to ~210° C. The instrument was calibrated at this scan rate by the vendor for temperature and energy using the melting point and enthalpy of fusion of an indium standard. Samples were prepared by piercing a sample-pan lid with a thumb tack or other sharp tool and taring this lid along with a sample-pan bottom on a Mettler Toldeo MX5 balance. The sample was placed in the bottom of the tared sample pan. The sample-pan lid fitted snuggly in the sample-pan bottom. The sample and pan were reweighed to get the sample weight. Thermal events (onset temperature, enthalpy of fusion, etc.) were calculated using the Universal Analysis 2000 software, version 4.1D, Build 4.1.0.16, FIG. 6 shows a differential scanning calorimetry (DSC) thermogram for the L-arginine salt of (R)-2-(7-(4-cyclopentyl-3-(trifluoromethyl)benzyloxy)-1,2,3,4-tetrahydrocyclopenta[b]indol-3-yl)acetic acid (Compound of Formula (Ia)).

Example 16

Thermal Gravimetric Analysis (TGA)

Figure 7:
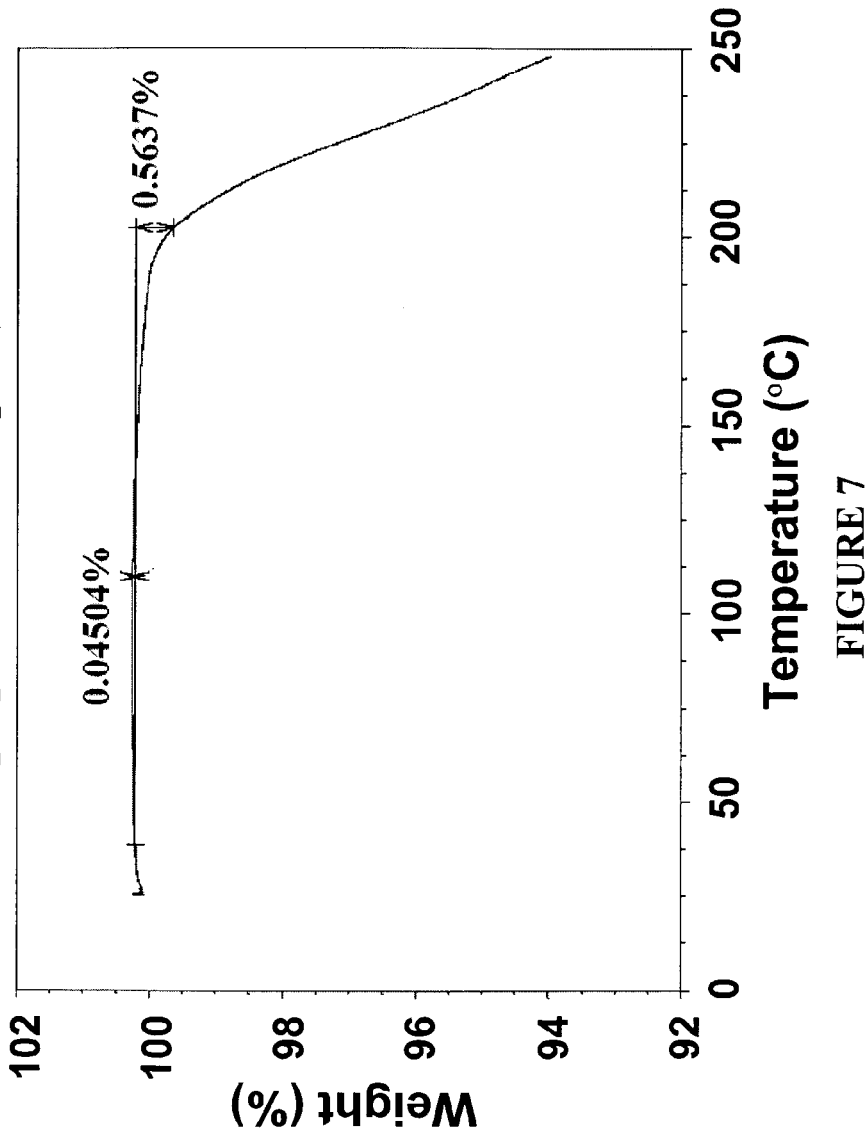
FIG. 7 shows a thermogravimetric analysis (TGA) thermogram for the L-arginine salt of (R)-2-(7-(4-cyclopentyl-3-(trifluoromethyl)benzyloxy)-1,2,3,4-tetrahydrocyclopenta[b]indol-3-yl)acetic acid (Compound of Formula (Ia)).

Thermal Gravimetric Analysis (TGA) was performed on the TA Instruments, Inc. TGA Q500. The instrument was calibrated by the vendor at 10° C./min. for temperature using the curie point of a ferromagnetic standard. The balance was calibrated with a standard weight. Sample scans were performed at 10° C./min. from ~25 to ~250° C. Sample was placed into an open sample pan, previously tared on the TGA balance. Thermal events such as weight-loss were calculated using the Universal Analysis 2000 software, version 4.1D, Build 4.1.0.16, FIG. 7 shows a thermogravimetric analysis (TGA) thermogram for the L-arginine salt of (R)-2-(7-(4-cyclopentyl-3-(trifluoromethyl)benzyloxy)-1,2,3,4-tetrahydrocyclopenta[b]indol-3-yl)acetic acid (Compound of Formula (Ia)).

Example 17

Vapor Sorption Analysis

Figure 8:
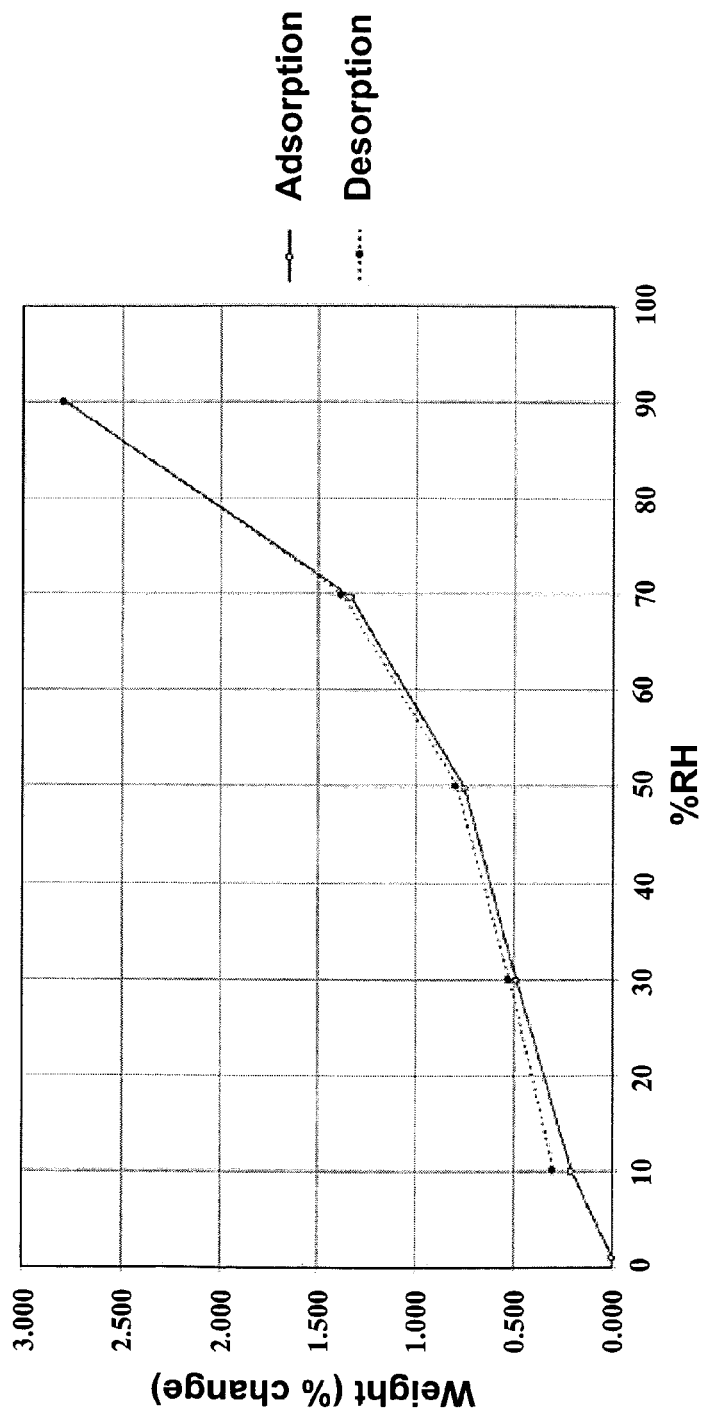
FIG. 8 shows a moisture sorption analysis for the L-arginine salt of (R)-2-(7-(4-cyclopentyl-3-(trifluoromethyl)benzyloxy)-1,2,3,4-tetrahydrocyclopenta[b]indol-3-yl)acetic acid (Compound of Formula (Ia)).

Hygroscopicity was measured using a dynamic moisture-sorption analyzer, VTI Corporation, SGA-100. The sample was placed as-is in a tared sample holder on the VTI balance. A drying step was run at 40° C. and 1% RH for 20 minutes. The isotherm conditions were 25° C. with steps of 20% RH from 10% RH up to 90% RH and back to 10% RH. Weight was checked every 5 minutes. Consecutive % weight change of <0.01% or 2 hours, whichever occurred first, was required before continuing to the next step, FIG. 8 shows a moisture sorption analysis for the L-arginine salt of (R)-2-(7-(4-cyclopentyl-3-(trifluoromethyl)benzyloxy)-1,2,3,4-tetrahydrocyclopenta[b]indol-3-yl)acetic acid (Compound of Formula (Ia)).

Example 18

Homogeneous Time-Resolved Fluorescence (HTRF®) Assay for Direct cAMP Measurement The compound (R)-2-(7-(4-cyclopentyl-3-(trifluoromethyl)benzyloxy)-1,2,3,4-tetrahydrocyclopenta[b]indol-3-yl)acetic acid was shown to be an agonist of the S1P1 receptor (e.g., human S1P1 receptor) using the HTRF® assay for direct cAMP measurement (Gabriel et al., Assay and Drug Development Technologies, 1:291-303, 2003) and recombinant CHO-K1 cells stably transfected with S1P1. CHO-K1 cells were obtained from ATCC® (Manassas, Va.; Catalog #CCL-61). The compound was determined to be an agonist of the S1P1 receptor and was detected in the HTRF® assay for direct cAMP measurement as a compound which decreased cAMP concentration. The HTRF® assay has been used to determine $EC_{50}$ values for S1P1 receptor agonists.

Principle of the Assay:

HTRF® assay kit was purchased from Cisbio-US, Inc. (Bedford, Mass.; Catalog #62AM4PEC). The HTRF® assay supported by the kit is a competitive immunoassay between endogenous cAMP produced by the CHO-K1 cells and tracer cAMP labeled with the dye d2. The tracer binding is visualized by a monoclonal anti-cAMP antibody labeled with Cryptate. The specific signal (i.e., fluorescence resonance energy transfer, FRET) is inversely proportional to the concentration of unlabeled cAMP in the standard or sample.

Standard Curve:

The fluorescence ratio (665 nm/620 nm) of the standards (0.17 to 712 nM cAMP) included in the assay was calculated and used to generate a cAMP standard curve according to the kit manufacturer's instructions. The fluorescence ratio of the samples (test compound or compound buffer) was calculated and used to deduce respective cAMP concentrations by reference to the cAMP standard curve.

Setup of the Assay:

The HTRF® assay was carried out using a two-step protocol essentially according to the kit manufacturer's instructions, in 20 µL total volume per well in 384-well plate format (ProxiPlates; PerkinElmer, Fremont, Calif.; catalog #6008280). To each of the experimental wells was transferred 1500 recombinant CHO-K1 cells in 5 µL phosphate buffered saline containing calcium chloride and magnesium chloride (PBS+; Invitrogen, Carlsbad, Calif.; catalog #14040) supplemented with IBMX (250 µM) and rolipram (20 µM) (phosphodiesterase inhibitors; Sigma-Aldrich, St. Louis, Mo.; catalog #15879 and catalog #R6520, respectively), followed by test compound in 5 µL compound buffer (PBS+ supplemented with 104 NKH477 (water-soluble forskolin derivative; SignaGen Laboratories, Gaithersburg, Md.; catalog #PKI-NKH477-010)) or 5 µL compound buffer. The plate was then incubated at room temperature for 1 h. To each well was then added 5 µL cAMP-d2 conjugate in lysis buffer and 5 µL Cryptate conjugate in lysis buffer according to the kit manufacturer's instructions. The plate was then further incubated at room temperature for 1 hour, after which the assay plate was read.

Assay Readout:

HTRF® readout was accomplished using a PHERAstar (BMG LABTECH Inc., Durham, N.C.) or EnVision™ (PerkinElmer, Fremont Calif.) microplate reader.

Certain compounds of the present invention and their corresponding activity values are shown in the following table

| Compound | $EC_{50}$ S1P1 (HTRF ®) |
|---|---|
| (R)-2-(7-(4-cyclopentyl-3-(trifluoromethyl)benzyloxy)-1,2,3,4-tetrahydrocyclopenta[b]indol-3-yl)acetic acid | 102 pM (n = 22) |

Citation of any reference throughout this application is not to be construed as an admission that such reference is prior art to the present application.

Those skilled in the art will recognize that various modifications, additions, substitutions, and variations to the illustrative examples set forth herein can be made without departing from the spirit of the invention and are, therefore, considered within the scope of the invention.

What is claimed is:

1. A process for preparing an L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia):

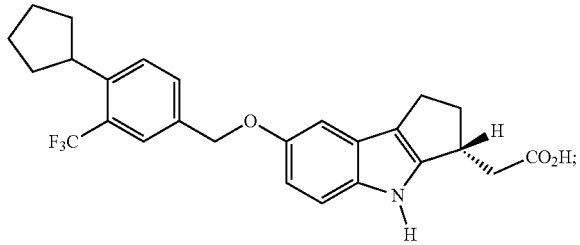

(Ia)

comprising the following steps:
a) hydrolyzing a compound of Formula (IIk):

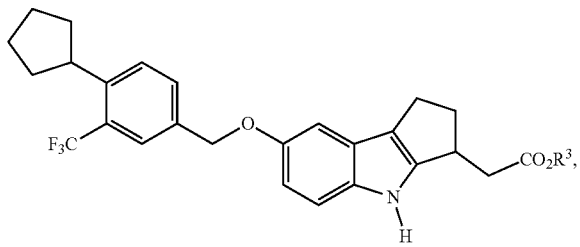

(IIk)

wherein $R^3$ is $C_1$-$C_6$ alkyl;
in the presence of a lipase and a hydrolyzing-step solvent to form said (R)-2-(7-(4-cyclopentyl-3-(trifluoromethyl)benzyloxy)-1,2,3,4-tetrahydrocyclopenta[b]indol-3-yl)acetic acid of Formula (Ia); and
b) contacting said (R)-2-(7-(4-cyclopentyl-3-(trifluoromethyl)benzyloxy)-1,2,3,4-tetrahydrocyclopenta[b]indol-3-yl)acetic acid (Formula (Ia)) with L-arginine or a salt thereof, in the presence of a contacting-step solvent and H₂O to form said L-arginine salt of (R)-2-(7-(4-cyclopentyl-3-(trifluoromethyl)benzyloxy)-1,2,3,4-tetrahydrocyclopenta[b]indol-3-yl)acetic acid of Formula (Ia).

2. The process according to claim 1, wherein $R^3$ is ethyl.

3. The process according to claim 1, wherein said lipase is immobilized *Candida antarctica* lipase B.

4. The process according to claim 1, wherein said hydrolyzing-step solvent comprises dimethylformamide (DMF), dimethylacetamide (DMA), dimethylsulfoxide (DMSO), tetrahydrofuran (THF), or acetonitrile.

5. The process according to claim 1, wherein said hydrolyzing-step solvent comprises acetonitrile.

6. The process according to claim 1, wherein:
said compound of Formula (IIk) is:

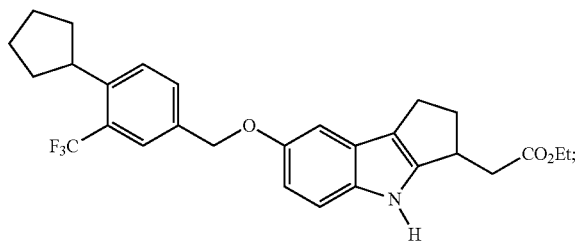 [SMILES: CCOC(=O)CC1CCc2c1[nH]c1ccc(OCc3ccc(C4CCCC4)c(C(F)(F)F)c3)cc21]

said lipase is immobilized *Candida antarctica* lipase B; and
said hydrolyzing-step solvent comprises acetonitrile.

7. The process according to claim 1, wherein said hydrolyzing in step a), is conducted in the presence of a phosphate buffer at a pH of about 7.6 to about 8.0.

8. The process according to claim 7, wherein said phosphate buffer is a potassium phosphate buffer.

9. The process according to claim 1, wherein said hydrolyzing in step a), is conducted at a temperature of about 30° C. to about 55° C.

10. The process according to claim 1, wherein said hydrolyzing in step a), further comprises the step of isolating said (R)-2-(7-(4-cyclopentyl-3-(trifluoromethyl)benzyloxy)-1,2,3,4-tetrahydrocyclopenta[b]indol-3-yl)acetic acid, wherein after said isolating, said (R)-2-(7-(4-cyclopentyl-3-(trifluoromethyl)benzyloxy)-1,2,3,4-tetrahydrocyclopenta[b]indol-3-yl)acetic acid has an enantiomeric excess of about 95% or greater.

11. The process according to claim 1, wherein said contacting-step solvent comprises isopropyl alcohol.

12. The process according to claim 1, further comprising the step of isolating said L-arginine salt of (R)-2-(7-(4-cyclopentyl-3-(trifluoromethyl)benzyloxy)-1,2,3,4-tetrahydrocyclopenta[b]indol-3-yl)acetic acid, wherein after said isolating, said L-arginine salt of (R)-2-(7-(4-cyclopentyl-3-(trifluoromethyl)benzyloxy)-1,2,3,4-tetrahydrocyclopenta[b]indol-3-yl)acetic acid has a purity of about 95% or greater as determined by HPLC.

13. The process according to claim 1, further comprising the step of isolating said L-arginine salt of (R)-2-(7-(4-cyclopentyl-3-(trifluoromethyl)benzyloxy)-1,2,3,4-tetrahydrocyclopenta[b]indol-3-yl)acetic acid, wherein after said isolating, said L-arginine salt of (R)-2-(7-(4-cyclopentyl-3-(trifluoromethyl)benzyloxy)-1,2,3,4-tetrahydrocyclopenta[b]indol-3-yl)acetic acid has an enantiomeric excess of about 95% or greater.

14. The process according to claim 1, further comprising the step of isolating said L-arginine salt of (R)-2-(7-(4-cyclopentyl-3-(trifluoromethyl)benzyloxy)-1,2,3,4-tetrahydrocyclopenta[b]indol-3-yl)acetic acid wherein said L-arginine salt of (R)-2-(7-(4-cyclopentyl-3-(trifluoromethyl)benzyloxy)-1,2,3,4-tetrahydrocyclopenta[b]indol-3-yl)acetic acid is a crystalline form.

15. The process according to claim 14, wherein said crystalline form has a powder X-ray diffraction (PXRD) pattern substantially as shown in FIG. 5, a differential scanning calorimetry (DSC) trace substantially as shown in FIG. 6, a thermogravimetric analysis (TGA) profile substantially as shown in FIG. 7, or a dynamic vapor sorption (DVS) profile substantially as shown in FIG. 8.

16. A process of claim 1, further comprising admixing an L-arginine salt of (R)-2-(7-(4-cyclopentyl-3-(trifluoromethyl)benzyloxy)-1,2,3,4-tetrahydrocyclopenta[b]indol-3-yl)acetic acid and a pharmaceutically acceptable carrier to form a pharmaceutical composition.

17. The process according to claim 1, further comprising the step of isolating said L-arginine salt of (R)-2-(7-(4-cyclopentyl-3-(trifluoromethyl)benzyloxy)-1,2,3,4-tetrahydrocyclopenta[b]indol-3-yl)acetic acid, wherein after said isolating, said L-arginine salt of (R)-2-(7-(4-cyclopentyl-3-(trifluoromethyl)benzyloxy)-1,2,3,4-tetrahydrocyclopenta[b]indol-3-yl)acetic acid has a purity of about 95% or greater as determined by HPLC and has an enantiomeric excess of about 95% or greater.

18. The process according to claim 17, further comprising admixing an L-arginine salt of (R)-2-(7-(4-cyclopentyl-3-(trifluoromethyl)benzyloxy)-1,2,3,4-tetrahydrocyclopenta[b]indol-3-yl)acetic acid and a pharmaceutically acceptable carrier to form a pharmaceutical composition.

19. The process according to claim 6, wherein said hydrolyzing in step a), is conducted in the presence of a phosphate buffer at a pH of about 7.6 to about 8.0.

20. The process according to claim 19, wherein said phosphate buffer is a potassium phosphate buffer.

21. The process according to claim 20, wherein said hydrolyzing in step a), is conducted at a temperature of about 30° C. to about 55° C.

22. The process according to claim 21, wherein said contacting-step solvent comprises isopropyl alcohol.

23. The process according to claim 22, further comprising the step of isolating said L-arginine salt of (R)-2-(7-(4-cyclopentyl-3-(trifluoromethyl)benzyloxy)-1,2,3,4-tetrahydrocyclopenta[b]indol-3-yl)acetic acid, wherein after said isolating, said L-arginine salt of (R)-2-(7-(4-cyclopentyl-3-(trifluoromethyl)benzyloxy)-1,2,3,4-tetrahydrocyclopenta[b]indol-3-yl)acetic acid has a purity of about 95% or greater as determined by HPLC and has an enantiomeric excess of about 95% or greater.

24. The process according to claim 23, further comprising admixing an L-arginine salt of (R)-2-(7-(4-cyclopentyl-3-(trifluoromethyl)benzyloxy)-1,2,3,4-tetrahydrocyclopenta[b]indol-3-yl)acetic acid and a pharmaceutically acceptable carrier to form a pharmaceutical composition.

* * * * *

UNITED STATES PATENT AND TRADEMARK OFFICE
CERTIFICATE OF CORRECTION

PATENT NO. : 8,853,419 B2
APPLICATION NO. : 13/575458
DATED : October 7, 2014
INVENTOR(S) : Antonio Garrido Montalban et al.

It is certified that error appears in the above-identified patent and that said Letters Patent is hereby corrected as shown below:

On the Title Page

Under item (56) Reference Cited -- Other Publications

Page 3, Col. 1, line 45, delete "Signlaing" and insert --Signaling--;

Page 3, Col. 1, line 51, delete "Pathogensis" and insert --Pathogenesis--;

Page 3, Col. 2, line 29, delete "Lumphocyte" and insert --Lymphocyte--;

Page 3, Col. 2, line 67, delete "Sytems," and insert --Systems,--;

Page 4, Col. 1, line 28, delete "cappillary" and insert --capillary--;

Page 4, Col. 2, line 67, delete "Amerlioration" and insert --Amelioration--;

Page 5, Col. 1, line 1, delete "Predictiability" and insert --Predictability--;

Page 5, Col. 2, line 54, delete "efficent" and insert --efficient--;

In the Claims

Col. 101, Claim 21, line 12-13, delete "30 ° C" and insert --30 °C--;

Col. 101, Claim 21, line 13, delete "55 ° C" and insert --55 °C--.

Signed and Sealed this
Tenth Day of February, 2015

Michelle K. Lee
*Deputy Director of the United States Patent and Trademark Office*